US012214009B2

(12) United States Patent
Widgerow et al.

(10) Patent No.: US 12,214,009 B2
(45) Date of Patent: *Feb. 4, 2025

(54) COMPOSITIONS AND METHODS FOR IMPROVING BRUISING AND REJUVENATING SKIN

(71) Applicant: Alastin Skincare, Inc., Carlsbad, CA (US)

(72) Inventors: Alan David Widgerow, Irvine, CA (US); John A. Garruto, Encinitias, CA (US)

(73) Assignee: Alastin Skincare, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/212,119

(22) Filed: Jun. 20, 2023

(65) Prior Publication Data

US 2023/0346875 A1 Nov. 2, 2023

Related U.S. Application Data

(63) Continuation of application No. 17/384,478, filed on Jul. 23, 2021, now abandoned, which is a continuation of application No. PCT/US2020/031867, filed on May 7, 2020.

(60) Provisional application No. 62/967,383, filed on Jan. 29, 2020, provisional application No. 62/881,783, filed on Aug. 1, 2019, provisional application No. 62/845,063, filed on May 8, 2019.

(51) Int. Cl.
| *A61K 38/06* | (2006.01) |
| *A61K 9/00* | (2006.01) |
| *A61K 9/127* | (2006.01) |
| *A61K 38/07* | (2006.01) |
| *A61K 38/08* | (2019.01) |
| *A61K 38/40* | (2006.01) |
| *A61P 17/00* | (2006.01) |
| *A61P 31/04* | (2006.01) |

(52) U.S. Cl.
CPC ............ *A61K 38/06* (2013.01); *A61K 9/0014* (2013.01); *A61K 9/127* (2013.01); *A61K 38/07* (2013.01); *A61K 38/08* (2013.01); *A61K 38/40* (2013.01); *A61P 17/00* (2018.01); *A61P 31/04* (2018.01)

(58) Field of Classification Search
None
See application file for complete search history.

(56) References Cited

U.S. PATENT DOCUMENTS

| 5,629,015 | A | 5/1997 | Ribier et al. | |
| 9,248,160 | B1 * | 2/2016 | Obagi | A61K 36/48 |
| 9,265,792 | B2 * | 2/2016 | Riley | A61K 38/18 |
| 10,086,035 | B2 | 10/2018 | Garruto et al. | |
| 10,286,030 | B2 | 5/2019 | Garruto et al. | |
| 10,493,011 | B2 * | 12/2019 | Widgerow | A61Q 19/00 |
| 11,052,032 | B2 * | 7/2021 | Widgerow | A61K 8/64 |
| 11,103,455 | B2 | 8/2021 | Garruto et al. | |
| 11,426,443 | B2 | 8/2022 | Garruto et al. | |
| 2014/0120141 | A1 | 5/2014 | Anton et al. | |
| 2017/0224760 | A1 * | 8/2017 | Garruto | A61K 8/37 |
| 2019/0038539 | A1 | 2/2019 | Garruto et al. | |

FOREIGN PATENT DOCUMENTS

| CN | 108158910 A | 6/2018 |
| KR | 20080046794 A | 5/2008 |
| WO | WO-2017/136600 A1 | 8/2017 |
| WO | WO-2020/227526 A1 | 11/2020 |

OTHER PUBLICATIONS

Takayama et al. (Biochem. Cell Biol. 90: 1-7 (2011)) (Year: 2011).*
Mayo Clinic (Housecall: Easy bruising and age; Feb. 5, 2018) (Year: 2018).*
Bekker et al., "Relating rheological measurements to primary and secondary skin feeling when mineral-based and Fischer-Tropsch wax-based cosmetic emulsions and jellies are applied to the skin," International Journal of Cosmetic Science, vol. 35, No. 4, Mar. 18, 2013, pp. 354-361.
Chang et al., "Erythrocyte efferocytosis modulates macrophages towards recovery after intracerebral hemorrhage," The Journal of Clinical Investigation, vol. 128, No. 2, Feb. 2018, pp. 607-624.
International Search Report and Written Opinion on PCT Appl. Ser. No. PCT/US2020/031867 dated Oct. 8, 2020 (12 pages).
Jeney et al., "Natural History of the Bruise: Formation, Elimination, and Biological Effects of Oxidized Hemoglobin," Oxidative Medicine and Cellular Longevity, Apr. 12, 2013, pp. 1-9.
Takayama et al., "Roles of lactoferrin on skin wound healing," Biochem. Cell Biol., vol. 90, Sep. 18, 2011, pp. 1-7.
The PLOS ONE Editors, "Retraction: Arnica montana Stimulates Extracellular Matrix Gene Expression in a Macrophage Cell Line Differentiated to Wound-Healing Phenotype," PLOS ONE, Jun. 20, 2019, pp. 1-2.
Widgerow et al., "Developing a Topical Adjunct to Injectable Procedures," Journal of Drugs in Dermatology, vol. 19, No. 4, Apr. 2020, pp. 398-404.
Zwirzitz et al., "Lactoferrin is a natural inhibitor of plasminogen activation.," Journal of Biological Chemistry, vol. 293, No. 22, Apr. 18, 2018, pp. 8600-8613.
Purpura's disease, "Purpura," its vocabulary dictionary, nursing roo! [Kango Run], Nov. 7, 2018, [Search on May 31, 2024], Internet URL: https://www.kango-roo.com/word/21127.
Sklirou et al., "Hexapeptide-11 is a novel modulator of the proteostasis network in human diploid fibroblasts," Redox Biology, Elsevier, Apr. 29, 2015, vol. 5, pp. 205-215.
Yoga Urban Clinic, "Yoga Urban Clinic Newsletter Jun. 2013 issue," Yoga Urban Clinic Newsletter, Jun. 26, 2013, [search on May 31, 2024], Internet URL: https://yoga-urban.jp/blog/002202.html.

* cited by examiner

*Primary Examiner* — Sergio Coffa
(74) *Attorney, Agent, or Firm* — Sunit Talapatra; Foley & Lardner LLP

(57) ABSTRACT

Compositions and methods for improving bruising, stimulating elastin and/or collagen production, stimulating intrinsic hyaluronic acid production, stimulating adipogenesis, reducing inflammation, or combinations thereof are provided herein. Compositions and methods described herein may be used following a cosmetic procedure.

18 Claims, 25 Drawing Sheets

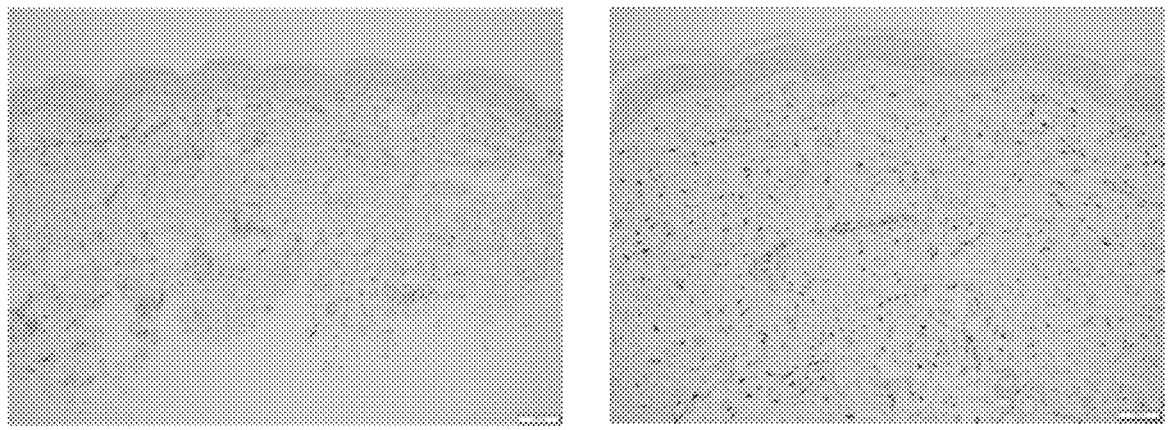

Fig. 16F

RESULTS:

TABLE SUMMARY

| MICROORGANISM | | INITIAL INOCULUM/gm | COLONY FORMING UNITS/gm | |
|---|---|---|---|---|
| | | | 14 DAYS | 28 DAYS |
| Aspergillus brasiliensis | (mold) | 3.8E5 | <10 | <10 |
| Candida albicans | (yeast) | 1.6E5 | <10 | <10 |
| Escherichia coli | (bacteria) | 8.0E5 | <10 | <10 |
| Pseudomonas aeruginosa | (bacteria) | 1.3E6 | <10 | <10 |
| Staphylococcus aureus | (bacteria) | 9.3E5 | <10 | <10 |

Note: Numbers in the report such as 2.3E5 are an alternate exponential format for $2.3 \times 10^5$.

LOG REDUCTION FROM INITIAL INOCULUM

| | 14 DAYS | 28 DAYS |
|---|---|---|
| Aspergillus brasiliensis | 4.6 | 4.6 |
| Candida albicans | 4.2 | 4.2 |
| Escherichia coli | 4.9 | 4.9 |
| Pseudomonas aeruginosa | 5.1 | 5.1 |
| Staphylococcus aureus | 5.0 | 5.0 |

CONCLUSION:

The sample described above meets the USP criteria of acceptance for the Antimicrobial Effectiveness Test for Category 2.

Fig. 17

COMPOSITIONS AND METHODS FOR IMPROVING BRUISING AND REJUVENATING SKIN

CROSS-REFERENCE

This application is a continuation of U.S. patent application Ser. No. 17/384,478 filed on Jul. 23, 2021, which application is a continuation of International Application No. PCT/US2020/031867, filed May 7, 2020, which claims the benefit of U.S. Provisional Patent Application No. 62/967,383 filed on Jan. 29, 2020; U.S. Provisional Patent Application No. 62/881,783 filed on Aug. 1, 2019; and U.S. Provisional Patent Application No. 62/845,063 filed on May 8, 2019, each of which is incorporated herein by reference in its entirety.

BACKGROUND

A bruise may appear hours after injury to the tissues below the skin's surface or in some instances, a bruise appears instantly when a blood vessel is breached such as during the injection process. Red blood cells extravasate into the surrounding tissue, and breakdown of these cells by macrophages results in loss of oxygen, giving the red blood cells a bluish hue. The byproducts of hemoglobin breakdown (heme, biliverdin, bilirubin, and hemosiderin) transmit the different colors to the skin that slowly resolve once these pigments are absorbed by the macrophages and digested. Due to the negative aesthetics of the skin discoloration that can occur for multiple days, there is a need for resolving the bruising process more quickly.

BRIEF SUMMARY

Described herein are compositions and methods for improving bruising. In some instances, the bruising is caused by an injection. Compositions and methods as described herein can improve bruising by improving macrophage function. Compositions and methods as described herein may further stimulate elastin and/or collagen production, intrinsic hyaluronic acid production, adipogenesis, or reduce inflammation.

Efficacy of an active ingredient depends on several factors including its bioavailability. For topical compositions, skin penetration ability is important for bioavailability of the active ingredient. Some methods for improving skin penetration and bioavailability can be too aggressive such as methods employing a skin barrier disrupter like an alcohol. Delivery systems employing liposomes may improve delivery and skin penetration of topical compositions in a safe and efficacious manner. Described herein are liposomal compositions for improved distribution, efficacy, bioavailability, and/or activity. Liposomal compositions may improve distribution, efficacy, bioavailability, and/or activity by improving delivery and skin penetration.

An aspect described herein are topical compositions for improving bruising following injection of a filler comprising: one or more ingredients encapsulated in a liposome; a tripeptide-1; and a hexapeptide-12, wherein the topical composition improves healing or appearance of a bruise following injection of the filler. In one feature, the tripeptide-1 is present at 1-10 ppm. In one feature, the tripeptide-1 comprises palmitoyl tripeptide-1, myristoyl tripeptide-1, or a combination thereof. In one feature, the hexapeptide-12 comprises palmitoyl hexapeptide-12, myristoyl hexapeptide-12, or a combination thereof. In one feature, the hexapeptide-12 is present at 1-10 ppm. In one feature, a first ingredient of the one or more ingredients encapsulated in the liposome is hexapeptide-11. In one feature, the hexapeptide-11 is present at 50-150 ppm. In one feature, a second ingredient of the one or more ingredients encapsulated in the liposome is hexapeptide-38. In one feature, the hexapeptide-38 is acetyl hexapeptide-38. In one feature, the topical compositions further comprise a tetrapeptide. In one feature, the tetrapeptide is tetrapeptide-2. In one feature, the tetrapeptide-2 is acetyl tetrapeptide-2. In one feature, the topical compositions further comprise phosphatidylserine. In one feature, the phosphatidylserine is present at no more than 0.050% by weight (wt. %). In one feature, the phosphatidylserine is present in a range of about 0.005 wt. % to about 0.1 wt. %. In one feature, the phosphatidylserine is present at no more than 5.0 wt %. In one feature, the phosphatidylserine is present at 0.1 wt %. In one feature, a third ingredient of the one or more ingredients encapsulated in the liposome is lactoferrin. In one feature, the lactoferrin is present at no more than 0.050 wt. %. In one feature, the lactoferrin is present in a range of about 0.005 wt. % to about 0.1 wt. %. In one feature, the lactoferrin is present at no more than 5.0 wt %. In one feature, the topical compositions further comprise *Ledum palustre* extract. In one feature, the *Ledum palustre* extract is present in a range of about 0.1 wt. % to about 2.5 wt. %. In one feature, the topical compositions further comprise dill extract. In one feature, the dill extract is present in a range of about 0.01 wt. % to about 2.5 wt. %. In one feature, the topical compositions further comprise hydroxymethoxyphenyl decanone. In one feature, the hydroxymethoxyphenyl decanone is present in a range of about 0.001 wt. % to about 2.5 wt. %. In one feature, the topical compositions further comprise *Tremella fuciformis* extract. In one feature, the *Tremella fuciformis* extract is present in a range of about 0.001 wt. % to about 2.5 wt. %. In one feature, the topical compositions further comprise sodium hyaluronate crosspolymer. In one feature, the sodium hyaluronate crosspolymer is present in a range of about 0.0001 wt. % to about 2.5 wt. %. In one feature, the topical compositions further comprise xylitylglucoside, anhydroxylitol, xylitol, or combinations thereof. In one feature, the xylitylglucoside, anhydroxylitol, xylitol, or combinations thereof is present in a range of about 0.25 wt. % to about 5 wt. %. In one feature, the topical compositions further comprise butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, or combinations thereof. In one feature, the topical composition is aqueous. In one feature, a viscosity of the topical composition is in a range of about 8,000 centipoise (cps) to about 30,000 cps. In one feature, the filler is a soft tissue filler. In one feature, the filler is a dermal filler.

An aspect described herein are topical compositions for improving bruising comprising: one or more ingredients encapsulated in a liposome, wherein a first ingredient of the one or more ingredients encapsulated in the liposome is hexapeptide-11; a tripeptide-1; and a hexapeptide-12, wherein the topical composition improves healing or appearance of a bruise. In one feature, the tripeptide-1 is present at 1-10 ppm. In one feature, the tripeptide-1 comprises palmitoyl tripeptide-1, myristoyl tripeptide-1, or a combination thereof. In one feature, the hexapeptide-12 comprises palmitoyl hexapeptide-12, myristoyl hexapeptide-12, or a combination thereof. In one feature, the hexapeptide-12 is present at 1-10 ppm. In one feature, the hexapeptide-11 is present at 50-150 ppm. In one feature, a second ingredient of the one or more ingredients encapsulated in the liposome is hexapeptide-38. In one feature, the hexapeptide-38 is acetyl hexapeptide-38. In one feature, the topical compositions further comprise a tetrapeptide. In one feature, the tetrapeptide is tetrapeptide-2. In one feature, the tetrapeptide-2 is acetyl tetrapeptide-2. In one feature, the topical compositions further comprise phosphatidylserine. In one feature, the phosphatidylserine is present at no more than 0.050% by weight (wt. %). In one feature, the phosphatidylserine is present in a range of about 0.005 wt. % to about 0.1 wt. %. In one feature, the phosphatidylserine is present at no more than 5.0 wt %. In one feature, the phosphatidylserine is present at 0.1 wt %. In one feature, a third ingredient of the one or more ingredients encapsulated in the liposome is lactoferrin. In one feature, the lactoferrin is present at no more than 0.050 wt. %. In one feature, the lactoferrin is present in a range of about 0.005 wt. % to about 0.1 wt. %. In one feature, the lactoferrin is present at no more than 5.0 wt %. In one feature, the topical compositions further comprise *Ledum palustre* extract. In one feature, the *Ledum palustre* extract is present in a range of about 0.1 wt. % to about 2.5 wt. %. In one feature, the topical compositions further comprise dill extract. In one feature, the dill extract is present in a range of about 0.01 wt. % to about 2.5 wt. %. In one feature, the topical compositions further comprise hydroxymethoxyphenyl decanone. In one feature, the hydroxymethoxyphenyl decanone is present in a range of about 0.001 wt. % to about 2.5 wt. %. In one feature, the topical compositions further comprise *Tremella fuciformis* extract. In one feature, the *Tremella fuciformis* extract is present in a range of about 0.001 wt. % to about 2.5 wt. %. In one feature, the topical compositions further comprise sodium hyaluronate crosspolymer. In one feature, the sodium hyaluronate crosspolymer is present in a range of about 0.0001 wt. % to about 2.5 wt. %. In one feature, the topical compositions further comprise xylitylglucoside, anhydroxylitol, xylitol, or combinations thereof. In one feature, the xylitylglucoside, anhydroxylitol, xylitol, or combinations thereof is present in a range of about 0.25 wt. % to about 5 wt. %. In one feature, the topical compositions further comprise butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, or combinations thereof. In one feature, the topical composition is aqueous. In one feature, a viscosity of the topical composition is in a range of about 8,000 centipoise (cps) to about 30,000 cps. In one feature, the bruise appears following a cosmetic procedure. In one feature, the cosmetic procedure is an injection of a filler. In one feature, the cosmetic procedure is an injection of a neurotoxin. In one feature, the cosmetic procedure is an invasive surgery. In one feature, the bruise appears following a medical procedure. In one feature, the medical procedure is a therapeutic injection. In one feature, the medical procedure is an intravenous injection. In one feature, the medical procedure is an invasive surgery. In one feature, the bruise appears following a trauma.

An aspect described herein are topical compositions for rejuvenating skin comprising a liposome encapsulating: one or more peptides; and lactoferrin, wherein the topical composition rejuvenates skin. In one feature, the topical compositions further comprise tripeptide-1. In one feature, the tripeptide is tripeptide-1. In one feature, the tripeptide-1 is present at 1-10 ppm. In one feature, the tripeptide-1 comprises palmitoyl tripeptide-1, myristoyl tripeptide-1, or a combination thereof. In one feature, the topical compositions further comprise hexapeptide-12. In one feature, the hexapeptide-12 comprises palmitoyl hexapeptide-12, myristoyl hexapeptide-12, or a combination thereof. In one feature, the hexapeptide-12 is present at 1-10 ppm. In one feature, a first peptide of the one or more peptides comprises hexapeptide-11. In one feature, the hexapeptide-11 is present at 50-150 ppm. In one feature, a second peptide of the one or more peptides comprises hexapeptide-38. In one feature, the hexapeptide-38 is acetyl hexapeptide-38. In one feature, the topical compositions further comprise a tetrapeptide. In one feature, the tetrapeptide is tetrapeptide-2. In one feature, the tetrapeptide-2 is acetyl tetrapeptide-2. In one feature, the topical compositions further comprise phosphatidylserine. In one feature, the phosphatidylserine is present at no more than 0.050% by weight (wt. %). In one feature, the phosphatidylserine is present in a range of about 0.005 wt. % to about 0.1 wt. %. In one feature, the phosphatidylserine is present at no more than 5.0 wt %. In one feature, the phosphatidylserine is present at 0.1 wt %. In one feature, the lactoferrin is present at no more than 0.050 wt. %. In one feature, the lactoferrin is present in a range of about 0.005 wt. % to about 0.1 wt. %. In one feature, the lactoferrin is present at no more than 5.0 wt %. In one feature, the topical compositions further comprise *Ledum palustre* extract. In one feature, the *Ledum palustre* extract is present in a range of about 0.1 wt. % to about 2.5 wt. %. In one feature, the topical compositions further comprise dill extract. In one feature, the dill extract is present in a range of about 0.01 wt. % to about 2.5 wt. %. In one feature, the topical compositions further comprise hydroxymethoxyphenyl decanone. In one feature, the hydroxymethoxyphenyl decanone is present in a range of about 0.001 wt. % to about 2.5 wt. %. In one feature, the topical compositions further comprise *Tremella fuciformis* extract. In one feature, the *Tremella fuciformis* extract is present in a range of about 0.001 wt. % to about 2.5 wt. %. In one feature, the topical compositions further comprise sodium hyaluronate crosspolymer. In one feature, the sodium hyaluronate crosspolymer is present in a range of about 0.0001 wt. % to about 2.5 wt. %. In one feature, the topical compositions further comprise xylitylglucoside, anhydroxylitol, xylitol, or combinations thereof. In one feature, the xylitylglucoside, anhydroxylitol, xylitol, or combinations thereof is present in a range of about 0.25 wt. % to about 5 wt. %. In one feature, the topical compositions further comprise butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, or combinations thereof. In one feature, the topical composition is aqueous. In one feature, a viscosity of the topical composition is in a range of about 8,000 centipoise (cps) to about 30,000 cps.

An aspect described herein are methods for improving bruising in an individual, comprising administering a topical composition as described herein. In one feature, the bruising is improved by at least 5%, 10%, 15%, 20%, 25%, 30%, 40%, 50%, 60%, 70%, 80%, 90%, or more than 90%. In one feature, the bruising is improved by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×. In one feature, the bruising is improved at least 1 day after administering the topical composition. In one feature, the bruising is improved at least 2 days after administering the topical composition. In one feature, improvements in bruising comprises accelerated resolution of a bruise, reduced size of a bruise, reduced discoloration of skin, reduced swelling, or combinations thereof.

An aspect described herein are methods for improving macrophage function in an individual, comprising administering a topical composition as described herein. In one feature, the improved macrophage function comprises improved phagocytosis. In one feature, the improved macrophage function comprises improved hemosiderin clearance. In one feature, the macrophage function is improved by at least 5%, 10%, 15%, 20%, 25%, 30%, 40%, 50%, 60%, 70%, 80%, 90%, or more than 90%. In one feature, the macrophage function is improved by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

An aspect described herein are methods for stimulating production of elastin, collagen, or a combination thereof in an individual, comprising administering a topical composition as described herein. In one feature, the production of elastin, collagen, or a combination thereof is stimulated by at least 5%, 10%, 15%, 20%, 25%, 30%, 40%, 50%, 60%, 70%, 80%, 90%, or more than 90%. In one feature, the production of elastin, collagen, or a combination thereof is stimulated by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

An aspect described herein are methods for stimulating intrinsic hyaluronic acid production in an individual, comprising administering a topical composition as described herein. In one feature, the intrinsic hyaluronic acid production is stimulated by at least 5%, 10%, 15%, 20%, 25%, 30%, 40%, 50%, 60%, 70%, 80%, 90%, or more than 90%. In one feature, the intrinsic hyaluronic acid production is stimulated by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

An aspect described herein are methods for increasing adipogenesis in an individual, comprising administering a topical composition as described herein. In one feature, adipogenesis is increased by at least 5%10%1, 15%, 20%, 25%, 30%, 40%, 50%, 60%, 70%, 80%, 90%, or more than 90%. In one feature, adipogenesis is increased by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

An aspect described herein are methods for reducing inflammation in an individual, comprising administering a topical composition as described herein. In one feature, inflammation is reduced by at least 5%, 10%, 15%, 20%, 25%, 30%, 40%, 50%, 60%, 70%, 80%, 90%, or more than 90%. In one feature, inflammation is reduced by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

An aspect described herein are methods for administering a topical composition. In one feature, the topical composition is administered following a cosmetic procedure. In one feature, the topical composition is administered prior to a cosmetic procedure. In one feature, the cosmetic procedure comprises injection of a filler. In one feature, the filler is a soft tissue filler. In one feature, the filler is a dermal filler. In one feature, the cosmetic procedure is a microneedling procedure. In one feature, the microneedling procedure is a radiofrequency microneedling procedure. In one feature, the topical composition is administered at least 1 day prior to the microneedling procedure. In one feature, the topical composition is administered at least 1 week prior to the microneedling procedure. In one feature, the topical composition is administered at least 2 weeks prior to the microneedling procedure. In one feature, the topical composition is administered at least 1 day following the microneedling procedure. In one feature, the topical composition is administered at least 1 week following the microneedling procedure. In one feature, the topical composition is administered at least 2 weeks following the microneedling procedure. In one feature, the topical composition is administered immediately prior to the injection of the filler. In one feature, the topical composition is administered at least 1 day prior to the injection of the filler. In one feature, the topical composition is administered at least 1 week prior to the injection of the filler. In one feature, the topical composition is administered at least 2 weeks prior to the injection of the filler. In one feature, the topical composition is administered immediately following the injection of the filler. In one feature, the topical composition is administered at least 1 day following the injection of the filler. In one feature, the topical composition is administered at least 1 week following the injection of the filler. In one feature, the topical composition is administered at least 2 weeks following the injection of the filler. In one feature, the cosmetic procedure is an injection of a neurotoxin. In one feature, the cosmetic procedure is an invasive surgery. In one feature, the topical composition is administered following a medical procedure. In one feature, the topical composition is administered prior to a medical procedure. In one feature, the medical procedure is a therapeutic injection. In one feature, the medical procedure is an intravenous injection. In one feature, the medical procedure is an invasive surgery. In one feature, the topical composition is administered following a trauma. In one feature, the topical composition is administered prior to a trauma. In one feature, the topical composition is administered 1, 2, 3, 4, 5, 6, 7, or 8 times a day. In one feature, the topical composition is administered 4 times a day. In one feature, the individual is a human.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 11A-1B show schematics for preparation of liposomes.

FIG. 16F shows images of a fibrillin stain (10× magnification) in brown demonstrating regeneration of elastin fibers. The left panel is pretreatment and the right panel is 2 weeks after use of the topical product.

FIG. 17 shows results from the Antimicrobial Effectiveness Test of the topical product.

DETAILED DESCRIPTION

Definitions

Figure 1A:
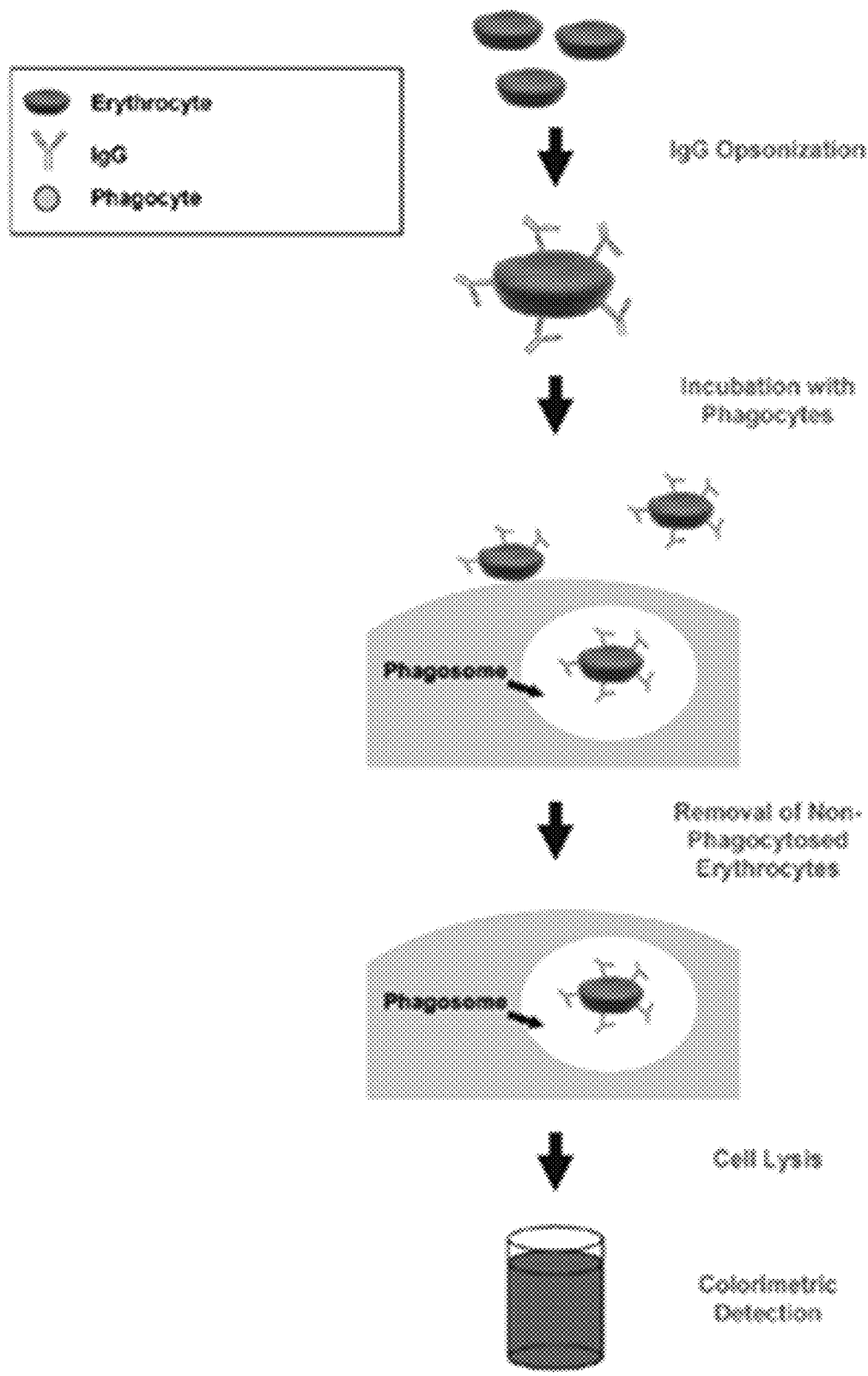
FIG. 1A illustrates a schematic of a macrophage phagocytosis assay.

Throughout this disclosure, various embodiments are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the disclosure, subject to any specifically excluded limit in the stated range. Where the stated range includes one or both of the limits, ranges excluding either or both of those included limits are also included in the disclosure, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

Compositions

A bruise is caused by bleeding under the skin due to trauma to capillaries under the skin. As a result of the trauma, there can be an extravasation of blood to the surrounding tissue. Generally, bruising results in a visible discoloration on the skin. The discoloration caused by bruising can take days to disappear and is resolved through the function of macrophages. Accordingly, compositions are needed for improving the bruising process.

Described herein are compositions and methods for improving bruising. Compositions and methods as described herein can improve bruising by improving macrophage function. Compositions and methods as described herein may further stimulate elastin and/or collagen production, intrinsic hyaluronic acid production, adipogenesis, or reduce inflammation.

Liposomes

Described herein are liposomal compositions for improved distribution, efficacy, bioavailability, and/or activity. Liposomal compositions may improve distribution, efficacy, bioavailability, and/or activity of the active ingredient by improving delivery and tissue (e.g. skin) penetration. In some instances, improved delivery and skin penetration result from the active ingredient being incorporated (e.g. encapsulated) in a liposome. In some instances, the active ingredient is a peptide that is encapsulated in a liposome.

Liposomal compositions as described herein may comprise a peptide encapsulated in a liposome. In some embodiments, the peptide is tripeptide-1. In some embodiments, the peptide is hexapeptide-12. In some embodiments, the peptide is hexapeptide-11 In some embodiments, the peptide is hexapeptide-38. In some embodiments, the peptide is tetrapeptide-2. In some embodiments, the peptide is functionalized with a palmitoyl group. In some embodiments, the peptide is functionalized with an acetyl group. For example, the peptide is acetyl hexapeptide-38.

Liposomal compositions as described herein may comprise various ingredients encapsulated in a liposome. In some embodiments, the ingredient is lactoferrin. In some embodiments, the ingredient is phosphatidylserine. In some embodiments, the ingredient is *Ledum Palustre* extract. In some embodiments, the ingredient is *Arnica Montana* extract. In some embodiments, the ingredient is sodium hyaluronate. In some embodiments, the ingredient is larger than 50 kDa.

Lecithin and other phospholipids may be used to prepare liposomes containing the peptide compositions as described herein. In some embodiments, liposomes are used to prepare one or more peptides. In some embodiments, the peptide is functionalized with an acetyl group. Formation of lipid vesicles occurs when phospholipids such as lecithin are placed in water and consequently form one bilayer or a series of bilayers, each separated by water molecules, once enough energy is supplied. Liposomes can be created by sonicating phospholipids in water. Low shear rates create multilamellar liposomes. Continued high-shear sonication tends to form smaller unilamellar liposomes. Hydrophobic chemicals can be dissolved into the phospholipid bilayer membrane. The lipid bilayers of the liposomes deliver the peptide compositions as described herein.

The phospholipids used to prepare the liposomal compositions described herein may comprise a transition phase temperature of about 10° C. to about 25° C. In some instances, the phospholipids comprise a transition phase temperature of about 10° C., 12° C., 14° C., 16° C., 18° C., 20° C., 22° C., 24° C., 26° C., 28° C., 30° C., 32° C., 34° C., 36° C., 38° C., 40° C., or more than 40° C. In some instances, the phospholipids comprise a transition phase temperature in a range of about 10° C. to about 40° C., about 12° C. to about 36° C., about 14° C. to about 32° C., about 16° C. to about 20° C., or about 21° C. to about 25° C.

The topical composition may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting composition contains micelles, i.e., spherical oil droplets.

The liposomal composition may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting formulation contains micelles, i.e., spherical oil droplets surrounded by a membrane of polar surfactant molecules, dispersed in the aqueous solvent.

Described herein, in some embodiments, are methods for preparing a composition comprising a peptide encapsulated in a liposome, comprising: combining the peptide and a solvent to form a mixture; and contacting the mixture with an aqueous solution comprising liposomes. In some instances, the contacting occurs at a temperature between about 10° C. and about 25° C. In some instances, the contacting occurs at a temperature of about 10° C., 12° C., 14° C., 16° C., 18° C., 20° C., 22° C., 24° C., 26° C., 28° C., 30° C., 32° C., 34° C., 36° C., 38° C., 40° C., or more than 40° C. In some instances, the contacting occurs at a temperature in a range of about 10° C. to about 40° C., about 12° C. to about 36° C., about 14° C. to about 32° C., about 16° C. to about 20° C., or about 21° C. to about 25° C.

Methods for preparing a composition comprising a peptide encapsulated in a liposome may comprise use of a solvent. In some instances, the solvent is water. In some instances, the solvent is an organic solvent. Exemplary organic solvents include, but are not limited to, petroleum ether, cyclohexane, toluene, carbon tetrachloride, dichloromethane, chloroform, diethyl ether, diisopropyl ether, ethyl acetate, butanol, n-propanol, ethanol, methanol, polyethylene glycol, propylene glycol, and pyridine. In some instances, the solvent is a glycol. In some instances, the solvent is butylene glycol. In some instances, the solvent is caprylyl glycol. In some instances, the solvent is propanediol (propylene glycol).

The solvent may be used at various percentages. In some instances, the solvent is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10%. The solvent may be propanediol, butylene glycol, or caprylyl glycol.

Methods as described herein, in some embodiments, comprises combining the peptide and a solvent to form a mixture; and contacting the mixture with an aqueous solution comprising liposomes, wherein the aqueous solution comprises a percentage of water and a percentage of liposomes. In some instances, the aqueous solution comprises at least or about 20%, 30%, 40%, 50%, 60%, 70%, 80%, 90%, or more than 90% water. In some instances, the aqueous solution comprises water in a range of about 10% to about 95%, about 20% to about 90%, about 30% to about 85%, about 40% to about 80%, or about 50% to about 60%. In some instances, the aqueous solution comprises at least or about 20%, 30%, 40%, 50%, 60%, or more than 60% liposomes. In some instances, the aqueous solution comprises liposomes in a range of about 10% to about 80%, about 20% to about 70%, or about 30% to about 60%. A ratio of liposomes to water may be in a range of about 1:9 to about 3:7. In some instances, the ratio of liposomes to water may be at least or about 1:10, 1:9, 1:8, 1:7, 1:6, 1:5, 1:4, 1:3, or 1:2.

Methods for generation of liposomal compositions as described herein may result in an entrapment efficacy of no more than 100%. In some instances, the entrapment efficacy is no more than 50%, 60%, 70%, 80%, 90%, 95%, 99%, or 99.5%.

Described herein are liposomal compositions, wherein the peptide comprises a percentage of the composition. In some embodiments, the peptide is provided at least or about 0.0001%, 0.0005%, 0.00055%, 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5% 4.0%, 4.5% 5.0%, 5.5%, 6.0%, 6.5%, 7.0%, 8%, 9%, 10%, or more than 10% of the composition. In some embodiments, the peptide is provided at least or about 10%, 11%, 12%, 13%, 14%, 15%, 16%, 17%, 18%, 19%, 20%, 22%, 24%, 26%, 28%, 30% or more than 30% of the composition. In some embodiments, the peptide is provided in a range of about 0.001% to about 6%, about 0.002% to about 4%, about 0.01% to about 5%, or about 0.02% to about 2% by weight. In some embodiments, the peptide is provided at about 0.03% of the composition.

Described herein are liposomal compositions, wherein the liposomes comprise a percentage of the composition. In some embodiments, the liposomes are provided at least or about 10%, 11%, 12%, 13%, 14%, 15%, 16%, 17%, 18%, 19%, 20%, 22%, 24%, 26%, 28%, 30% or more than 30% of the composition. In some embodiments, the liposomes are provided in a range of about 5% to about 90%, about 10% to about 80%, about 20% to about 70%, about 30% to about 60%, about 10% to about 30%, or about 20% to about 40%. In some embodiments, the liposomes are provided at about 30%. In some embodiments, the liposomes are provided at 27%.

Liposomal compositions as described herein, in some embodiments, comprise an average particle size of at most 220 nanometers (nm). In some instances, the average particle size is at most 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 230 nm, 240 nm, 250 nm, 260 nm, 270 nm, 280 nm, 290 nm, 300 nm, 320 nm, 340 nm, 360 nm, 380 nm, or 400 nm. In some instances, the average particle size is about 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, 200 nm, 205 nm, 210 nm, 215 nm, 220 nm, 230 nm, 240 nm, 250 nm, 260 nm, 270 nm, 280 nm, 290 nm, 300 nm, 320 nm, 340 nm, 360 nm, 380 nm, or 400 nm. In some instances, the average particle size is in a range of about 50 nm to about 500 nm, about 100 nm to about 400 nm, about 150 nm to about 220 nm, about 180 nm to about 220 nm, or about 190 nm to about 210 nm.

In some instances, the liposomal compositions comprise an active agent that has a molecular weight of no more than about 600 Daltons (Da). In some instances, the active agent has a molecular weight of at least or about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, or more than 1000 Daltons (Da). In some instances, the active agent has a molecular weight of at least or about 1000, 1100, 1200, 1300, 1400, 1500, 1600, 1700, 1800, 1900, 2000, 2100, 2200, 2300, 2400, 2500, 2600, 2700, 2800, 2900, 3000, 4000, 5000, 6000, or more than 6000 Daltons (Da). In some instances, the active agent has a molecular weight in a range of about 50 to about 1000, about 100 to about 900, about 200 to about 800, about 300 to about 700, or about 400 to about 600 Daltons (Da). In some instances, the active agent is a peptide. In some instances, the active agent is a peptide encapsulated in a liposome.

A polydispersity index (PdI) of a liposomal composition as described herein, in some embodiments, is in a range of 0 to about 0.2. In some instances, the polydispersity index is about 0.01, 0.025, 0.05, 0.1, 0.25, 0.3, 0.35, 0.4, 0.45, 0.5, 0.55, 0.6, 0.65, 0.7, 0.75, or 0.8. In some instances, the polydispersity index is in a range of about 0.01 to about 0.8, about 0.025 to about 0.75, about 0.05 to about 0.6, or about 0.1 to about 0.3.

In some instances, an intercept of a liposomal composition as described herein is in a range of about 0.85 to about 0.95. In some instances, the intercept is the amplitude. In some instances, the intercept is at least or about 0.65, 0.70, 0.75, 0.80, 0.85, 0.90, or 0.95.

In some embodiments, the liposomes comprise propanediol, lecithin, or a combination thereof. In some embodiments, the propanediol is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the propanediol is provided in a range of about 0.001% to about 6%, about 0.002% to about 4%, about 0.01% to about 3%, or about 0.02% to about 2% by weight. In some embodiments, the lecithin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the lecithin is provided in a range of about 0.001% to about 6%, about 0.002% to about 4%, about 0.01% to about 3%, or about 0.02% to about 2% by weight. In some embodiments, the liposomes comprise propanediol and lecithin. In some embodiments, the propanediol and lecithin are provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the propanediol and lecithin are provided in a range of about 0.001% to about 6%, about 0.002% to about 4%, about 0.01% to about 3%, or about 0.02% to about 2% by weight. In some embodiments, the propanediol and lecithin are provided at about 0.90% by weight Described herein are liposomal compositions comprising improved distribution, efficacy, bioavailability, and/or activity. The liposomal compositions may comprise improved distribution, efficacy, bioavailability, and/or activity as compared to compositions not comprising liposomes. In some instances, the distribution is improved by at least or about 0.5×, 1.0×, 1.5×, 2.0×, 2.5×, 3.0×, 4.0×, 4.5×, 5×, or more than 5× as compared to compositions not comprising liposomes. In some instances, the efficacy is improved by at least or about 0.5×, 1.0×, 1.5×, 2.0×, 2.5×, 3.0×, 4.0×, 4.5×, 5×, or more than 5× as compared to compositions not comprising liposomes. In some instances, the bioavailability is improved by at least or about 0.5×, 1.0×, 1.5×, 2.0×, 2.5×, 3.0×, 4.0×, 4.5×, 5×, or more than 5× as compared to compositions not comprising liposomes. In some instances, the activity is improved by at least or about 0.5×, 1.0×, 1.5×, 2.0×, 2.5×, 3.0×, 4.0×, 4.5×, 5×, or more than 5× as compared to compositions not comprising liposomes. The distribution, efficacy, bioavailability, and/or activity may be improved by at least or about 10%, 15%, 20%, 25%, 30%, 35%, 40%, 45%, 50%, 55%, 60%, 65%, 70%, 75%, 80%, 85%, 90%, or more than 90% as compared to compositions not comprising liposomes.

Liposomal compositions and methods as described herein, in some embodiments, are topical compositions. In some instances, the liposomal compositions are oil free. In some instances, the liposomal compositions are preservative free. In some embodiments, the liposomal formulation is an aqueous formulation. In some embodiments, the liposomal formulation is an anhydrous formulation. In some instances, the liposomal composition comprises a pH in a range of about 5 to about 8. In some instances, the liposomal composition comprises a pH of at least or about 2, 3, 4, 5, 6, 7, 8, 9, or 10.

Methods and compositions as described herein may result in improved follicular penetration. In some instances, the follicular penetration is improved by at least or about 0.5×, 1.0×, 1.5×, 2.0×, 2.5×, 3.0×, 4.0×, 4.5×, 5×, or more than 5×. The follicular penetration may be improved by at least or about 10%, 15%, 20%, 25%, 30%, 35%, 40%, 45%, 50%, 55%, 60%, 65%, 70%, 75%, 80%, 85%, 90%, or more than 90%. In some instances, compositions result in follicular penetration of a depth of at least or about 0.5, 0.75, 1, 1.25, 1.5, 2, 2.5, 3, 3.5, 4, 4.5, 5, 5.5, 6, 7, 8, 9, 10, or more than 10 millimeters.

Peptides

Peptides as described herein, in some embodiments, improve bruising, elastin and/or collagen simulation, hyaluronic acid stimulation, adipocyte stimulation, reduce inflammation, or combinations thereof. In some embodiments, peptides as described herein improve macrophage function. In some embodiments, tripeptide-1 results in elastin and/or collagen stimulation, extracellular matrix (ECM) recycling, anti-inflammatory effects, or combinations thereof. In some embodiments, hexapeptide-12 draws in newly produced elastin. In some embodiments, acetyl tetrapeptide-2 stimulates fibroblasts to produce elastin.

Peptides as described herein, in some embodiments, in combination improve bruising, elastin and/or collagen simulation, hyaluronic acid stimulation, adipocyte stimulation, reduce inflammation, or combinations thereof. For example, tripeptide-1 and hexapeptide-12 improve macrophage function. In some embodiments, tripeptide-1 and hexapeptide-11 improve macrophage function. In some embodiments, tripeptide-1, hexapeptide-11, and hexapeptide-12 improve macrophage function. For example, hexapeptide-11 in combination with one or more different peptides such as tripeptide-1, hexapeptide-12, or a combination thereof is a potent stimulator of autophagy and macrophage clustering and can improve removal of hemosiderin pigment associated with bruising and bleeding.

Compositions as described herein comprise a varying concentration of peptide. In some instances, a peptide is present at about 50 ppm or less to 1000, 5000, 10000, 50000, 100000, 500000 ppm or more, e.g., 100 ppm of the peptide. In some instances, a peptide is present at about 1, 2, 3, 4, 5, 6, 7, 8, 9, 10, 15, 20, 25, 50, 75, 100, 200, 300, 400, 500, 600, 700, 800, 900, 1000, or more than 1000 ppm. In some instances, a peptide is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 ppm. In some instances, a peptide is present at about 1, 2, 3, 4, 5, 6, 7, 8, 9, 10, 15, 20, 25, 50, 75, 100, 200, 300, 400, 500, 600, 700, 800, 900, 1000, or more than 1000 microgram per milliliter (ug/mL). In some instances, a peptide is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 microgram per milliliter. In some instances, a peptide is present from about 0.01% to about 10%, about 0.01% to about 0.02%, about 0.01% to about 0.03%, about 0.01% to about 0.04%, about 0.01% to about 0.05%, about 0.01% to about 0.1%, about 1% to about 5%, or about 1% to about 10% by weight (wt. %).

Compositions as described herein, in some embodiments, comprise a plurality of peptides. In some instances, a peptide of the plurality of peptides is present at about 50 ppm or less to 1000, 5000, 10000, 50000, 100000, 500000 ppm or more, e.g., 100 ppm of the peptide, or any other suitable amount. In some instances, a peptide of the plurality of peptides is present at about 1, 2, 3, 4, 5, 6, 7, 8, 9, 10, 15, 20, 25, 50, 75, 100, 200, 300, 400, 500, 600, 700, 800, 900, 1000, or more than 1000 ppm. In some instances, a peptide of the plurality of peptides is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 ppm. In some instances, a peptide of the plurality of peptides is present at about 1, 2, 3, 4, 5, 6, 7, 8, 9, 10, 15, 20, 25, 50, 75, 100, 200, 300, 400, 500, 600, 700, 800, 900, 1000, or more than 1000 microgram per milliliter (ug/mL). In some instances, a peptide of the plurality of peptides is present in a range of about 1 to about 100, about 1 to about 50, about 1 to about 40, about 1 to about 30, about 1 to about 20, about 1 to about 10, about 5 to about 90, about 10 to about 80, about 20 to about 60, or about 30 to about 50 microgram per milliliter. In some instances, a peptide of the plurality of peptides is present from about 0.01% to about 10%, about 0.01% to about 0.02%, about 0.01% to about 0.03%, about 0.01% to about 0.04%, about 0.01% to about 0.05%, about 0.01% to about 0.1%, about 1% to about 5%, or about 1% to about 10% by weight (wt. %). In some embodiments, a peptide of the plurality of peptides is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, a peptide of the plurality of peptides is provided in a range of about 0.25% to about 10%, about 0.5% to about 8%, about 0.75% to about 6%, or about 1% to about 4% by weight. In some embodiments, each peptide of the plurality of peptides is provided in a range of about 0.001% to about 6%, about 0.002% to about 4%, about 0.01% to about 3%, or about 0.02% to about 2% by weight.

In some embodiments, the peptide is tripeptide-1, hexapeptide-12, hexapeptide-11, hexapeptide-38, tetrapeptide-2, or combinations thereof.

In some embodiments, the tripeptide-1 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the tripeptide-1 is provided in a range of about 0.25% to about 10%, about 0.5% to about 8%, about 0.75% to about 6%, or about 1% to about 4% by weight. In some embodiments, the tripeptide-1 is provided at least or about 0.25, 0.5, 0.75, 1, 1.5, 2, 2.5, 3, 3.5, 4, 5, 6, 7, 8, 9, 10, 15, 20, 25, or more than 25 ppm. In some embodiments, the tripeptide-1 is provided in a range of about 0.25 to about 10, about 0.5 to about 8, about 1 to about 6, or about 2 to about 4 ppm. In some embodiments, the tripeptide-1 is provided in a range of about 1 to about 10 ppm. In some embodiments, the tripeptide-1 is provided at least or about 0.25, 0.5, 0.75, 1, 1.5, 2, 2.5, 3, 3.5, 4, 5, 6, 7, 8, 9, 10, 15, 20, 25, or more than 25 microgram per milliliter (ug/mL). In some embodiments, the tripeptide-1 is provided in a range of about 0.25 to about 10, about 0.5 to about 8, about 1 to about 6, or about 2 to about 4 microgram per milliliter.

In some embodiments, the hexapeptide-12 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the hexapeptide-12 is provided in a range of about 0.25% to about 10%, about 0.5% to about 8%, about 0.75% to about 6%, or about 1% to about 4% by weight. In some embodiments, the hexapeptide-12 is provided at least or about 0.25, 0.5, 0.75, 1, 1.5, 2, 2.5, 3, 3.5, 4, 5, 6, 7, 8, 9, 10, 15, 20, 25, or more than 25 ppm. In some embodiments, the hexapeptide-12 is provided in a range of about 1 to about 10 ppm. In some embodiments, the hexapeptide-12 is provided in a range of about 0.25 to about 10, about 0.5 to about 8, about 1 to about 6, or about 2 to about 4 ppm. In some embodiments, the hexapeptide-12 is provided at least or about 0.25, 0.5, 0.75, 1, 1.5, 2, 2.5, 3, 3.5, 4, 5, 6, 7, 8, 9, 10, 15, 20, 25, or more than 25 microgram per milliliter (ug/mL). In some embodiments, the hexapeptide-12 is provided in a range of about 0.25 to about 10, about 0.5 to about 8, about 1 to about 6, or about 2 to about 4 microgram per milliliter.

In some embodiments, the hexapeptide-11 is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%1, 1.5%, 2.0%, 2.5%, 3.0%, 3.5%, 4.0%, 4.5%, 5.0%, 5.5%, 6.0%, 6.5%, 7.0%, 8%, 9%, 10%, 20%, 30%, 40%, 50%, 60%, 70%, 80%, 90% or more than 90% by weight (wt. %). In some embodiments, the hexapeptide-11 is provided in a range of about 0.25% to about 10%, about 0.5% to about 8%, about 0.75% to about 6%, or about 1% to about 4% by weight. In some embodiments, the hexapeptide-11 is provided in a range of about 0.001% to about 6%, about 0.002% to about 4%, about 0.01% to about 3%, or about 0.02% to about 2%. In some embodiments, the hexapeptide-11 is provided in a range of about 0.005% to about 0.02% by weight. In some embodiments, the hexapeptide-11 is provided at least or about 5, 10, 20, 25, 50, 75, 100, 150, 200, 250, or more than 250 ppm. In some embodiments, the hexapeptide-11 is provided in a range of about 25 to about 250, about 50 to about 200, or about 75 to about 150 ppm. In some embodiments, the hexapeptide-11 is provided in a range of about 10 to about 100 ppm. In some embodiments, the hexapeptide-11 is provided at least or about 5, 10, 20, 25, 50, 75, 100, 150, 200, 250, or more than 250 microgram per milliliter (ug/mL). In some embodiments, the hexapeptide-11 is provided in a range of about 25 to about 250, about 50 to about 200, or about 75 to about 150 microgram per milliliter.

In some embodiments, the hexapeptide-38 is provided at least or about 0.00001%, 0.0003%, 0.0005%, 0.001%, 0.001%, 0.005%, 0.0055%, 0.01%, 0.02%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, 20%, 30%, 40%, 50%, 60%, 70%, 80%, 90% or more than 90% by weight (wt. %). In some embodiments, the hexapeptide-38 is provided in a range of about 0.25% to about 10%, about 0.5% to about 8%, about 0.75% to about 6%, or about 1% to about 4% by weight. In some embodiments, the hexapeptide-38 is provided in a range of about 0.001% to about 6%, about 0.002% to about 4%, about 0.01% to about 3%, or about 0.02% to about 2%. In some embodiments, the hexapeptide-38 is provided in a range of about 0.005% to about 0.02% by weight. In some embodiments, the hexapeptide-38 is provided at least or about 0.25, 0.5, 0.75, 1, 1.5, 2, 2.5, 3, 3.5, 4, 5, 10, 20, 25, 50, 75, 100, 150, 200, 250, or more than 250 ppm. In some embodiments, the hexapeptide-38 is provided in a range of about 25 to about 250, about 50 to about 200, or about 75 to about 150 ppm. In some embodiments, the hexapeptide-38 is provided at least or about 5, 10, 20, 25, 50, 75, 100, 150, 200, 250, or more than 250 microgram per milliliter (ug/mL). In some embodiments, the hexapeptide-38 is provided in a range of about 25 to about 250, about 50 to about 200, or about 75 to about 150 microgram per milliliter. In some embodiments, the hexapeptide-38 is acetyl hexapeptide-38.

In some embodiments, the tetrapeptide-2 is provided at least or about 0.00001%, 0.0003%, 0.0005%, 0.001%, 0.001%, 0.005%, 0.0055%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the tetrapeptide-2 is provided in a range of about 0.25% to about 10%, about 0.5% to about 8%, about 0.75% to about 6%, or about 1% to about 4% by weight. In some embodiments, the tetrapeptide-2 is provided at least or about 0.25, 0.5, 0.75, 1, 1.5, 2, 2.5, 3, 3.5, 4, 5, 6, 7, 8, 9, 10, 15, 20, 25, or more than 25 ppm. In some embodiments, the tetrapeptide-2 is provided in a range of about 0.25 to about 10, about 0.5 to about 8, about 1 to about 6, or about 2 to about 4 ppm. In some embodiments, the tetrapeptide-2 is provided at least or about 0.25, 0.5, 0.75, 1, 1.5, 2, 2.5, 3, 3.5, 4, 5, 6, 7, 8, 9, 10, 15, 20, 25, or more than 25 microgram per milliliter (ug/mL). In some embodiments, the tetrapeptide-2 is provided in a range of about 0.25 to about 10, about 0.5 to about 8, about 1 to about 6, or about 2 to about 4 microgram per milliliter.

In example embodiments, a weight ratio for the first peptide to the second peptide in a topical composition is 1 part first peptide to 0.2 to 10 parts second peptide, 1 to 10 parts second peptide, 1 to 8 parts second peptide, or 1 to 5.5 parts second peptide. The following nomenclature is employed herein to refer to various amino acids: Alanine (also referred to herein as "Ala" or "A"), Arginine (also referred to herein as "Arg" or "R"), Asparagine (also referred to herein as "Asn" or "N"), Aspartic acid (also referred to herein as "Asp" or "D"), Cysteine (also referred to herein as "Cys" or "C"), Glutamic acid (also referred to herein as "Glu" or "E"), Glutamine (also referred to herein as "Gln" or "Q"), Glycine (also referred to herein as "Gly" or "G"), Histidine (also referred to herein as "His" or "H"), Isoleucine (also referred to herein as "Ile" or "I"), Leucine (also referred to herein as "Leu" or "L"), Lysine (also referred to herein as "Lys" or "K"), Methionine (also referred to herein as "Met" or "M"), Phenylalanine (also referred to herein as "Phe" or "F"), Proline (also referred to herein as "Pro" or "P"), Serine (also referred to herein as "Ser" or "S"), Threonine (also referred to herein as "Thr" or "T"), Tryptophan (also referred to herein as "Trp" or "W"), Tyrosine (also referred to herein as "Tyr" or "Y"), Valine (also referred to herein as "Val" or "V").

In some embodiments, the first peptide is a dipeptide. Suitable dipeptides include but are not limited to those having the following sequence of amino acids: KK, KP, CK, KC, KT, DF, NF, VW, YR, or TT. In some embodiments, the dipeptide has the following amino acid sequence: KV. In other embodiments, the first peptide is a tripeptide. Suitable tripeptides include but are not limited to those having the following sequence of amino acids: HGG, RKR, GHK, GKH, GGH, GHG, KFK, or KPK. In some embodiments, the tripeptide has the following amino acid sequence: KVK. In some embodiments, the first peptide is a tetrapeptide. Suitable tetrapeptides include but are not limited to those having the following sequence of amino acids: GQPR, KTFK, AQTR, or RSRK. In some embodiments, the tetrapeptide has the following sequence of amino acids: KDVY. In some embodiments, the second peptide is a pentapeptide. Suitable pentapeptides include but are not limited to those having the following sequence of amino acids: KTTKS, YGGFX, or KLAAK. In some embodiments, the second peptide is a hexapeptide. Suitable hexapeptides include but are not limited to those having the following sequence of amino acids: VGVAPG or GKTTKS. In some embodiments, the hexapeptide has the following sequence of amino acids: FVAPFP. In some embodiments, the second peptide is a heptapeptide. Suitable heptapeptides include but are not limited to one having an amino acid sequence RGYYLLE, or Heptapeptide-6 (a pro-sirtuin peptide). The compositions may include two or more peptides, e.g., two dipeptides and one pentapeptide; one tripeptide and one hexapeptide; one dipeptide, one tripeptide, and one heptapeptide, or the like, provided that the composition contains at least one dipeptide, tripeptide, or tetrapeptide and at least one pentapeptide, hexapeptide, or heptapeptide. In some embodiments, the compositions comprise a tripeptide and one or more hexapeptides. In some embodiments, the compositions comprise a tripeptide, one or more hexapeptides, and a tetrapeptide. In some embodiments, the tripeptide is tripeptide-1. In some embodiments, the one or more hexapeptide is hexapeptide-12. In some embodiments, the one or more hexapeptide is hexapeptide-11. In some embodiments, the one or more hexapeptide is hexapeptide-38. In some embodiments, the compositions comprise tripeptide-1, hexapeptide-12, hexapeptide-11, and hexapeptide-38. In some embodiments, the tetrapeptide is tetrapeptide-2.

The peptide can be functionalized. For example, the peptide can be functionalized with a fatty acid, e.g., myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, or the like. Examples include palmitoyl hexapeptide-12 (Pal-VGVAPG), palmitoyl tripeptide-1 (Pal-GHK), myristoyl hexapeptide-12 (Myr-VGVAPG), and myristoyl tripeptide-1 (Myr-GHK). Palmitoyl or myristoyl functionalization can be desirable in certain embodiments as it exhibits enhanced penetration when compared to other fatty acids. In some embodiments, the peptide is functionalized with a chemical group. For example, the peptide is functionalized with acetyl. Examples include acetyl hexapeptide-38 and acetyl tetrapeptide-2. In some instances, the peptide is functionalized with a functional group comprising no more than 14 carbons. In some instances, the peptide is functionalized with a functional group comprising no more than 3, 4, 5, 6, 7, 8, 9, 10, 11, 12, 13, 14, 15, 16, 17, 18, 19, 20, or more than 20 carbons. In some instances, the peptide is non-palmitoylated. Without wishing to be limited to a particular theory, incorporation of the peptide in a liposome, in some embodiments, increases the lipophilicity of a peptide that is functionalized or is not functionalized.

Some embodiments of the methods and compositions provided herein include as a first peptide glycine-histidine-lysine (GHK). GHK is a peptide sequence that is rarely found in the class of proteins in general, but is frequently found in extracellular matrix proteins. The small size of GHK permits it to approach membrane receptors far more easily than larger peptides. Further, its unique, copper-binding structure enhances copper transport into and out of cells and promotes wound healing through several different but related pathways. Due to its strong copper binding structure, GHK can be provided in the form of GHK-Cu (copper-bound GHK form).

In compositions, the tripeptide is typically present in an amount of from about 50 ppm or less to about 100, 200, 300, 400, or 500 ppm or more, e.g., 50 ppm to 150 ppm.

In compositions, the hexapeptide is typically present in an amount of from about 50 ppm or less to about 100, 200, 300, 400, or 500 ppm or more, e.g., 50 ppm to 150 ppm.

In compositions, the tetrapeptide is typically present in an amount of from about 50 ppm or less to about 100, 200, 300, 400, or 500 ppm or more, e.g., 50 ppm to 150 ppm.

The peptides can advantageously be provided in a base for suitable for combining with other components of a liposomal composition. The base can include one or more components such as a thickener/binding agent (e.g., pentaerythrityl tetraisostearate), an emollient/dispersing agent (e.g., caprylic/capric triglyceride), a solvent (e.g., propylene carbonate), and/or a rheology modifier/antisettling agent (e.g., disteardimonium hectorite).

Phosphatidylserine

Compositions as described herein, in some embodiments, comprise phosphatidylserine. Exposure of phosphatidylserine from the inner cell membrane of red blood cells can induce phagocytosis of red blood cells. See Chang C F, Goods B A, Askenase M H, et al. Erythrocyte efferocytosis modulates macrophages towards recovery after intracerebral hemorrhage. *The Journal of clinical investigation*. 2018; 128(2):607-624.

In some embodiments, phosphatidylserine is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the phosphatidylserine is provided in a range of about 0.25% to about 10%, about 0.5% to about 8%, about 0.75% to about 6%, or about 1% to about 4% by weight. In some embodiments, the phosphatidylserine is provided in a range of about 0.001% to about 6%, about 0.002% to about 4%, about 0.005% to about 0.1%. about 0.01% to about 3%, or about 0.02% to about 2% by weight. In some embodiments, the phosphatidylserine is provided in a range of about 0.005% to about 0.02% by weight. In some embodiments, the phosphatidylserine is provided at about 0.05% by weight. In some embodiments, the phosphatidylserine is provided at about 0.25% by weight. In some embodiments, the phosphatidylserine is provided at about 1% by weight. In some embodiments, the phosphatidylserine is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, the phosphatidylserine is provided in a range of about 5 to about 1000, about 10 to about 900, about 30 to about 800, about 50 to about 700, about 60 to about 600, or about 100 to about 500 microgram per milliliter (ug/mL).

*Arnica montana* Extract

Compositions as described herein, in some embodiments, comprise an anti-inflammatory agent. Exemplary anti-inflammatory agents include, but are not limited to, *Arnica montana* extract. *Arnica montana* extract includes components such as essential oils, fatty acids, thymol, pseudoguaianolide sesquiterpene lactones, flavanone glycosides, flavonoids, and coumarins. It can exhibit an anti-inflammatory effect. In some instances, *Arnica montana* extract accelerates healing, reduces bruising potential, modulates inflammation, and stimulates granular tissue and accelerates healing, or combinations thereof. See Rajasingh J, Marzotto M, Bonafini C, et al. *Arnica montana* Stimulates Extracellular Matrix Gene Expression in a Macrophage Cell Line Differentiated to Wound-Healing Phenotype. *PloS one*. 2016; 11(11). In some instances, *Arnica montana* improves bruising by decreasing the inflammation associated with blood products. In some instances, *Arnica montana* stimulates the function of M2 macrophages and improves wound healing. See Rajasingh J, Marzotto M, Bonafini C, et al. *Arnica montana* Stimulates Extracellular Matrix Gene Expression in a Macrophage Cell Line Differentiated to Wound-Healing Phenotype. *PloS one*. 2016; 11(11).

In some embodiments, *Arnica montana* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 5%, 6%, 7%, 8%, 9%, 10%, or more than 10% by weight (wt. %). In some embodiments, the *Arnica montana* extract is provided in a range of about 0.25% to about 10%, about 0.5% to about 8%, about 0.75% to about 6%, or about 1% to about 4% by weight. In some embodiments, the *Arnica montana* extract is provided in a range of about 0.001% to about 6%, about 0.002% to about 4%, about 0.01% to about 3%, about 0.02% to about 2% by weight, or about 0.1% to about 2.5%.

*Ledum Palustre*

Compositions as described herein, in some embodiments, comprise *Ledum palustre* extract. *Ledum palustre* is also known as marsh tea, wild rosemary, or labrador tea. *Ledum palustre* has been used for insect bites, puncture wounds, and cold swellings or bruises. See Kang J Y, Tran K D, Seiff S R, Mack W P, Lee W W. Assessing the Effectiveness of *Arnica montana* and *Rhododendron tomentosum* (*Ledum palustre*) in the Reduction of Ecchymosis and Edema After Oculofacial Surgery: Preliminary Results. *Ophthalmic Plast Reconstr Surg*. 2017; 33(1):47-52.

In some embodiments, *Ledum palustre* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the *Ledum palustre* extract is provided in a range of about 0.25% to about 10%, about 0.5% to about 8%, about 0.75% to about 6%, or about 1% to about 4% by weight. In some embodiments, the *Ledum palustre* extract is provided in a range of about 0.001% to about 6%, about 0.002% to about 4%, about 0.01% to about 3%, about 0.02% to about 2% by weight, or about 0.1% to about 2.5%. In some embodiments, the *Ledum palustre* extract is provided at about 0.25%. In some embodiments, the *Ledum palustre* extract is provided at about 0.5%. In some embodiments, the *Ledum palustre* extract is provided at about 1.0%.

*Leuconostoc* Radish Root Ferment Filtrate

Compositions as described herein, in some embodiments, comprise *Leuconostoc*/radish root ferment filtrate. In some embodiments, the *Leuconostoc*/radish root ferment filtrate is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the *Leuconostoc*/radish root ferment filtrate is provided in a range of about 0.25% to about 10%, about 0.5% to about 8%, about 0.75% to about 6%, or about 1% to about 4% by weight. In some embodiments, the *Leuconostoc*/radish root ferment filtrate is provided in a range of about 0.001% to about 6%, about 0.002% to about 4%, about 0.01% to about 3%, about 0.02% to about 2% by weight, or about 0.1% to about 2.5%. In some embodiments, the *Leuconostoc*/radish root ferment filtrate is provided at about 0.25%. In some embodiments, the *Leu-*

*conostoc*/radish root ferment filtrate is provided at about 0.5%. In some embodiments, the *Leuconostoc*/radish root ferment filtrate is provided at about 1.0%.

Lactoferrin

Compositions as described herein, in some embodiments, comprise a transferrin. In some embodiments, the transferrin is a lactoferrin. In some embodiments, lactoferrin is encapsulated in a liposome. Lactoferrin has wound healing attributes, promotes proliferation of fibroblasts and increases HA secretion. See Saito S, Takayama Y, Mizumachi K, Suzuki C. Lactoferrin promotes hyaluronan synthesis in human dermal fibroblasts. *Biotechnology letters.* 2011; 33(1):33-39; Takayama Y. Effects of Lactoferrin on Skin Wound Healing. In: *Lactoferrin and its Role in Wound Healing.* 2012:87-100.

In some instances, the lactoferrin has antimicrobial activity. In some instances, the lactoferrin has antimicrobial activity against bacteria, fungi, yeasts, viruses, parasites, or combinations thereof. Lactoferrin, in some instances, comprises antibiofilm activity. In some instances, lactoferrin interacts with the bacterial surface and destabilizes the microbial membrane. In some instances, lactoferrin chelates iron to disrupt the microbial membrane.

In some embodiments, lactoferrin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the lactoferrin is provided in a range of about 0.005% to about 0.1%, about 0.25% to about 10%, about 0.5% to about 8%, about 0.75% to about 6%, or about 1% to about 4% by weight. In some embodiments, the lactoferrin is provided in a range of about 0.001% to about 6%, about 0.002% to about 4%, about 0.01% to about 2.5%, or about 0.02% to about 2% by weight. In some embodiments, the lactoferrin is provided at about 0.025%. In some embodiments, the lactoferrin is provided at about 0.05%. In some embodiments, the lactoferrin is provided at about 0.10%. In some embodiments, the lactoferrin is provided at least or about 5, 10, 20, 25, 50, 75, 100, 150, 200, 250, 300, 350, 400, 450, 500, 550, 600, 650, 700, 750, 800, 850, 900, 950, 1000 or more than 1000 microgram per milliliter (ug/mL). In some embodiments, the lactoferrin is provided in a range of about 5 to about 1000, about 10 to about 900, about 30 to about 800, about 50 to about 700, about 60 to about 600, or about 100 to about 500 microgram per milliliter (ug/mL).

Dill Extract

Compositions as described herein, in some embodiments, comprise dill extract. The dill extract, in some embodiments, stimulates LOXL reinduction and elastin formation. In some embodiments, the dill extract is *Anethum graveolens* extract. In some embodiments, the dill extract is *Peucedanum graveolens* extract.

In some embodiments, the dill extract is provided at least or about 0.01%, 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the dill extract is provided in a range of about 0.25% to about 10%, about 0.025% to about 4%, about 0.5% to about 8%, about 0.75% to about 6%, or about 1% to about 4% by weight. In some embodiments, the dill extract is provided at about 1.0% by weight.

Hydroxymethoxyphenyl Decanone

Compositions as described herein, in some embodiments, comprise hydroxymethoxyphenyl decanone. In some embodiments, the hydroxymethoxyphenyl decanone is a potent intrinsic hyaluronic acid booster, antioxidant, anti-irritant, or a combination thereof.

In some embodiments, hydroxymethoxyphenyl decanone is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the hydroxymethoxyphenyl decanone is provided in a range of about 0.25% to about 10%, about 0.1% to about 2.5%, about 0.5% to about 8%, about 0.75% to about 6%, or about 1% to about 4% by weight. In some embodiments, the hydroxymethoxyphenyl decanone is provided in a range of about 0.001% to about 6%, about 0.002% to about 4%, about 0.01% to about 3%, or about 0.02% to about 2% by weight.

*Tremella Fuciformis*

Compositions as described herein, in some embodiments, comprise *Tremella fuciformis* extract. In some embodiments, the *Tremella fuciformis* extract is derived from an edible mushroom. In some embodiments, *Tremella fuciformis* extract provides moisture and antioxidant properties.

In some embodiments, *Tremella fuciformis* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the *Tremella fuciformis* extract is provided in a range of about 0.25% to about 10%, about 0.1% to about 2.5%, about 0.5% to about 8%, about 0.75% to about 6%, or about 1% to about 4% by weight. In some embodiments, the *Tremella fuciformis* extract is provided in a range of about 0.001% to about 6%, about 0.002% to about 4%, about 0.01% to about 3%, or about 0.02% to about 2% by weight.

Sodium Hyaluronate Crosspolymer

Compositions as described herein, in some embodiments, comprise sodium hyaluronate crosspolymer. Sodium hyaluronate crosspolymer is a high molecular weight synthetic hyaluronic acid with high water-binding capacity and moisturizing abilities.

In some embodiments, the sodium hyaluronate crosspolymer is provided at least or about 0.0001%, 0.0005%, 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4.0% by weight (wt. %). In some embodiments, the sodium hyaluronate crosspolymer is provided at about 0.5% by weight. In some embodiments, the sodium hyaluronate crosspolymer is provided in a range of about 0.0001% to about 4.0%, about 0.001% to about 4.0%, about 0.01% to about 3.0%, about 0.1% to about 2.5%, or about 0.50% to about 1.5% by weight.

Phytoene and Phytofluene

Compositions as described herein, in some embodiments, comprise phytoene, phytofluene, or combinations thereof. Phytoene and phytofluene are colorless carotenoids derived from saltwater microalgae that modulate Prostaglandin E-2 (PGE-2).

In some embodiments, the phytoene, phytofluene, or combinations thereof is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the phytoene, phytofluene, or combinations thereof is provided in a range of about 0.25% to about 10%, about 0.1% to about 2.5%, about 0.5% to about 8%, about 0.75% to about 6%, or about 1% to about 4% by weight. In some embodiments, the phytoene, phytofluene, or combinations thereof is provided in a range of about 0.001% to about 6%, about 0.002% to about 4%, about 0.01% to about 3%, or about 0.02% to about 2% by weight.

Xylitol

Compositions as described herein, in some embodiments, comprise xylitylglucoside, anhydroxylitol, xylitol, or combinations thereof. Xylitol is a sugar alcohol and comprises anti-biofilm and anti-inflammatory effects. In some embodiments, xylitol and lactoferrin in combination comprise anti-biofilm effects. In some embodiments, xylitol and lactoferrin act synergistically. For example, lactoferrin destabilizes the bacterial membrane and allows xylitol to cross the bacterial membrane to inhibit biofilm development and growth.

In some embodiments, the xylitylglucoside, anhydroxylitol, xylitol, or combinations thereof is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the xylitylglucoside, anhydroxylitol, xylitol, or combinations thereof is provided in a range of about 0.25% to about 10%, about 0.1% to about 2.5%, about 0.5% to about 8%, about 0.75% to about 6%, or about 1% to about 4% by weight. In some embodiments, the xylitylglucoside, anhydroxylitol, xylitol, or combinations thereof is provided in a range of about 0.001% to about 6%, about 0.002% to about 4%, about 0.01% to about 3%, or about 0.02% to about 2% by weight.

Sorbitan Isostearate

Compositions as described herein, in some embodiments, comprise sorbitan isostearate. In some embodiments, the sorbitan isostearate is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the sorbitan isostearate is provided in a range of about 0.25% to about 10%, about 0.1% to about 2.5%, about 0.5% to about 8%, about 0.75% to about 6%, or about 1% to about 4% by weight. In some embodiments, the sorbitan isostearate is provided in a range of about 0.001% to about 6%, about 0.002% to about 4%, about 0.01% to about 3%, or about 0.02% to about 2% by weight. In some embodiments, the sorbitan isostearate is provided at about 0.10% by weight.

Glucose

In some embodiments, compositions as described herein comprise glucose. In some embodiments, the glucose is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the glucose is provided in a range of about 0.25% to about 10%, about 0.1% to about 2.5%, about 0.5% to about 8%, about 0.75% to about 6%, or about 1% to about 4% by weight. In some embodiments, the glucose is provided in a range of about 0.001% to about 6%, about 0.002% to about 4%, about 0.01% to about 3%, or about 0.02% to about 2% by weight. In some embodiments, the glucose is provided at about 0.01% by weight.

Compositions as described herein, in some embodiments, comprise seed oil. In some embodiments, the seed oil is *Helianthus annuus* (sunflower) seed oil. In some embodiments, the seed oil is provided at least or about 0.001%, 0.003%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the seed oil is provided in a range of about 0.25% to about 10%, about 0.1% to about 2.5%, about 0.5% to about 8%, about 0.75% to about 6%, or about 1% to about 4% by weight. In some embodiments, the seed oil is provided in a range of about 0.001% to about 6%, about 0.002% to about 4%, about 0.01% to about 3%, or about 0.02% to about 2% by weight. In some embodiments, the seed oil is provided at about 0.003% by weight.

Other Components

Other components can include anti-inflammatory agents, antioxidants, and solubility enhancers. Exemplary anti-irritation agents include, but are not limited to, panthenyl triacetate and naringenin. Panthenyl triacetate and naringenin are natural plant extracts that reduce redness and water loss through the skin. Typical amounts for anti-irritation agents when employed in compositions are from 1% by weight to 4% by weight (wt. %).

Exemplary antioxidant agents include, but are not limited to, *Dunaliella salina* extract and squalane. *Dunaliella salina* extract includes components such as beta carotenes. It can exhibit an antioxidant effect. Typical amounts for anti-inflammatory agents when employed in compositions are from 0.1% by weight to 2.5% by weight (wt. %). In some embodiments, the *Dunaliella salina* extract is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight. In some embodiments, the *Dunaliella salina* extract is provided in a range of about 0.001% to about 4.0%, about 0.01% to about 3.0%, about 0.10% to about 2.5%, or about 0.50% to about 1.5%. In some embodiments, the squalane is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight. In some embodiments, the squalane is provided in a range of about 0.001% to about 4.0%, about 0.01% to about 3.0%, about 0.1% to about 2.5%, or about 0.50% to about 1.5%. In some embodiments, the *Dunaliella salina* extract and the squalane is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight. In some embodiments, the *Dunaliella salina* and the squalane extract is provided in a range of about 0.001% to about 4.0%, about 0.01% to about 3.0%, about 0.1% to about 2.5%, or about 0.50% to about 1.5%.

In some embodiments, the composition comprises a siloxane polymer. In some embodiments, the siloxane polymer is caprylyl methicone. In some embodiments, caprylyl methicone is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4.0% by weight (wt. %). In some embodiments, the caprylyl methicone is provided at about 0.5% by weight. In some embodiments, the caprylyl methicone is provided in a range of about 0.001% to about 4.0%, about 0.01% to about 3.0%, about 0.10% to about 2.5%, or about 0.50% to about 1.5% by weight. In some embodiments, the caprylyl methicone is provided at about 0.25% by weight. In some embodiments, the caprylyl methicone is provided at about 1% by weight.

Bentonite clays can be employed in conjunction with the peptides to provide impart penetration and adsorption properties to the compositions, and can aid in stabilizing emulsions. Other clays, such as hectorite and magnesium aluminum silicate can also be employed. Bentonite or other clays can be modified to yield an organic modified clay compound. Salts (e.g., quaternary ammonium salts) of fatty acids (e.g., hydrogenated fatty acids) can be reacted with hectorite or other clays. As provided herein, fatty acids are referred to and described using conventional nomenclature as is employed by one of skill in the art. A saturated fatty acid includes no carbon-carbon double bonds. An unsaturated fatty acid includes at least one carbon-carbon double bond. A monounsaturated fatty acid includes only one carbon-carbon double bond. A polyunsaturated fatty acid includes two or more carbon-carbon double bonds. Double bonds in fatty acids are generally cis; however, trans double bonds are also possible. The position of double bonds can be indicated by $\Delta n$, where n indicates the lower numbered carbon of each pair of double-bonded carbon atoms. A shorthand notation specifying total #carbons:#double bonds, A double bond positions can be employed. For example, $20:4\Delta_{5,8,11,14}$ refers to a fatty acid having 20 carbon atoms and four double bonds, with the double bonds situated between the 5 and 6 carbon atom, the 8 and 9 carbon atom, the 11 and 12 carbon atom, and the 14 and 15 carbon atom, with carbon atom 1 being the carbon of the carboxylic acid group. Stearate (octadecanoate) is a saturated fatty acid. Oleate (cis-$\Delta$9-octadecenoate) is a monounsaturated fatty acid, linolenate (all-cis-$\Delta$9,12,15-octadecatrienoate) is a polyunsaturated fatty acid. Fatty acids suitable for use can comprise from 5 to 30 carbon atoms, e.g., 5, 6, 7, 8, 9, 10, 11, 12, 13, 14, 15, 16, 17, 18, 19, 20, 21, 22, 23, 24, 25, 26, 27, 28, 29, or 30 carbon atoms. The fatty acid can be fully saturated, or can include as many double bonds as are feasible for the chain length. Fatty acids suitable for functionalizing hectorite or other clays include palmitic acid and stearic acid. Dialkyl quaternary cationic modifiers include dipalmoyldimonium chloride and distearyldimonium chloride. Amidoamine quaternary cationic modifiers include palmitamidopropyltrimonium chloride cetearyl alcohol and palmitamidopropyltrimonium chloride.

In some embodiments, the peptides can be in admixture with a suitable carrier, diluent, or excipient, and can contain auxiliary substances such as wetting or emulsifying agents, pH buffering agents, gelling or viscosity enhancing additives, preservatives, scenting agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for compositions include, without limitation, monoglycerides, diglycerides, sulfatides, lysolecithin, phospholipids, saponin, bile acids, and the like. In some embodiments, compositions described herein comprise, phosphatidylserine, phospholipids, tocopherol, ascorbyl palmitate, or combinations thereof. In some embodiments, phosphatidylserine, phospholipids, tocopherol, ascorbyl palmitate, or combinations thereof is provided at 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the phosphatidylserine, phospholipids, tocopherol, ascorbyl palmitate, or combinations thereof is provided in a range of about 0.25% to about 10%, about 0.5% to about 8%, about 0.75% to about 6%, or about 1% to about 4% by weight. In some embodiments, the phosphatidylserine, phospholipids, tocopherol, ascorbyl palmitate, or combinations thereof is provided in a range of about 0.001% to about 6%, about 0.002% to about 4%, about 0.01% to about 3%, or about 0.02% to about 5% by weight. In some embodiments, the additive is betaine. Betaine, in some embodiments, is provided in a range of about 0.001% to about 6%, about 0.002% to about 4%, about 0.01% to about 3%, or about 0.02% to about 5% by weight. In some embodiments, the compositions as described herein comprise caprylyl glycol. In some embodiments, the caprylyl glycol provided in a range of about 0.001% to about 6%, about 0.002% to about 4%, about 0.01% to about 3%, or about 0.02% to about 5% by weight. In some embodiments, the compositions as described herein comprise caprylhydroxamic acid. In some embodiments, the caprylhydroxamic acid provided in a range of about 0.001% to about 6%, about 0.002% to about 4%, about 0.01% to about 3%, or about 0.02% to about 5% by weight. The presence of such additional components can influence the physical state, solubility, stability, rate of release, rate of clearance, and penetration of active ingredients.

The compositions for topical administration comprise the peptide compositions as described herein and a dermatologically acceptable vehicle. The vehicle may be aqueous or nonaqueous. The dermatologically acceptable vehicle used in the topical composition may be in the form of a lotion, a gel, an ointment, a liquid, a cream, or an emulsion. If the vehicle is an emulsion, the emulsion may have a continuous aqueous phase and a discontinuous nonaqueous or oil phase (oil-in-water emulsion), or a continuous nonaqueous or oil phase and a discontinuous aqueous phase (water-in-oil emulsion). When administered topically in liquid or gel form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or *arachis* oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain coloring and scenting agents.

In certain embodiments, a silicone elastomer (e.g., dimethicone crosspolymer) is employed to increase delivery and penetration of the peptides into the skin. An alternative to increasing molecular weight (as with silicone gums) or adding filler (as with silicone compounds) is to partially crosslink siloxane polymers and disperse this material in an appropriate silicone carrier fluid. The resulting dimethicone crosspolymers (also known as silicone elastomers in the personal care industry) differ from basic polydimethylsiloxane (PDMS) because of the cross-linking between the linear polymers. These materials can be employed in peptide compositions, and also offer benefits in scar treatment, periwound protection and enzyme delivery. In skin care applications, the aesthetics of silicone elastomers (including those with functional groups) and their ability to absorb various oils (e.g., with a dimethicone/vinyl dimethicone crosspolymer such as Dow Corning® 9506 Elastomer Powder) are two of the elastomer's desirable properties. Silicone elastomers have a skin feel different from any of the silicone fluids, described as "smooth," "velvety," and "powdery." It can be modified by controlling the amount of liquid phase in the formula, and therefore the degree of swelling. Due to their film-forming properties, dimethicone crosspolymers can be used as delivery systems for active ingredients such as the peptides described herein, or other composition components such as oil-soluble vitamins and sunscreens. Sunscreens such as octyl methoxycinnamate can be more efficiently delivered from a composition containing a silicone elastomer, producing a higher sun protection factor (SPF). Silicone elastomer blends can be used to enhance SPF in oil-in-water compositions containing organic sunscreens. For example, in testing conducted regarding SPF, the addition of 4% silicone elastomer blend to a sun care composition containing organic sunscreens increased the SPF from 5.7 to 18. This property of the silicone elastomer allows the effectiveness of sunscreen agents in a composition to be maximized while reducing the amount needed to achieve a desired SPF. As a result, composition costs can be reduced along with potential irritation caused by sunscreen actives. Accordingly, a higher SPF can be achieved with the same amount of UV absorber, resulting in enhanced performance with no added composition cost. Silicone elastomers can be produced from linear silicone polymers by a variety of crosslinking reactions, e.g., by a hydrosilylation reaction in which a vinyl group reacts with a silicon hydride. The general process involves linear silicone polymers with reactive sites along the polymer chain reacting with a crosslinker. The dimethicone crosspolymer can be produced either as a gel made of a suspension of elastomer particles swollen in a carrier fluid (e.g., a mixture of high molecular weight silicone elastomer in cyclopentasiloxane such as Dow Corning® 9040 Silicone Elastomer Blend), or as a spray-dried powder (a dimethicone/vinyl dimethicone crosspolymer such as Dow Corning® 9506 Elastomer Powder). The gel form having desirable attributes is cyclomethicone, but low viscosity dimethicones and organic fluids can also be used. Examples of dimethicone crosspolymers in the suspension or gel form are high molecular weight silicone elastomer (12%) in decamethylcyclopentasiloxane (e.g., Dow Corning® ST-Elastomer 10) and a mixture of high molecular weight silicone elastomer in cyclopentasiloxane (e.g., Dow Corning® 9040 Silicone Elastomer Blend), which typically have an elastomer content ranging from 10 to 20% by weight.

The pharmaceutical excipients used in the topical preparations of the peptide compositions may be selected from the group consisting of solvents, emollients and/or emulsifiers, oil bases, preservatives, antioxidants, tonicity adjusters, penetration enhancers and solubilizers, chelating agents, buffering agents, surfactants, one or more polymers, and combinations thereof.

Suitable solvents for an aqueous or hydrophilic liposomal composition include water; ethyl alcohol; isopropyl alcohol; mixtures of water and ethyl and/or isopropyl alcohols; glycerin; ethylene, propylene or butylene glycols; DMSO; pentylene glycol; and mixtures thereof. In some embodiments, glycerin is provided at least or about 1%, 2%, 3%, 4%, 5%, 6%, 7%, 8%, 9%, 10%, 11%, 12%, or more than 12% by weight (wt. %). In some embodiments, glycerin is provided at least or about 7%. In some embodiments, glycerin is provided in a range of about 1% to about 12%, about 2% to about 11%, or about 3% to about 10% by weight. In some embodiments, butylene glycol is provided at least or about 0.0025%, 0.005%, 0.075%, 0.01%, 0.025%, 0.05%, 0.75%, 1%, 2%, 3%, 4%, 5%, 6%, 7% 8%, 9%, 10%, 11%, 12%, or more than 12% by weight. In some embodiments, butylene glycol is provided in a range of about 0.01% to about 10%, about 0.025% to about 5%, or about 0.05% to about 1.25% by weight. In some embodiments, pentylene glycol is provided at least or about 0.0025%, 0.005%, 0.075%, 0.01%, 0.025%, 0.05%, 0.75%, 1%, 2%, 3%, 4%, 5%, 6%, 7% 8%, 9%, 10%, 11%, 12%, or more than 12% by weight. In some embodiments, pentylene glycol is provided in a range of about 0.01% to about 10%, about 0.025% to about 5%, or about 0.05% to about 1.25% by weight. Suitable solvents for hydrophobic compositions include mineral oils, vegetable oils, and silicone oils. If desired, the peptide compositions as described herein may be dissolved or dispersed in a hydrophobic oil phase, and the oil phase may then be emulsified in an aqueous phase comprising water, alone or in combination with lower alcohols, glycerin, and/or glycols. In some embodiments, an anhydrous composition is applied as the presence of water can result in stinging upon administration to skin tissues subject to laser treatment, chemical peel, dermabrasion, or the like. Anhydrous compositions may also act to prevent the development of water-based irritant contact dermatitis in damaged or sensitive skin, which may produce rashes and skin irritation that may retard wound healing and improvement in skin quality. Tsai, T. F., Maibach, H. I. How irritant is water? An overview. Contact Dermatitis 41(6) (1999): 311-314 (describing contact dermatitis caused by water as an irritant). However, in certain embodiments it may be acceptable to provide water based compositions, or to permit a limited amount of water to be present. For example, water may be present, but at amounts below the threshold at which a stinging sensation when applied to damaged skin may result. Osmotic shock or osmotic stress is a sudden change in the solute concentration around a cell, causing a rapid change in the movement of water across its cell membrane. Under conditions of high concentrations of either salts, substrates or any solute in the supernatant, water is drawn out of the cells through osmosis. This also inhibits the transport of substrates and cofactors into the cell thus "shocking" the cell. Alternatively, at low concentrations of solutes, water enters the cell in large amounts, causing it to swell and either burst or undergo apoptosis. Certain of the compositions as described herein can be advantageously employed where it is desirable to minimize osmotic shock.

Compositions as described herein may comprise varying amounts of solvent. In some embodiments, the solvent is water. In some embodiments, the solvent is at least or about 10%, 15%, 20%, 25%, 30%, 35%, 40%, 45%, 50%, 55%, 60%, 65%, 70%, 75%, 80%, 85%, 90%, 95%, or more than 95% by weight (wt. %). In some embodiments, the solvent is in a range of about 10% to about 95%, about 20% to about 90%, about 30% to about 85%, about 40% to about 80%, or about 50% to about 75% by weight.

Viscosity of the compositions can be maintained at the selected level using a pharmaceutically acceptable thickening agent. Suitable viscosity enhancers or thickeners which may be used to prepare a viscous gel or cream with an aqueous base include sodium polyacrylate, xanthan gum, polyvinyl pyrrolidone, acrylic acid polymer, carrageenans, hydroxyethyl cellulose, hydroxypropyl cellulose, methyl cellulose, ethyl cellulose, propyl cellulose, hydroxypropyl methyl cellulose, polyethoxylated polyacrylamides, polyethoxylated acrylates, and polyethoxylated alkane thiols. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the thickening agent selected. An amount is preferably used that will achieve the selected viscosity. Viscous compositions are normally prepared from solutions by the addition of such thickening agents, or by employing a base that has an acceptable level of viscosity.

The viscosity of the compositions as described herein, in some embodiments, are in a range of about 8,000 centipoise (cps) to about 30,000 cps. In some embodiments, the viscosity is at least or about 4,000; 5,000; 6,000; 7,000; 8,000; 9,000; 10,000; 11,000; 12,000; 13,000; 14,000; 15,000; 16,000; 17,000; 18,000; 19,000; 20,000; 21,000; 22,000; 23,000; 24,000; 25,000; 26,000; 27,000; 28,000; 29,000; 30,000; 31,000; 32,000; 33,000; 34,000, 35,000; 36,000; 37,000; 38,000; 39,000; 40,000; or more than 40,000 cps. In some embodiments, the composition comprises a viscosity in a range of about 4,000 to about 40,000, about 6,000 to about 38,000, about 8,000 to about 36,000, about 10,000 to about 34,000 cps, about 12,000 to about 32,000 cps, or about 14,000 to about 30,000 cps.

Suitable emollients include hydrocarbon oils and waxes such as mineral oil, petrolatum, paraffin, ceresin, ozokerite, microcrystalline wax, polyethylene, squalene, perhydrosqualene, silicone oils, triglyceride esters, acetoglyceride esters, such as acetylated monoglycerides; ethoxylated glycerides, such as ethoxylated glyceryl monostearate; alkyl esters of fatty acids or dicarboxylic acids. In some embodiments, the emollient is caprylic/capric triglyceride.

In some embodiments, the emollient is provided at least or about 0.0025%, 0.005%, 0.075%, 0.01%, 0.025%, 0.05%, 0.75%, 1%, 2%, 3%, 4%, 5%, 6%, 7%, 8%, 9%, 10%, 11%, 12%, or more than 12% by weight. In some embodiments, the emollient is provided in a range of about 0.01% to about 10%, about 0.01% to about 2.5%, about 0.025% to about 5%, or about 0.05% to about 1.25% by weight. In some embodiments, the caprylic/capric triglyceride is provided at least or about 0.0025%, 0.005%, 0.075%, 0.01%, 0.025%, 0.05%, 0.75%, 1%, 2%, 3%, 4%, 5%, 6%, 7%, 8%, 9%, 10%, 11%, 12%, or more than 12% by weight. In some embodiments, the caprylic/capric triglyceride is provided in a range of about 0.01% to about 10%, about 0.01% to about 2.5%, about 0.025% to about 5%, or about 0.05% to about 1.25% by weight.

Suitable silicone oils for use as emollients include dimethyl polysiloxanes, methyl(phenyl) polysiloxanes, and water-soluble and alcohol-soluble silicone glycol copolymers. Suitable triglyceride esters for use as emollients include vegetable and animal fats and oils including castor oil, safflower oil, cotton seed oil, corn oil, olive oil, cod liver oil, almond oil, avocado oil, palm oil, sesame oil, and soybean oil.

Suitable esters of carboxylic acids or diacids for use as emollients include methyl, isopropyl, and butyl esters of fatty acids. Specific examples of alkyl esters including hexyl laurate, isohexyl laurate, iso-hexyl palmitate, isopropyl palmitate, decyl oleate, isodecyl oleate, hexadecyl stearate, decyl stearate, isopropyl isostearate, dilauryl lactate, myristyl lactate, and cetyl lactate; and alkenyl esters of fatty acids such as oleyl myristate, oleyl stearate, and oleyl oleate. Specific examples of alkyl esters of diacids include diisopropyl adipate, diisohexyl adipate, bis(hexyldecyl) adipate, and diisopropyl sebacate.

Other suitable classes of emollients or emulsifiers which may be used in the compositions include fatty acids, fatty alcohols, fatty alcohol ethers, ethoxylated fatty alcohols, fatty acid esters of ethoxylated fatty alcohols, and waxes.

Specific examples of fatty acids for use as emollients include pelargonic, lauric, myristic, palmitic, stearic, isostearic, hydroxystearic, oleic, linoleic, ricinoleic, arachidic, behenic, and erucic acids. Specific examples of fatty alcohols for use as emollients include lauryl, myristyl, cetyl, hexadecyl, stearyl, isostearyl, hydroxystearyl, oleyl, ricinoleyl, behenyl, and erucyl alcohols, as well as 2-octyl dodecanol.

Specific examples of waxes suitable for use as emollients include lanolin and derivatives thereof including lanolin oil, lanolin wax, lanolin alcohols, lanolin fatty acids, isopropyl lanolate, ethoxylated lanolin, ethoxylated lanolin alcohols, ethoxolated cholesterol, propoxylated lanolin alcohols, acetylated lanolin, acetylated lanolin alcohols, lanolin alcohols linoleate, lanolin alcohols recinoleate, acetate of lanolin alcohols recinoleate, acetate of lanolin alcohols recinoleate, acetate of ethoxylated alcohols esters, hydrogenolysates of lanolin, hydrogenated lanolin, ethoxylated hydrogenated lanolin, ethoxylated sorbitol lanolin, and liquid and semi-solid lanolin. Also usable as waxes include hydrocarbon waxes, ester waxes, and amide waxes. Useful waxes include wax esters such as beeswax, spermaceti, myristyl myristate and stearyl stearate; beeswax derivatives, e.g., polyoxyethylene sorbitol beeswax; and vegetable waxes including carnauba and candelilla waxes.

Polyhydric alcohols and polyether derivatives may be used as solvents and/or surfactants in the compositions. Suitable polyhydric alcohols and polyethers include propylene glycol, dipropylene glycol, polypropylene glycols 2000 and 4000, poly(oxyethylene-co-oxypropylene) glycols, glycerol, sorbitol, ethoxylated sorbitol, hydroxypropylsorbitol, polyethylene glycols 200-6000, methoxy polyethylene glycols 350, 550, 750, 2000 and 5000, poly[ethylene oxide] homopolymers (100,000-5,000,000), polyalkylene glycols and derivatives, hexylene glycol, 2-methyl-2,4-pentanediol, 1,3-butylene glycol, 1,2,6-hexanetriol, 2-ethyl-1,3-hexanediol, vicinal glycols having 15 to 18 carbon atoms, and polyoxypropylene derivatives of trimethylolpropane.

Polyhydric alcohol esters may be used as emulsifiers or emollients. Suitable polyhydric alcohol esters include ethylene glycol mono- and di-fatty acid esters, diethylene glycol mono- and di-fatty acid esters, polyethylene glycol (200-6000) mono- and di-fatty acid esters, propylene glycol mono- and di-fatty esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

Suitable emulsifiers for use in compositions include anionic, cationic, nonionic, and zwitterionic surfactants. Preferred ionic emulsifiers include phospholipids, such as lecithin and derivatives.

Sterols including, for example, cholesterol and cholesterol fatty acid esters; amides such as fatty acid amides, ethoxylated fatty acid amides, and fatty acid alkanolamides may also be used as emollients and/or penetration enhancers.

A pharmaceutically acceptable preservative can be employed to increase the shelf life of the composition. Other suitable preservatives and/or antioxidants for use in compositions include benzalkonium chloride, benzyl alcohol, phenol, urea, parabens, butylated hydroxytoluene (BHT), butylated hydroxyanisole (BHA), tocopherol, thimerosal, chlorobutanol, or the like, and mixtures thereof, can be employed. If a preservative, such as an antioxidant, is employed, the concentration is typically from about 0.02% to about 2% based on the total weight of the composition, although larger or smaller amounts can be desirable depending upon the agent selected. Reducing agents, as described herein, can be advantageously used to maintain good shelf life of the composition. It is generally observed that the anhydrous compositions of the embodiments exhibit satisfactory stability, such that a preservative can be omitted from the composition.

Suitable chelating agents for use in compositions include ethylene diamine tetraacetic acid, alkali metal salts thereof alkaline earth metal salts thereof, ammonium salts thereof, and tetraalkyl ammonium salts thereof. In some embodiments, the chelating agent is disodium ethylenediaminetetraacetic acid (EDTA). In some embodiments, the disodium EDTA is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, or more than 4% by weight (wt. %). In some embodiments, the disodium EDTA is provided in a range of about 0.25% to about 10%, about 0.1% to about 2.5%, about 0.5% to about 8%, about 0.75% to about 6%, or about 1% to about 4% by weight. In some embodiments, the disodium EDTA is provided in a range of about 0.001% to about 6%, about 0.002% to about 4%, about 0.01% to about 3%, or about 0.02% to about 2% by weight.

The carrier preferably has a pH of between about 4.0 and 10.0, more preferably between about 4.8 and about 7.8, more preferably between about 5.0 to about 6.5. The pH may be controlled using buffer solutions or other pH modifying agents. Suitable pH modifying agents include phosphoric acid and/or phosphate salts, citric acid and/or citrate salts, hydroxide salts (i.e., calcium hydroxide, sodium hydroxide, potassium hydroxide) and amines, such as triethanolamine. Suitable buffer solutions include a buffer comprising a solution of monopotassium phosphate and dipotassium phosphate, maintaining a pH of between 5.8 and 8; and a buffer comprising a solution of monosodium phosphate and disodium phosphate, maintaining a pH of between 6 and 7.5. Other buffers include citric acid/sodium citrate, and dibasic sodium phosphate/citric acid. The peptide compositions of the embodiments are preferably isotonic with the blood or other body fluid of the recipient. The isotonicity of the compositions can be attained using sodium tartrate, propylene glycol or other inorganic or organic solutes. Sodium chloride is particularly preferred. Buffering agents can be employed, such as acetic acid and salts, citric acid and salts, boric acid and salts, and phosphoric acid and salts. It can be desirable to include a reducing agent in the composition, such as vitamin C, vitamin E, or other reducing agents as are known in the pharmaceutical arts.

Surfactants can also be employed as excipients, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

In certain embodiments, it can be advantageous to include additional agents having pharmacological activity. Anti-infective agents include, but are not limited to, anthelmintic (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin, clindamycin, colistimethate sodium, polymyxin b sulfate, vancomycin, antivirals including acyclovir, amantadine, didanosine, efavirenz, foscarnet, ganciclovir, indinavir, lamivudine, nelfinavir, ritonavir, saquinavir, stavudine, valacyclovir, valganciclovir, zidovudine, quinolones (ciprofloxacin, levofloxacin), sulfonamides (sulfadiazine, sulfisoxazole), sulfones (dapsone), furazolidone, metronidazole, pentamidine, sulfanilamidum crystallinum, gatifloxacin, and sulfamethoxazole/trimethoprim. Anesthetics can include, but are not limited to, ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine. Anti-inflammatory agents include but are not limited to, nonsteroidal anti-inflammatory drugs (NSAIDs) such as aspirin, celecoxib, choline magnesium trisalicylate, diclofenac potassium, diclofenac sodium, diflunisal, etodolac, fenoprofen, flurbiprofen, ibuprofen, indomethacin, ketoprofen, ketorolac, melenamic acid, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, triamcinolone acetonide, betamethasone, fluocinonide, betamethasone dipropionate, betamethasone valerate, desonide, desoximetasone, fluocinolone, triamcinolone, clobetasol propionate, and dexamethasone.

In certain embodiments, the addition of emollients, emulsion stabilizers, moisturizers, excipients, and other compounds may be modified to enhance the sensory properties of the topical compositions, including but not limited to: skin feel (silkiness, lightness, creaminess, etc.), absorbency (required time at which product loses wet feel and is no longer perceived on skin), consistency, firmness, spreadability (e.g. viscosity, flow onset, shear rates), stickiness, integrity of shape, glossiness, hydrophilicity or hydrophobicity, and others. Preferably, compositions will have high spreadability and low viscosity properties. Compositions with such properties have been demonstrated to have an enhanced "silky" or "light" skin feel rating (see e.g. Bekker, M. Webber, G., Louw, N. Relating rheological measurements to primary and secondary skin feeling when mineral-based and Fischer-Tropsch wax-based cosmetic emulsions and jellies are applied to the skin, International Journal of Cosmetic Science 2013, 35(4), pp. 354-61).

In some embodiments, compositions comprise phenoxyethanol, ethylhexylglycerin, or combinations thereof. In some embodiments, phenoxyethanol is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, phenoxyethanol is provided in a range of about 0.25% to about 10%, about 0.5% to about 8%, about 0.75% to about 6%, or about 1% to about 4% by weight. In some embodiments, ethylhexylglycerin is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, ethylhexylglycerin is provided in a range of about 0.25% to about 10%, about 0.5% to about 8%, about 0.75% to about 6%, or about 1% to about 4% by weight. In some embodiments, phenoxyethanol and ethylhexylglycerin are provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, phenoxyethanol and ethylhexylglycerin are provided in a range of about 0.25% to about 10%, about 0.1% to about 4%, about 0.5% to about 8%, about 0.75% to about 6%, or about 1% to about 4% by weight.

In some embodiments, compositions comprise polyacrylate-13, polyisobutene, polysorbate 20, or combinations thereof. In some embodiments, polyacrylate-13 is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, polyacrylate-13 is provided in a range of about 0.25% to about 10%, about 0.5% to about 8%, about 0.75% to about 6%, or about 1% to about 4% by weight. In some embodiments, polyisobutene is provided at least or about 0.05%, 0.10%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, polyisobutene is provided in a range of about 0.25% to about 10%, about 0.5% to about 8%, about 0.75% to about 6%, or about 1% to about 4% by weight. In some embodiments, polyacrylate-13 is provided in a range of about 0.25% to about 10%, about 0.5% to about 8%, about 0.75% to about 6%, or about 1% to about 4% by weight. In some embodiments, polysorbate 20 is provided at least or about 0.05%, 0.10%, 0.25%, 0.50%, 0.75%, 1.0%, 1.5%, 2.0%, 2.5%, 3.0%, 3.5%4, 4.0%, 4.5%, 5.0%, 5.5%, 6.0%, 6.5%, 7.0%, 8%, 9%, 10%, or more than 10% by weight (wt. %). In some embodiments, polysorbate 20 is provided in a range of about 0.25% to about 10%, about 0.5% to about 8%, about 0.75% to about 6%, or about 1% to about 4% by weight. In some embodiments, polyacrylate-13, polyisobutene, and polysorbate 20 are provided at least or about 0.05%, 0.10%, 0.25%, 0.50%, 0.75%, 1.0%, 1.5%, 2.0%, 2.5%, 3.0%, 3.5%4, 4.0%, 4.5%, 5.0%, 5.5%, 6.0%, 6.5%, 7.0%, 8%, 9%, 10%, or more than 10% by weight (wt. %). In some embodiments, polyacrylate-13, polyisobutene, and polysorbate 20 are provided in a range of about 0.25% to about 10%, about 0.1% to about 4%, about 0.5% to about 8%, about 0.75% to about 6%, or about 1% to about 4% by weight (wt. %).

In some embodiments, compositions as described herein comprise potassium sorbate. In some embodiments, the potassium sorbate is provided at least or about 0.001%, 0.00175%, 0.0025%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the potassium sorbate is provided in a range of about 0.001% to about 6%, about 0.002% to about 4%, about 0.01% to about 3%, or about 0.02% to about 2% by weight.

In some embodiments, the liposomes comprise propanediol, lecithin, or a combination thereof. In some embodiments, the propanediol is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the propanediol is provided in a range of about 0.001% to about 6%, about 0.002% to about 4%, about 0.01% to about 3%, or about 0.02% to about 2% by weight. In some embodiments, the lecithin is provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the lecithin is provided in a range of about 0.001% to about 6%, about 0.002% to about 4%, about 0.01% to about 3%, or about 0.02% to about 2% by weight. In some embodiments, the liposomes comprise propanediol and lecithin. In some embodiments, the propanediol and lecithin are provided at least or about 0.001%, 0.005%, 0.01%, 0.02%, 0.05%, 0.10%, 0.20%, 0.25%, 0.50%, 0.75%, 1.0%, 1.5%, 2.0%, 2.5%, 3.0%, 3.5%, 4.0%, 4.5%, 5.0%, 5.5%, 6.0%, 6.5%, 7.0%, 8%, 9%, 10%, or more than 10% by weight (wt. %). In some embodiments, the propanediol and lecithin are provided in a range of about 0.001% to about 6%, about 0.002% to about 4%, about 0.01% to about 3%, or about 0.02% to about 2% by weight. In some embodiments, the propanediol and lecithin are provided at about 0.90% by weight.

The topical composition may contain micelles, or an aggregate of surfactant molecules dispersed in an aqueous solution. Micelles may be prepared by dispersing an oil solvent in an aqueous solution comprising a surfactant, where the surfactant concentration exceeds the critical micelle concentration. The resulting composition contains micelles, i.e., spherical oil droplets Penetration Enhancers Fatty acids and alcohols can be employed to enhance penetration of the peptides, and to provide a silky feel to compositions, e.g., methanoic acid, ethanoic acid, propanoic acid, butanoic acid, isobutyric acid, pentanoic acid, hexanoic acid, heptanoic acid, octanoic acid, nonanoic acid, decanoic acid, myristoleic acid, isovaleric acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, palmitic acid, stearic acid, arachidic acid, behenic acid, lignoceric acid, cerotic acid, medium chain fatty acids, e.g., $C_{6-12}$ fatty acids, or the like. Typical amounts when employed in compositions are from 1% by weight to 4% by weight.

Antimicrobial Efficacy

Described herein, in some embodiments, are chemically and physically stable compositions at physiological pH. In some embodiments, the compositions are sterile and safe for human administration. In some embodiments, the compositions comply with or pass the required antimicrobial efficacy tests such as the Antimicrobial Effectiveness Test. In some embodiments, the compositions result in complete or substantially complete eradication of bacteria, yeast, mold, or combinations thereof.

Therapeutic Uses

Described herein are compositions and methods for improving bruising. Bruising can be caused by a variety of sources. In some embodiments, bruising is a result of surgery, laser treatment, or trauma. In some embodiments, bruising is a result of a cosmetic procedure. In some embodiments, bruising is a result of a medical procedure. In some embodiments, the compositions and methods described herein improve bruising prior to or after a cosmetic procedure, a medical procedure, or a trauma.

Also described herein are compositions and methods for stimulation of increased collagen, elastin, fat, or hyaluronic acid. In some embodiments, the stimulation is adjunct to an injection of a soft tissue filler.

In some embodiments, the cosmetic procedure comprises a cosmetic surgery. Exemplary cosmetic surgeries include, but are not limited to, forehead lift, cheek enhancement, otoplasty, rhytidectomy, lower rhytidectomy, cheek reduction, mentoplasty, blepharoplasty, facial implant, nose surgery, skin excision, skin biopsy, invasive cellulite treatment, injection of a filler, and injection of an injectable such as Botox®, Dysport®, or Xeomin®.

In some embodiments, the cosmetic procedure comprises injection of a filler. In some embodiments, the filler is a soft tissue filler product. For example, the soft tissue filler is an injectable dermal or subdermal filler. In some embodiments, the filler is a breast augmentation or reconstruction filler, a lip filler, or filler suitable for other soft tissue restoration or augmentation. In some embodiments, the filler is dermal filler. In some instances, the dermal filler is administered through injection into or beneath the skin of a subject.

In some embodiments, the cosmetic procedure comprises injection of an injectable such as Botox®, Dysport®, or Xeomin®.

In some embodiments, the cosmetic procedure is microneedling. In some instances, the cosmetic procedure is radiofrequency microneedling. In some instances, the cosmetic procedure is a chemical peel. In some instances, the cosmetic procedure is microdermabrasion.

In some embodiments, the cosmetic procedure comprises cellulite reduction or enzymatic (collagenase) or mechanical disruption of fascial bands.

Bruising, in some instances, is caused by an invasive procedure. In some instances, the invasive procedure comprises use of an invasive laser or surgery. In some instances, bruising is caused by a non-invasive procedure. In some instances, the non-invasive procedure comprises non-surgical skin tightening, non-surgical fat reduction, or use of a non-invasive laser. In some instances, the procedure is a body-shaping or body-contouring procedure. Exemplary body-shaping or body-contouring procedures include, but are not limited to, high frequency focused ultrasound, pulsed focus ultrasound, cryolipolysis, radiofrequency induced electroporation, injectable lipolytic agents, and liposuction. In some embodiments, the procedure is a fat reduction procedure. The fat reduction procedure may be low level laser therapy, infrared light, ultrasound, radiofrequency, or cryolipolysis. In some instances, the procedure comprises an energy source. In some instances, the energy source is electromagnetic energy. In some instances, the procedure is high intensity focused electro-magnetic technology (HIFEM).

In some embodiments, the medical procedure comprises therapeutic injections, placement of intravenous (IV) lines, or invasive surgery.

In some embodiments, the medical procedure comprises procedures to reduce visibility of veins. In some embodiments, the visible vein is a varicose vein. Exemplary procedures to reduce visibility of veins include, but are not limited to, post vein sclerotherapy, laser treatment, endovenous laser therapy (EVLT), radiofrequency ablation (RFA), catheter-assisted procedures using radiofrequency or laser energy, high ligation and vein stripping, ambulatory phlebectomy, and endoscopic vein surgery.

Bruising may be caused by various factors. In some embodiments, bruising is caused by trauma. In some instances, bruising is caused by an injury, contusion, strain, sprain, dislocation, broken bone, torn tendon, or muscle swelling resulting in bruising. In some instances, bruising is caused by a medication, herb, or supplement. In some instances, bruising is caused by a vitamin deficiency. In some cases, bruising is caused by malnutrition. In some embodiments, bruising is a result of an underlying disease or disorder. Exemplary diseases or disorders that can result in bruising include, but are not limited to, Cushing's syndrome, thrombocytopenia, leukemia, Von Willebrand disease, hemophilia A, hemophilia B, Factor VII deficiency, Factor X deficiency, Factor V deficiency, Factor II deficiency, varicose veins, and deep vein thrombosis.

In some embodiments, bruising resulting from a trauma occurs in a subject more prone to bruising. In some embodiments, the subject more prone to bruising is an elderly individual having capillary fragility. In some embodiments, the subject more prone to bruising is taking a medication having a side effect of increasing the propensity to bruise.

Described herein are methods and compositions for improving various types of bruises. In some embodiments, the bruise is a nonpalpable (macular) purpura. In some embodiments, the bruise is a palpable (papular) purpura. In some embodiments, the bruise is a nonthrombocytopenic purpura. In some embodiments, the bruise is a thrombocytopenic purpura. In some embodiments, the bruise is senile purpura.

Described herein are methods and compositions for improving various types of bruises in an elderly individual. In some embodiments, the elderly individual has chronic skin fragility. In some embodiments, the elderly individual has dermatoporosis. In some embodiments, the elderly individual has a nonpalpable (macular) purpura, a palpable (papular) purpura, a nonthrombocytopenic purpura, a thrombocytopenic purpura, or a senile purpura. In some embodiments, the elderly individual has a senile purpura.

Methods and compositions as described herein may improve bruising following a cosmetic procedure. In some embodiments, methods and compositions improve bruising prior to a cosmetic procedure. In some instances, bruising is caused by red blood cells. Generally, red blood cells efficiently bind oxygen from the atmosphere, deliver it to the tissues, and help remove carbon dioxide. In some instances, red blood cells are involved in pathophysiologic problems with hemorrhage and extravasation of these cells into the tissue. Once outside the vascular system, red blood cells can quickly burst releasing free hemoglobin (Hb). That Hb may be prone to spontaneous oxidation and may be converted to higher oxidation states such as ferrylHb which have potent pro-inflammatory and pro-oxidant effects. See Jeney V, Eaton J W, Balla G, Balla J. Natural history of the bruise: formation, elimination, and biological effects of oxidized hemoglobin. *Oxidative medicine and cellular longevity.* 2013; 2013:703571. The heme that is released may be phagocytosed by macrophages. Following internalization by the macrophage, heme is cleaved into biliverdin, carbon monoxide, and iron. This mechanism can provide effective elimination of Hb, but it also assures iron recycling for new erythropoiesis (new red blood cell formation) under normal circumstances. See Jeney V, Eaton J W, Balla G, Balla J. Natural history of the bruise: formation, elimination, and biological effects of oxidized hemoglobin. *Oxidative medicine and cellular longevity.* 2013; 2013:703571. In some instances, leaving the byproducts of bleeding around for too long runs the risk of the pro-inflammatory effects. In some instances, these effects interfere with wound healing, promote pigmentation, or are unsightly. In some instances, delayed bruising results. See Sadeghpour M, Dover J S. Understanding Delayed Bruising After Hyaluronic Acid Injections: Why the Molecule and Not Just the Injection Matters—letters and communications. *Dermatol Surg.* 2019; 45(3):471-473. Compositions and methods as described herein, in some embodiments, improve bruising by removing by-products of red blood cell extravasation more efficiently. In some embodiments, compositions described herein result in improving function of macrophages.

Compositions as described herein comprising lactoferrin, phosphatidylserine, tripeptide-1, hexapeptide-12, hexapeptide-11, *Arnica montana* extract, *Ledum palustre*, or combinations thereof, in some embodiments, improve bruising. Lactoferrin is a plasmin inhibitor with high iron binding capacity and can aid in clearing lysed red blood cells and their constituents. Lactoferrin can block plasminogen activation on the cell surface by direct binding to human plasminogen, decreasing conversion to plasmin. Lactoferrin also has anti-microbial activity. See Zwirzitz A, Reiter M, Skrabana R, et al. Lactoferrin is a natural inhibitor of plasminogen activation. *Journal of Biological Chemistry.* 2018; 293(22):8600-8613.

Compositions as described herein, in some embodiments, improve bruising by improving healing or appearance of the bruise. In some embodiments, the compositions improve bruising by accelerating resolution of the bruise. For example, the compositions accelerate the transition of blue coloration to red coloration of the bruise. In some embodiments, improved appearance of the bruise comprises reduced size of the bruise. In some embodiments, improved appearance of the bruise comprises reduced discoloration of the skin. In some embodiments, improved appearance of the bruise comprises reduced swelling. In some embodiments, the compositions as described herein improve bruising by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein improve bruising by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Compositions described herein may improve bruising by improving macrophage function. In some embodiments, macrophage function comprises phagocytosis. In some embodiments, compositions as described herein improve macrophage phagocytosis by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, compositions as described herein improve macrophage phagocytosis by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Compositions and methods as described herein may result in elastin and/or collagen stimulation. Elastin is an assembly of microfibrils and tropoelastin (or soluble elastin). Elastin fibers are formed first by the synthesis of fibrillin microfibers which intertwine and then associate with tropoelastin (TE) protein molecules. TE molecules are bound together and cross linked together with fibrillin fibers by lysyl oxidase like enzyme 1 (LOXL1). The generated complex is then presented to the fibroblast by Fibulin 5 (FBLN5) which connects the complex to integrins that connect to the fibroblast. See Ashcroft, G. et al. Age-related Changes in the Temporal and Spatial Distributions of Fibrillin and Elastin mRNAs and Protein in Acute Cutaneous Wounds of Healthy Humans, Journal of Pathology. 1997; 183:80-89; Cenizo V, Andre' V, Reymermier C, Sommer P, Damour O, E. P. LOXL as a target to increase the elastin content in adult skin: a dill extract induces the LOXL gene expression. *Experimental dermatology.* 2006; 15:574-581; Noblesse E, Cenizo V, Bouez C, et al. Lysyl oxidase-like and lysyl oxidase are present in the dermis and epidermis of a skin equivalent and in human skin and are associated to elastic fibers. *The Journal of investigative dermatology.* 2004; 122(3):621-630.

In some embodiments, elastin and/or collagen stimulation is a result of the compositions as described herein. In some embodiments, palmitoyl tripeptide-1 and palmitoyl hexapeptide-12 clear the extracellular matrix of aggregated fragmented collagen and elastin and then stimulate increased new collagen and elastin production. See Widgerow A D, Fabi S G, Palestine R F, et al. Extracellular Matrix Modulation: Optimizing Skin Care and Rejuvenation Procedures. *journal of drugs in dermatology.* 2016; 15(4s):S63-S71; Widgerow A. TOPICAL SKIN RESTORATION TECHNOLOGY—ADVANCES IN AGE MANAGEMENT STRATEGIES. *MODERN AESTHETICS.* 2016(May/June): 1-8. In some embodiments, acetyl tetrapeptide-2 increases FBLN5 and LOXL1 protein levels, resulting in an increase in elastin synthesis. In some instances, acetyl tetrapeptide-2 upregulates genes related to Collagen 1 synthesis. Acetyl tetrapetide-2 can reduce parameters linked to skin flaccidity and dermal disorganization in vivo. See Product monograph: Uplevity™. Lipotec. June 2013.

In some embodiments, *Anethum graveolens* (dill extract) improves elastin and/or collagen stimulation by producing a reinduction of LOXL synthesis. See Cenizo V, Andre' V, Reymermier C, Sommer P, Damour O, E. P. LOXL as a target to increase the elastin content in adult skin: a dill extract induces the LOXL gene expression. *Experimental dermatology.* 2006; 15:574-581. While microfibrils and soluble elastin continue to be synthesized throughout life, LOXL dramatically decreases from the age of 18. Increased levels of LOXL in the skin cause the assembly of microfibrils and tropoelastin, leading to improved mechanical properties of the skin. Id. Elastogenesis mainly occurs until the end of the second decade of the life, although the global content of skin elastin can increase after that, the nature of this elastin protein is often suboptimal and dysfunctional. See Ashcroft, G. et al. Age-related Changes in the Temporal and Spatial Distributions of Fibrillin and Elastin mRNAs and Protein in Acute Cutaneous Wounds of Healthy Humans, Journal of Pathology. 1997; 183:80-89. After this period, the elastin gene and fibrillin-1 gene are still active throughout the life although elastogenesis becomes low or inefficient. See Cenizo V, Andre' V, Reymermier C, Sommer P, Damour O, E. P. LOXL as a target to increase the elastin content in adult skin: a dill extract induces the LOXL gene expression. *Experimental dermatology.* 2006; 15:574-581. LOXL, which declines after the first decades of life, has been shown to stimulate elastogenesis and maintain elastic fibers homeostasis. Id.; Noblesse E, Cenizo V, Bouez C, et al. Lysyl oxidase-like and lysyl oxidase are present in the dermis and epidermis of a skin equivalent and in human skin and are associated to elastic fibers. *The Journal of investigative dermatology.* 2004; 122(3):621-630; Liu X, Zhao Y, Gao J, et al. Elastic fiber homeostasis requires lysyl oxidase-like 1 protein. Nat Genet. 2004; 36(2):178-182. In some instances, dill extract increases the expression of LOXL in fibroblasts and in the skin engineering models and to de novo elastogenesis in vivo. See Cenizo V, Andre' V, Reymermier C, Sommer P, Damour O, E. P. LOXL as a target to increase the elastin content in adult skin: a dill extract induces the LOXL gene expression. *Experimental dermatology.* 2006; 15:574-581.

In some embodiments, the compositions as described herein stimulate elastin production by at least or about 10%, 15%, 20%, 25%, 30%, 35%, 40%, 45% 50%, 55%, 60%, 65%, 70%, 75%, 80%, 85%, 90%, 95%, or more than 95%. In some embodiments, the compositions as described herein stimulate elastin production by at least or about 0.5×, 1. OX, 1.5×, 2.0×, 2.5×, 3.0×, 3.5×, 4.0×, 5.0×, 6.0×, 7.0×, 8.0×, 9.0×, 10×, or more than 10×. In some embodiments, the compositions as described herein stimulate collagen production by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein stimulate collagen production by at least or about 0.5×, LOX, 1.5×, 2.0×, 2.5×, 3.0×, 3.5×, 4.0×, 5.0×, 6.0×, 7.0×, 8.0×, 9.0×, 10×, or more than 10×.

Compositions and methods as described herein, in some embodiments, simulate intrinsic hyaluronic acid (HA) production. Compositions and methods as described herein can improve high molecular weight HA penetration of the skin to the dermis. In some embodiments, compositions comprising hydroxymethoxyphenyl decanone, *Tremella fuciformis* extract, lactoferrin, sodium hyaluronate crosspolymer, phosphatidylserine, or combinations thereof stimulate intrinsic hyaluronic acid production.

In some embodiments, hydroxymethoxyphenyl decanone stimulates intrinsic hyaluronic acid production. Hydroxymethoxyphenyl decanone is a potent hyaluronic acid booster, antioxidant and anti-irritant and has been demonstrated to stimulate the dermal and epidermal hyaluronic acid level by 259% and 198% versus placebo, respectively in ex vivo human skin model. See Product monograph: Symdecanox, Symrise June 2015.

In some embodiments, *Tremella fuciformis* extract stimulates intrinsic hyaluronic acid production. In some embodiments, *Tremella fuciformis* provides high levels of moisture and anti-oxidant properties. See Li H, Lee H S, Kim S H, Moon B, Lee C. Antioxidant and anti-inflammatory activities of methanol extracts of *Tremella fuciformis* and its major phenolic acids. *J Food Sci.* 2014; 79(4):C460-468; Liao W C, Hsueh C Y, Chan C F. Antioxidative activity, moisture retention, film formation, and viscosity stability of *Auricularia fuscosuccinea*, white strain water extract. *Biosci Biotechnol Biochem.* 2014; 78(6):1029-1036.

In some embodiments, sodium hyaluronate crosspolymer stimulates intrinsic hyaluronic acid production. Sodium hyaluronate crosspolymer is a chemically crosslinked hyaluronic acid derived from a non-animal source with high water-binding capacity. Sodium hyaluronate crosspolymer can function as a scavenger of damaging free radicals. Sodium hyaluronate crosspolymer comprises a gel structure with gel domains that hold tightly bound water, which can form a film on the skin and delivers water over time. In some embodiments, sodium hyaluronate crosspolymer comprises fifty (50) times the water binding capacity of hyaluronic acid.

In some embodiments, the compositions as described herein stimulate intrinsic hyaluronic acid production by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein stimulate intrinsic hyaluronic acid production by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Described herein are compositions and methods for stimulating adipogenesis. In some embodiments, fillers stimulate new adipose formation by mechanical stimulation of adipose stem cells in the dermal white adipose tissue layer. See Kruglikov I L, Wollina U. Soft tissue fillers as non-specific modulators of adipogenesis: change of the paradigm?*Experimental dermatology.* 2015; 24(12):912-915. In some embodiments, compositions comprising acetyl hexapeptide-38 stimulate adipogenesis. Hexapeptide-38 is a PGC1a stimulator (peroxisome proliferator-activated receptor-gamma—PPARγ—coactivator 1 alpha). PGC1a plays a central role in adipogenic activity. See Liang H, Ward W F. PGC-1alpha: a key regulator of energy metabolism. *Adv Physiol Educ.* 2006; 30(4):145-151. Compositions and methods as described herein may comprise a phospholipid delivery system to facilitate penetration and absorption of the materials through the stratum corneum. PGC1a strongly induces in differentiation of preadipocytes into white adipocytes under the influence of PPARγ. The young adipocytes formed under these conditions appear to be small and active, and this size and activity have been seen to be synergistic and in line with good elastin formation. See Ezure T, Amano S. Increment of subcutaneous adipose tissue is associated with decrease of elastic fibres in the dermal layer. *Exp Dermatol.* 2015; 24(12):924-929. As such, large, mature adipocytes have been associated with diminished elastin—manifesting as aged sagging skin—whereas younger, smaller, newly synthesized adipocytes are accompanied by increased elastin levels.

In some embodiments, the compositions as described herein stimulate adipogenesis by at least or about 10%, 15%, 20%, 25%, 30%, 35%, 40%, 45%, 50%, 55% 60%, 65%, 70%, 75%, 80%, 85%, 90%, 95%, or more than 95%. In some embodiments, the compositions as described herein stimulate adipogenesis by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Described herein are compositions and methods resulting in reduced inflammation. Compositions and methods, in some embodiments, comprising phytoene, phytofluene, xylitol, or combinations thereof comprise anti-inflammatory effects.

In some embodiments, the compositions as described herein reduce inflammation by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein reduce inflammation by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

Improvements in bruising, elastin and/or collagen simulation, hyaluronic acid stimulation, adipocyte stimulation, anti-inflammatory effects, or a combination thereof may be determined by comparison to a control. In some embodiments, the control is no treatment. In some embodiments, the control is vehicle treatment. In some embodiments, improvements are measured in a subject who received treatment with a composition described herein on a first portion of the body and vehicle or no treatment on a second portion of the body. For example, improvements are compared between a right arm that is treated with a composition as described herein and a left arm that received vehicle treatment.

Treatment

Compositions as described herein may be used with various treatment regimens. In some instances, the topical compositions described herein are administered once per day, twice per day, three times per day or more. In some instances, the topical compositions described herein are administered twice per day. The topical compositions described herein, in some embodiments, are administered daily, every day, every alternate day, five days a week, once a week, every other week, two weeks per month, three weeks per month, once a month, twice a month, three times per month, or more. In some embodiments, the topical compositions described herein are administered twice daily, e.g., morning and evening. In some embodiments, the topical compositions described herein are administered for at least 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 12 months, 18 months, 2 years, 3 years, 4 years, 5 years, 10 years, or more. In some embodiments, the topical compositions described herein are administered twice daily for at least or about 1 week, 2 weeks, 3 weeks, 1 month, 2 months, 3 months, 4 months, 5 months, 6 months, or more. In some embodiments, the topical compositions described herein are administered once daily, twice daily, three times daily, four times daily, or more than four times daily for at least or about 1 week, 2 weeks, 3 weeks, 1 month, 2 months, 3 months, 4 months, 5 months, 6 months, or more.

In some embodiments, the compositions described herein are used in conjunction with a cosmetic procedure. In some embodiments, the cosmetic procedure comprises injection of a filler.

Compositions as described herein when administered prior to, during, or following injection of a filler may improve bruising, elastin and/or collagen simulation, hyaluronic acid stimulation, adipocyte stimulation, anti-inflammatory effects, or a combination thereof. In some instances, the compositions as described herein improve bruising, elastin and/or collagen simulation, hyaluronic acid stimulation, adipocyte stimulation, anti-inflammatory effects, or a combination thereof by 10%, 15%, 20%, 25%, 30%, 35%, 40%, 45%, 50%, 55%, 60%, 65%, 70%, 75%, 80%, 85%, 90%, 95%, or more than 95% as compared to a control. In some embodiments, the compositions as described herein improve bruising, elastin and/or collagen simulation, hyaluronic acid stimulation, adipocyte stimulation, anti-inflammatory effects, or a combination thereof by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×. In some embodiments, the compositions as described herein improve bruising, elastin and/or collagen simulation, hyaluronic acid stimulation, adipocyte stimulation, anti-inflammatory effects, or a combination thereof following 1 day, 2 days, 3 days, 4 days, 5 days, 6 days, 1 week, 2 weeks, 3 weeks, 1 month, 2 months, or more than 2 months following use of the compositions.

Compositions as described herein used in conjunction with injection of a filler, in some embodiments, improve bruising, elastin and/or collagen simulation, hyaluronic acid stimulation, adipocyte stimulation, anti-inflammatory effects, or a combination thereof following the injection of the filler. In some embodiments, the compositions as described herein improve bruising, elastin and/or collagen simulation, hyaluronic acid stimulation, adipocyte stimulation, anti-inflammatory effects, or a combination thereof by at least or about 10%, 15%, 20%, 25%, 30%, 35%, 40%, 45%, 50%, 55%, 60%, 65%, 70%, 75%, 80%, 85%, 90%, 95%, or more than 95%. In some embodiments, the compositions as described herein improve bruising, elastin and/or collagen simulation, hyaluronic acid stimulation, adipocyte stimulation, anti-inflammatory effects, or a combination thereof by at least or about 0.5×, 1.0×, 1.5×, 2.0×, 2.5×, 3.0×, 3.5×, 4.0×, 5.0×, 6.0×, 7.0×, 8.0×, 9.0×, 10×, or more than 10×.

In some instances, the compositions described herein are administered up to 1 day, up to 2 days, up to 3 days, up to 5 days, up to 6 days, up to 1 week, up to 2 weeks, up to 3 weeks, or more than 3 weeks prior to injection of a filler. In some instances, the compositions described herein are administered immediately prior to injection of a filler, up to 1 hour, up to 2 hours, up to 3 hours, up to 5 hours, up to 6 hours, up to 7 hours, up to 8 hours, up to 12 hours, up to 16 hours, up to 20 hours, or up to 24 hours prior to injection of a filler. Sometimes the compositions described herein are administered singly, or over a time course, such as daily, multiple times weekly, weekly, biweekly, monthly or less frequently prior to injection of a filler. In some instances, the compositions described herein are administered singly, or over a time course, such as daily, multiple times weekly, weekly, biweekly, monthly or more frequently prior to injection of a filler. In some embodiments, the compositions are topical compositions. In some instances, the topical compositions are administered twice daily for at least or about 1 week, 2 weeks, 3 weeks, 1 month, 2 months, 3 months, 4 months, 5 months, 6 months, or more prior to injection of a filler. In some embodiments, the topical compositions described herein are administered once daily, twice daily, three times daily, four times daily, or more than four times daily for at least or about 1 week, 2 weeks, 3 weeks, 1 month, 2 months, 3 months, 4 months, 5 months, 6 months, or more prior to injection of a filler.

In some instances, the compositions described herein are administered up to 1 day, up to 2 days, up to 3 days, up to 5 days, up to 6 days, up to 1 week, up to 2 weeks, up to 3 weeks, or more than 3 weeks prior to a medical or cosmetic procedure described herein or a trauma. In some instances, the compositions described herein are administered immediately prior to the procedure or trauma, up to 1 hour, up to 2 hours, up to 3 hours, up to 5 hours, up to 6 hours, up to 7 hours, up to 8 hours, up to 12 hours, up to 16 hours, up to 20 hours, or up to 24 hours prior to the procedure or trauma. Sometimes the compositions described herein are administered singly, or over a time course, such as daily, multiple times weekly, weekly, biweekly, monthly or less frequently prior to the procedure or trauma. In some instances, the compositions described herein are administered singly, or over a time course, such as daily, multiple times weekly, weekly, biweekly, monthly or more frequently prior to the procedure or trauma. In some embodiments, the compositions are topical compositions. In some instances, the topical compositions are administered twice daily for at least or about 1 week, 2 weeks, 3 weeks, 1 month, 2 months, 3 months, 4 months, 5 months, 6 months, or more the procedure or trauma. In some embodiments, the topical compositions described herein are administered once daily, twice daily, three times daily, four times daily, or more than four times daily for at least or about 1 week, 2 weeks, 3 weeks, 1 month, 2 months, 3 months, 4 months, 5 months, 6 months, or more prior to the procedure or trauma.

In some instances, the compositions described herein are administered up to 1 day, up to 2 days, up to 3 days, up to 5 days, up to 6 days, up to 1 week, up to 2 weeks, up to 3 weeks, or more than 3 weeks following injection of a filler. In some instances, the compositions described herein are administered immediately following injection of a filler, up to 1 hour, up to 2 hours, up to 3 hours, up to 5 hours, up to 6 hours, up to 7 hours, up to 8 hours, up to 12 hours, up to 16 hours, up to 20 hours, or up to 24 hours following injection of a filler. Sometimes the compositions described herein are administered singly, or over a time course, such as daily, multiple times weekly, weekly, biweekly, monthly or less frequently following injection of a filler. In some instances, the compositions described herein are administered singly, or over a time course, such as daily, multiple times weekly, weekly, biweekly, monthly or more frequently following injection of a filler. In some embodiments, the compositions are topical compositions. In some instances, the topical compositions are administered twice daily for at least or about 1 week, 2 weeks, 3 weeks, 1 month, 2 months, 3 months, 4 months, 5 months, 6 months, or more following injection of a filler. In some embodiments, the topical compositions described herein are administered once daily, twice daily, three times daily, four times daily, or more than four times daily for at least or about 1 week, 2 weeks, 3 weeks, 1 month, 2 months, 3 months, 4 months, 5 months, 6 months, or more following injection of a filler.

In some instances, the compositions described herein are administered up to 1 day, up to 2 days, up to 3 days, up to 5 days, up to 6 days, up to 1 week, up to 2 weeks, up to 3 weeks, or more than 3 weeks following a medical or cosmetic procedure described herein or a trauma. In some instances, the compositions described herein are administered immediately following the procedure or trauma, up to 1 hour, up to 2 hours, up to 3 hours, up to 5 hours, up to 6 hours, up to 7 hours, up to 8 hours, up to 12 hours, up to 16 hours, up to 20 hours, or up to 24 hours following the procedure or trauma. Sometimes the compositions described herein are administered singly, or over a time course, such as daily, multiple times weekly, weekly, biweekly, monthly or less frequently following the procedure or trauma. In some instances, the compositions described herein are administered singly, or over a time course, such as daily, multiple times weekly, weekly, biweekly, monthly or more frequently following the procedure or trauma. In some embodiments, the compositions are topical compositions. In some instances, the topical compositions are administered twice daily for at least or about 1 week, 2 weeks, 3 weeks, 1 month, 2 months, 3 months, 4 months, 5 months, 6 months, or more the procedure or trauma. In some embodiments, the topical compositions described herein are administered once daily, twice daily, three times daily, four times daily, or more than four times daily for at least or about 1 week, 2 weeks, 3 weeks, 1 month, 2 months, 3 months, 4 months, 5 months, 6 months, or more following the procedure or trauma.

Stability Testing

Stability testing of the compositions can be conducted as follows.

High temperature testing is now commonly used as a predictor of long-term stability. High temperature testing can be conducted at 37° C. (98° F.) and 45° C. (113° F.). If a product is stored at 45° C. for three months (and exhibits acceptable stability) then it should be stable at room temperature for two years. A good control temperature is 4° C. (39° F.) where most products will exhibit excellent stability. Sometime, the product is also be subjected to −10° C. (14° F.) for three months.

In some instances, stability of the product is assessed by passing three cycles of temperature testing from −10° C. (14° F.) to 25° C. (77° F.). In such cases, the product is placed at −10° C. for 24 hours and then placed at room temperature (25° C.) for 24 hours. This completes one cycle. An even more rigorous test is a −10° C. to 45° C. five-cycle test. This puts emulsions under a tremendous stress.

The dispersed phase (of an oil-in-water emulsion) has a tendency to separate and rise to the top of the emulsion forming a layer of oil droplets. This phenomenon is called creaming. Creaming is one of the first signs of impending emulsion instability. A test method to predict creaming is centrifugation. Heat the emulsion to 50° C. (122° F.) and centrifuge it for thirty minutes at 3000 rpm. Then inspect the resultant product for signs of creaming.

Both formulas and packaging can be sensitive to the UV radiation. The product is placed in glass and the actual package in a light box that has a broad-spectrum output. Another glass jar completely covered with aluminum foil serves as a control. Discoloration of the product may be observed.

For all the above mentioned tests the color, odor/fragrance, viscosity, pH value, and, if available, particle size uniformity and/or particle agglomeration under the microscope can be observed.

Kits for Non-Invasive Use and Use with Invasive Procedures

Some embodiments of the methods and compositions provided herein include kits comprising peptides provided herein. In some embodiments, kits can be provided to an administering physician, other health care professional, a patient, or a caregiver. In some embodiments, a kit comprises a container which contains the peptide compositions in a suitable topical composition, and instructions for administering the peptide composition to a subject. The kit can optionally also contain one or more additional therapeutic or other agents. For example, a kit containing a peptide composition in topical form can be provided along with other skin care agents, such as, cleansers, occlusive moisturizers, penetrating moisturizers, sunscreens, sunblocks, and the like. The kit may contain the peptide composition in bulk form, or can contain separate doses of the peptide composition for serial or sequential administration. The kit can optionally contain one or more diagnostic tools, administration tools, and/or instructions for use. The kit can contain suitable delivery devices, such as, syringes, pump dispensers, single dose packets, and the like, along with instructions for administering the peptide compositions and any other therapeutic or beneficial agents. The kit can optionally contain instructions for storage, reconstitution (if applicable), and administration of any or all therapeutic or beneficial agents included. The kits can include a plurality of containers reflecting the number of administrations to be given to a subject, or the different products to be administered to the subject.

In some embodiments, the composition is configured to support the skin before, during and after cosmetic procedures, and also works with the skin's own natural regenerating process and assists in improving the skin's appearance, and skin tightness. The topical composition can be applied immediately post-procedure for faster recovery, or generally for healthier looking skin. The composition can increase natural levels of elastin in the skin, improves the quality of existing elastin, stimulates increase in collagen production, and exhibits high antioxidant activity to reduce inflammation, redness and irritation. The topical composition is suitable for all skin types and post-procedure skin. The topical compositions can be provided to the patient in bulk form, to permit a suitable amount of the peptides to be self-administered by the patient. For example, the patient can apply an amount of the composition sufficient to provide an even coating over the affected area or as otherwise instructed by the physician. In certain embodiments it can desirable to incorporate additional therapeutic or active agents into the topical composition. Alternatively, adjunct therapies or agents can be administered separately. For example, a cleanser, a sunblock, a sunscreen, a penetrating moisturizer, and/or an occlusive moisturizer can be provided for administration before or after the topical composition of the embodiments.

In one embodiment, a kit is provided for use in connection with a cosmetic skin procedure, as described herein. The kit may include a topical peptide composition, an occlusive moisturizer, a gentle cleanser, a penetrating moisturizer, and a broad spectrum SPF 30+ sunscreen.

The various examples of creams, ointments, lotions, solutions, gels, sprays and patches may incorporate the peptide compositions as described herein as the active ingredient, in combination with penetration enhancing agents and other active agents acting synergistically on the skin for the promotion of wound healing or wound closure or the treatment of chronic cutaneous wound.

NUMBERED EMBODIMENTS

Numbered embodiment 1 comprises a topical composition for improving bruising following injection of a filler comprising: one or more ingredients encapsulated in a liposome a tripeptide-1; and a hexapeptide-12, wherein the topical composition improves healing or appearance of a bruise following injection of the filler. Numbered embodiment 2 comprises the topical composition of numbered embodiment 1, wherein the tripeptide-1 is present at 1-10 ppm. Numbered embodiment 3 comprises the topical composition of numbered embodiments 1-2, wherein the tripeptide-1 comprises palmitoyl tripeptide-1, myristoyl tripeptide-1, or a combination thereof. Numbered embodiment 4 comprises the topical composition of numbered embodiments 1-3, wherein the hexapeptide-12 comprises palmitoyl hexapeptide-12, myristoyl hexapeptide-12, or a combination thereof. Numbered embodiment 5 comprises the topical composition of numbered embodiments 1-4, wherein the hexapeptide-12 is present at 1-10 ppm. Numbered embodiment 6 comprises the topical composition of numbered embodiments 1-5, wherein a first ingredient of the one or more ingredients encapsulated in the liposome is hexapeptide-11. Numbered embodiment 7 comprises the topical composition of numbered embodiments 1-6, wherein the hexapeptide-11 is present at 50-150 ppm. Numbered embodiment 8 comprises the topical composition of numbered embodiments 1-7, wherein a second ingredient of the one or more ingredients encapsulated in the liposome is hexapeptide-38. Numbered embodiment 9 comprises the topical composition of numbered embodiments 1-8, wherein the hexapeptide-38 is acetyl hexapeptide-38. Numbered embodiment 10 comprises the topical composition of numbered embodiments 1-9, further comprising a tetrapeptide. Numbered embodiment 11 comprises the topical composition of numbered embodiments 1-10, wherein the tetrapeptide is tetrapeptide-2. Numbered embodiment 12 comprises the topical composition of numbered embodiments 1-11, wherein the tetrapeptide-2 is acetyl tetrapeptide-2. Numbered embodiment 13 comprises the topical composition of numbered embodiments 1-12, further comprising phosphatidylserine. Numbered embodiment 14 comprises the topical composition of numbered embodiments 1-13, wherein the phosphatidylserine is present at no more than 0.050% by weight (wt. %). Numbered embodiment 15 comprises the topical composition of numbered embodiments 1-14, wherein the phosphatidylserine is present in a range of about 0.005 wt. % to about 0.1 wt. %. Numbered embodiment 16 comprises the topical composition of numbered embodiments 1-15, wherein the phosphatidylserine is present at no more than 5.0 wt %. Numbered embodiment 17 comprises the topical composition of numbered embodiments 1-16, wherein the phosphatidylserine is present at 0.1 wt %. Numbered embodiment 18 comprises the topical composition of numbered embodiments 1-17, wherein a third ingredient of the one or more ingredients encapsulated in the liposome is lactoferrin. Numbered embodiment 19 comprises the topical composition of numbered embodiments 1-18, wherein the lactoferrin is present at no more than 0.050 wt. %. Numbered embodiment 20 comprises the topical composition of numbered embodiments 1-19 wherein the lactoferrin is present in a range of about 0.005 wt. % to about 0.1 wt. %. Numbered embodiment 21 comprises the topical composition of numbered embodiments 1-20, wherein the lactoferrin is present at no more than 5.0 wt %. Numbered embodiment 22 comprises the topical composition of numbered embodiments 1-21, further comprising *Ledum palustre* extract. Numbered embodiment 23 comprises the topical composition of numbered embodiments 1-22, wherein the *Ledum palustre* extract is present in a range of about 0.1 wt. % to about 2.5 wt. %. Numbered embodiment 24 comprises the topical composition of numbered embodiments 1-23, further comprising dill extract. Numbered embodiment 25 comprises the topical composition of numbered embodiments 1-24, wherein the dill extract is present in a range of about 0.01 wt. % to about 2.5 wt. %. Numbered embodiment 26 comprises the topical composition of numbered embodiments 1-25, further comprising hydroxymethoxyphenyl decanone. Numbered embodiment 27 comprises the topical composition of numbered embodiments 1-26 wherein the hydroxymethoxyphenyl decanone is present in a range of about 0.001 wt. % to about 2.5 wt. %. Numbered embodiment 28 comprises the topical composition of numbered embodiments 1-27, further comprising *Tremella fuciformis* extract. Numbered embodiment 29 comprises the topical composition of numbered embodiments 1-28, wherein the *Tremella fuciformis* extract is present in a range of about 0.001 wt. % to about 2.5 wt. %. Numbered embodiment 30 comprises the topical composition of numbered embodiments 1-29, further comprising sodium hyaluronate crosspolymer. Numbered embodiment 31 comprises the topical composition of numbered embodiments 1-30, wherein the sodium hyaluronate crosspolymer is present in a range of about 0.0001 wt. % to about 2.5 wt. %. Numbered embodiment 32 comprises the topical composition of numbered embodiments 1-31, further comprising xylitylglucoside, anhydroxylitol, xylitol, or combinations thereof. Numbered embodiment 33 comprises the topical composition of numbered embodiments 1-32, wherein the xylitylglucoside, anhydroxylitol, xylitol, or combinations thereof is present in a range of about 0.25 wt. % to about 5 wt. %. Numbered embodiment 34 comprises the topical composition of numbered embodiments 1-33, further comprising butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, or combinations thereof. Numbered embodiment 35 comprises the topical composition of numbered embodiments 1-34, wherein the topical composition is aqueous. Numbered embodiment 36 comprises the topical composition of numbered embodiments 1-35, wherein a viscosity of the topical composition is in a range of about 8,000 centipoise (cps) to about 30,000 cps. Numbered embodiment 37 comprises the topical composition of numbered embodiments 1-36, wherein the filler is a soft tissue filler. Numbered embodiment 38 comprises the topical composition of numbered embodiments 1-37, wherein the filler is a dermal filler. Numbered embodiment 39 comprises a topical composition for improving bruising comprising: one or more ingredients encapsulated in a liposome, wherein a first ingredient of the one or more ingredients encapsulated in the liposome is hexapeptide-11; a tripeptide-1; and a hexapeptide-12, wherein the topical composition improves healing or appearance of a bruise. Numbered embodiment 40 comprises the topical composition of numbered embodiments 1-39, wherein the tripeptide-1 is present at 1-10 ppm. Numbered embodiment 41 comprises the topical composition of numbered embodiments 1-40, wherein the tripeptide-1 comprises palmitoyl tripeptide-1, myristoyl tripeptide-1, or a combination thereof. Numbered embodiment 42 comprises the topical composition of numbered embodiments 1-41, wherein the hexapeptide-12 comprises palmitoyl hexapeptide-12, myristoyl hexapeptide-12, or a combination thereof. Numbered embodiment 43 comprises the topical composition of numbered embodiments 1-42, wherein the hexapeptide-12 is present at 1-10 ppm. Numbered embodiment 44 comprises the topical composition of numbered embodiments 1-43, wherein the hexapeptide-11 is present at 50-150 ppm. Numbered embodiment 45 comprises the topical composition of numbered embodiments 1-44, wherein a second ingredient of the one or more ingredients encapsulated in the liposome is hexapeptide-38. Numbered embodiment 46 comprises the topical composition of numbered embodiments 1-45, wherein the hexapeptide-38 is acetyl hexapeptide-38. Numbered embodiment 47 comprises the topical composition of numbered embodiments 1-46, further comprising a tetrapeptide. Numbered embodiment 49 comprises the topical composition of numbered embodiments 1-48, wherein the tetrapeptide is tetrapeptide-2. Numbered embodiment 50 comprises the topical composition of numbered embodiments 1-49, wherein the tetrapeptide-2 is acetyl tetrapeptide-2. Numbered embodiment 51 comprises the topical composition of numbered embodiments 1-50, further comprising phosphatidylserine. Numbered embodiment 52 comprises the topical composition of numbered embodiments 1-51, wherein the phosphatidylserine is present at no more than 0.050% by weight (wt. %). Numbered embodiment 53 comprises the topical composition of numbered embodiments 1-52, wherein the phosphatidylserine is present in a range of about 0.005 wt. % to about 0.1 wt. %. Numbered embodiment 54 comprises the topical composition of numbered embodiments 1-53, wherein the phosphatidylserine is present at no more than 5.0 wt %. Numbered embodiment 55 comprises the topical composition of numbered embodiments 1-54, wherein the phosphatidylserine is present at 0.1 wt %. Numbered embodiment 56 comprises the topical composition of numbered embodiments 1-55, wherein a third ingredient of the one or more ingredients encapsulated in the liposome is lactoferrin. Numbered embodiment 57 comprises the topical composition of numbered embodiments 1-56, wherein the lactoferrin is present at no more than 0.050 wt. %. Numbered embodiment 58 comprises the topical composition of numbered embodiments 1-57, wherein the lactoferrin is present in a range of about 0.005 wt. % to about 0.1 wt. %. Numbered embodiment 59 comprises the topical composition of numbered embodiments 1-58, wherein the lactoferrin is present at no more than 5.0 wt %. Numbered embodiment 60 comprises the topical composition of numbered embodiments 1-59, further comprising *Ledum palustre* extract. Numbered embodiment 61 comprises the topical composition of numbered embodiments 1-60, wherein the *Ledum palustre* extract is present in a range of about 0.1 wt. % to about 2.5 wt. %. Numbered embodiment 62 comprises the topical composition of numbered embodiments 1-61, further comprising dill extract. Numbered embodiment 63 comprises the topical composition of numbered embodiments 1-62, wherein the dill extract is present in a range of about 0.01 wt. % to about 2.5 wt. %. Numbered embodiment 64 comprises the topical composition of numbered embodiments 1-63, further comprising hydroxymethoxyphenyl decanone. Numbered embodiment 65 comprises the topical composition of numbered embodiments 1-64, wherein the hydroxymethoxyphenyl decanone is present in a range of about 0.001 wt. % to about 2.5 wt. %. Numbered embodiment 66 comprises the topical composition of numbered embodiments 1-65, further comprising *Tremella fuciformis* extract. Numbered embodiment 67 comprises the topical composition of numbered embodiments 1-66, wherein the *Tremella fuciformis* extract is present in a range of about 0.001 wt. % to about 2.5 wt. %. Numbered embodiment 68 comprises the topical composition of numbered embodiments 1-67, further comprising sodium hyaluronate crosspolymer. Numbered embodiment 69 comprises the topical composition of numbered embodiments 1-68, wherein the sodium hyaluronate crosspolymer is present in a range of about 0.0001 wt. % to about 2.5 wt. %. Numbered embodiment 70 comprises the topical composition of numbered embodiments 1-69, further comprising xylitylglucoside, anhydroxylitol, xylitol, or combinations thereof. Numbered embodiment 71 comprises the topical composition of numbered embodiments 1-70, wherein the xylitylglucoside, anhydroxylitol, xylitol, or combinations thereof is present in a range of about 0.25 wt. % to about 5 wt. %. Numbered embodiment 72 comprises the topical composition of numbered embodiments 1-71, further comprising butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, or combinations thereof. Numbered embodiment 73 comprises the topical composition of numbered embodiments 1-72, wherein the topical composition is aqueous. Numbered embodiment 74 comprises the topical composition of numbered embodiments 1-73, wherein a viscosity of the topical composition is in a range of about 8,000 centipoise (cps) to about 30,000 cps. Numbered embodiment 75 comprises the topical composition of numbered embodiments 1-74, wherein the bruise appears following a cosmetic procedure. Numbered embodiment 76 comprises the topical composition of numbered embodiments 1-75, wherein the cosmetic procedure is an injection of a filler. Numbered embodiment 77 comprises the topical composition of numbered embodiments 1-76, wherein the cosmetic procedure is an injection of a neurotoxin. Numbered embodiment 781 comprises the topical composition of numbered embodiments 1-77, wherein the cosmetic procedure is an invasive surgery. Numbered embodiment 79 comprises the topical composition of numbered embodiments 1-78, wherein the bruise appears following a medical procedure. Numbered embodiment 80 comprises the topical composition of numbered embodiments 1-79, wherein the medical procedure is a therapeutic injection. Numbered embodiment 81 comprises the topical composition of numbered embodiments 1-80, wherein the medical procedure is an intravenous injection. Numbered embodiment 82 comprises the topical composition of numbered embodiments 1-81, wherein the medical procedure is an invasive surgery. Numbered embodiment 83 comprises the topical composition of numbered embodiments 1-82, wherein the bruise appears following a trauma. Numbered embodiments 84 comprises a topical composition for rejuvenating skin comprising a liposome encapsulating: one or more peptides; and lactoferrin, wherein the topical composition rejuvenates skin. Numbered embodiment 85 comprises the topical composition of numbered embodiments 1-84, further comprising tripeptide-1. Numbered embodiment 86 comprises the topical composition of numbered embodiments 1-85, wherein the tripeptide is tripeptide-1. Numbered embodiment 87 comprises the topical composition of numbered embodiments 1-86, wherein the tripeptide-1 is present at 1-10 ppm. Numbered embodiment 88 comprises the topical composition of numbered embodiments 1-87, wherein the tripeptide-1 comprises palmitoyl tripeptide-1, myristoyl tripeptide-1, or a combination thereof. Numbered embodiment 89 comprises the topical composition of numbered embodiments 1-88, further comprising hexapeptide-12. Numbered embodiment 90 comprises the topical composition of numbered embodiments 1-89, wherein the hexapeptide-12 comprises palmitoyl hexapeptide-12, myristoyl hexapeptide-12, or a combination thereof. Numbered embodiment 91 comprises the topical composition of numbered embodiments 1-90, wherein the hexapeptide-12 is present at 1-10 ppm. Numbered embodiment 92 comprises the topical composition of numbered embodiments 1-91, wherein a first peptide of the one or more peptides comprises hexapeptide-11. Numbered embodiment 93 comprises the topical composition of numbered embodiments 1-92, wherein the hexapeptide-11 is present at 50-150 ppm. Numbered embodiment 94 comprises the topical composition of numbered embodiments 1-93, wherein a second peptide of the one or more peptides comprises hexapeptide-38. Numbered embodiment 95 comprises the topical composition of numbered embodiments 1-94, wherein the hexapeptide-38 is acetyl hexapeptide-38. Numbered embodiment 96 comprises the topical composition of numbered embodiments 1-95, further comprising a tetrapeptide. Numbered embodiment 97 comprises the topical composition of numbered embodiments 1-96, wherein the tetrapeptide is tetrapeptide-2. Numbered embodiment 948 comprises the topical composition of numbered embodiments 1-97, wherein the tetrapeptide-2 is acetyl tetrapeptide-2. Numbered embodiment 99 comprises the topical composition of numbered embodiments 1-98, further comprising phosphatidylserine. Numbered embodiment 100 comprises the topical composition of numbered embodiments 1-99, wherein the phosphatidylserine is present at no more than 0.050% by weight (wt. %). Numbered embodiment 101 comprises the topical composition of numbered embodiments 1-100, wherein the phosphatidylserine is present in a range of about 0.005 wt. % to about 0.1 wt. %. Numbered embodiment 102 comprises the topical composition of numbered embodiments 1-101, wherein the phosphatidylserine is present at no more than 5.0 wt %. Numbered embodiment 103 comprises the topical composition of numbered embodiments 1-102, wherein the phosphatidylserine is present at 0.1 wt %. Numbered embodiment 104 comprises the topical composition of numbered embodiments 1-103, wherein the lactoferrin is present at no more than 0.050 wt. %. Numbered embodiment 105 comprises the topical composition of numbered embodiments 1-104, wherein the lactoferrin is present in a range of about 0.005 wt. % to about 0.1 wt. %. Numbered embodiment 106 comprises the topical composition of numbered embodiments 1-105, wherein the lactoferrin is present at no more than 5.0 wt %. Numbered embodiment 107 comprises the topical composition of numbered embodiments 1-106, further comprising *Ledum palustre* extract. Numbered embodiment 108 comprises the topical composition of numbered embodiments 1-107, wherein the *Ledum palustre* extract is present in a range of about 0.1 wt. % to about 2.5 wt. %. Numbered embodiment 109 comprises the topical composition of numbered embodiments 1-108, further comprising dill extract. Numbered embodiment 110 comprises the topical composition of numbered embodiments 1-109, wherein the dill extract is present in a range of about 0.01 wt. % to about 2.5 wt. %. Numbered embodiment 111 comprises the topical composition of numbered embodiments 1-110, further comprising hydroxymethoxyphenyl decanone. Numbered embodiment 112 comprises the topical composition of numbered embodiments 1-111, wherein the hydroxymethoxyphenyl decanone is present in a range of about 0.001 wt. % to about 2.5 wt. %. Numbered embodiment 113 comprises the topical composition of numbered embodiments 1-112, further comprising *Tremella fuciformis* extract. Numbered embodiment 114 comprises the topical composition of numbered embodiments 1-113, wherein the *Tremella fuciformis* extract is present in a range of about 0.001 wt. % to about 2.5 wt. %. Numbered embodiment 115 comprises the topical composition of numbered embodiments 1-114, further comprising sodium hyaluronate crosspolymer. Numbered embodiment 116 comprises the topical composition of numbered embodiments 1-114, wherein the sodium hyaluronate crosspolymer is present in a range of about 0.0001 wt. % to about 2.5 wt. %. Numbered embodiment 116 comprises the topical composition of numbered embodiments 1-115, further comprising xylitylglucoside, anhydroxylitol, xylitol, or combinations thereof. Numbered embodiment 117 comprises the topical composition of numbered embodiments 1-116, wherein the xylitylglucoside, anhydroxylitol, xylitol, or combinations thereof is present in a range of about 0.25 wt. % to about 5 wt. %. Numbered embodiment 118 comprises the topical composition of numbered embodiments 1-117, further comprising butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxyethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, or combinations thereof. Numbered embodiment 119 comprises the topical composition of numbered embodiments 1-118, wherein the topical composition is aqueous. Numbered embodiment 120 comprises the topical composition of numbered embodiments 1-119, wherein a viscosity of the topical composition is in a range of about 8,000 centipoise (cps) to about 30,000 cps. Numbered embodiment 121 comprises a method for improving bruising in an individual, comprising administering a topical composition of the numbered embodiments 1-120. Numbered embodiment 122 comprises the method of numbered embodiments 1-121, wherein the bruising is improved by at least 5%10%, 15%, 20%, 25%, 30%, 40%, 50%, 60%, 70%, 80%, 90%, or more than 90%. Numbered embodiment 123 comprises the method of numbered embodiments 1-122, wherein the bruising is improved by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×. Numbered embodiment 124 comprises the method of numbered embodiments 1-123, wherein the bruising is improved at least 1 day after administering the topical composition. Numbered embodiment 125 comprises the method of numbered embodiments 1-124, wherein the bruising is improved at least 2 days after administering the topical composition. Numbered embodiment 126 comprises the method of numbered embodiments 1-125, wherein improvements in bruising comprises accelerated resolution of a bruise, reduced size of a bruise, reduced discoloration of skin, reduced swelling, or combinations thereof. Numbered embodiment 127 comprises a method for improving macrophage function in an individual, comprising administering a topical composition of any one of numbered embodiments 1-126. Numbered embodiment 128 comprises the method of numbered embodiments 1-127, wherein the improved macrophage function comprises improved phagocytosis. Numbered embodiment 129 comprises the method of numbered embodiments 1-128, wherein the improved macrophage function comprises improved hemosiderin clearance. Numbered embodiment 130 comprises the method of numbered embodiments 1-129, wherein the macrophage function is improved by at least 5%, 10%, 15%, 20%, 25%, 30%, 40%, 50%, 60%, 70%, 80%, 90%, or more than 90%. Numbered embodiment 131 comprises the method of numbered embodiments 1-130, wherein the macrophage function is improved by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×. Numbered embodiment 132 comprises a method for stimulating production of elastin, collagen, or a combination thereof in an individual, comprising administering a topical composition of the numbered embodiments 1-131. Numbered embodiment 133 comprises the method of numbered embodiments 1-132, wherein the production of elastin, collagen, or a combination thereof is stimulated by at least 5%, 10%, 15%, 20%, 25%, 30%, 40%, 50%, 60%, 70%, 80%, 90%, or more than 90%. Numbered embodiment 134 comprises the method of numbered embodiments 1-133, wherein the production of elastin, collagen, or a combination thereof is stimulated by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×. Numbered embodiment 135 comprises a method for stimulating intrinsic hyaluronic acid production in an individual, comprising administering a topical composition of the numbered embodiments 1-134. Numbered embodiment 136 comprises the method of numbered embodiments 1-135, wherein the intrinsic hyaluronic acid production is stimulated by at least 5%, 10%, 15%, 20%, 25%, 30%, 40%, 50%, 60%, 70%, 80%, 90%, or more than 90%. Numbered embodiment 137 comprises the method of numbered embodiments 1-136, wherein the intrinsic hyaluronic acid production is stimulated by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×. Numbered embodiment 138 comprises a method for increasing adipogenesis in an individual, comprising administering a topical composition of the numbered embodiments 1-137. Numbered embodiment 139 comprises the method of numbered embodiments 1-138, wherein adipogenesis is increased by at least 5%, 10%, 15%, 20%, 25%, 30%, 40%, 50%, 60%, 70%, 80%, 90%, or more than 90%. Numbered embodiment 140 comprises the method of numbered embodiments 1-139, wherein adipogenesis is increased by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×. Numbered embodiment 141 comprises a method for reducing inflammation in an individual, comprising administering a topical composition of the numbered embodiments 1-140. Numbered embodiment 142 comprises the method of numbered embodiments 1-141, wherein inflammation is reduced by at least 5%10%, 15%, 20%, 25%, 30%, 40%, 50%, 60%, 70%, 80%, 90%, or more than 90%. Numbered embodiment 143 comprises the method of numbered embodiments 1-142, wherein inflammation is reduced by at least 0.5×, 1.0×, 1.5×, 2.0×, 2.5×, 3.0×, 3.5×, 4.0×, 5.0×, 6.0×, 7.0×, 8.0×, 9.0×, 10×, or more than 10×. Numbered embodiment 144 comprises the method of numbered embodiments 1-143, wherein the topical composition is administered following a cosmetic procedure. Numbered embodiment 145 comprises the method of numbered embodiments 1-144, wherein the topical composition is administered prior to a cosmetic procedure. Numbered embodiment 146 comprises the method of numbered embodiments 1-145, wherein the cosmetic procedure comprises injection of a filler. Numbered embodiment 147 comprises the method of numbered embodiments 1-146, wherein the filler is a soft tissue filler. Numbered embodiment 148 comprises the method of numbered embodiments 1-147, wherein the filler is a dermal filler. Numbered embodiment 149 comprises the method of numbered embodiments 1-148, wherein the cosmetic procedure is a microneedling procedure. Numbered embodiment 150 comprises the method of numbered embodiments 1-149, wherein the microneedling procedure is a radiofrequency microneedling procedure. Numbered embodiment 151 comprises the method of numbered embodiments 1-150, wherein the topical composition is administered at least 1 day prior to the microneedling procedure. Numbered embodiment 152 comprises the method of numbered embodiments 1-151, wherein the topical composition is administered at least 1 week prior to the microneedling procedure. Numbered embodiment 153 comprises the method of numbered embodiments 1-152, wherein the topical composition is administered at least 2 weeks prior to the microneedling procedure. Numbered embodiment 154 comprises the method of numbered embodiments 1-153, wherein the topical composition is administered at least 1 day following the microneedling procedure. Numbered embodiment 155 comprises the method of numbered embodiments 1-154, wherein the topical composition is administered at least 1 week following the microneedling procedure. Numbered embodiment 156 comprises the method of numbered embodiments 1-155, wherein the topical composition is administered at least 2 weeks following the microneedling procedure. Numbered embodiment 157 comprises the method of numbered embodiments 1-156, wherein the topical composition is administered immediately prior to the injection of the filler. Numbered embodiment 158 comprises the method of numbered embodiments 1-157, wherein the topical composition is administered at least 1 day prior to the injection of the filler. Numbered embodiment 159 comprises the method of numbered embodiments 1-158, wherein the topical composition is administered at least 1 week prior to the injection of the filler. Numbered embodiment 160 comprises the method of numbered embodiments 1-159, wherein the topical composition is administered at least 2 weeks prior to the injection of the filler. Numbered embodiment 161 comprises the method of numbered embodiments 1-160, wherein the topical composition is administered immediately following the injection of the filler. Numbered embodiment 162 comprises the method of numbered embodiments 1-161, wherein the topical composition is administered at least 1 day following the injection of the filler. Numbered embodiment 163 comprises the method of numbered embodiments 1-162, wherein the topical composition is administered at least 1 week following the injection of the filler. Numbered embodiment 164 comprises the method of numbered embodiments 1-163, wherein the topical composition is administered at least 2 weeks following the injection of the filler. Numbered embodiment 165 comprises the method of numbered embodiments 1-164, wherein the cosmetic procedure is an injection of a neurotoxin. Numbered embodiment 166 comprises the method of numbered embodiments 1-165, wherein the cosmetic procedure is an invasive surgery. Numbered embodiment 167 comprises the method of numbered embodiments 1-166, wherein the topical composition is administered following a medical procedure. Numbered embodiment 168 comprises the method of numbered embodiments 1-167, wherein the topical composition is administered prior to a medical procedure. Numbered embodiment 169 comprises the method of numbered embodiments 1-168, wherein the medical procedure is a therapeutic injection. Numbered embodiment 170 comprises the method of numbered embodiments 1-169, wherein the medical procedure is an intravenous injection. Numbered embodiment 171 comprises the method of numbered embodiments 1-170, wherein the medical procedure is an invasive surgery. Numbered embodiment 172 comprises the method of numbered embodiments 1-171, wherein the topical composition is administered following a trauma. Numbered embodiment 173 comprises the method of numbered embodiments 1-172, wherein the topical composition is administered prior to a trauma. Numbered embodiment 174 comprises the method of numbered embodiments 1-173, wherein the topical composition is administered 1, 2, 3, 4, 5, 6, 7, or 8 times a day. Numbered embodiment 175 comprises the method of numbered embodiments 1-174, wherein the topical composition is administered 4 times a day. Numbered embodiment 176 comprises the method of numbered embodiments 1-175, wherein the individual is a human.

EXAMPLES

The following examples are given for the purpose of illustrating various embodiments of the disclosure and are not meant to limit the present disclosure in any fashion. The present examples, along with the methods described herein are presently representative of preferred embodiments, are exemplary, and are not intended as limitations on the scope of the disclosure. Changes therein and other uses which are encompassed within the spirit of the disclosure as defined by the scope of the claims will occur to those skilled in the art.

Example 1: Exemplary Compositions

An exemplary composition is seen in Table 1.

TABLE 1

| Ingredient | % by wt. |
| --- | --- |
| Butylene Glycol, Aqua, Acetyl Hexapeptide-38 | 0.05-1.25 |
| Xylitylglucoside, Anhydroxylitol, Xylitol | 0.2-5 |
| Water, Butylene Glycol, Arnica Montana Flower Extract | 0.1-2.5 |
| Glycerin, Palmitoyl Tripeptide-1 | 0.5-15 |
| Glycerin, Palmitoyl Hexapeptide-12 | 0.5-15 |
| Hexapeptide-11 | 0.001-0.025 |
| Sodium Hyaluronate Crosspolymer | 0.1-2.5 |
| Squalane, Dunaliella Salina Extract | 0.1-2.5 |
| Ledum Palustre (Labrador Tea) Extract, Radish Root Ferment Filtrate | 0.1-2.5 |
| Lactoferrin | 0.01-0.25 |
| Phosphatidylserine, Phospholipids, Tocopherol, Ascorbyl Palmitate | 0.02-0.5 |
| Aqua, Butylene Glycol, Peucedanum Graveolens (Dill) Extract, Xanthan Gum | 0.1-2.5 |
| Water, Tremella Fuciformis Sporocarp (Silver Ear Mushroom) Extract, Betaine, Glycerin | 0.1-2.5 |
| Propanediol, Lecithin | 0.4-10 |
| Caprylic/Capric Triglyceride, Hydroxymethoxyphenyl Decanone | 0.1-2.5 |

TABLE 1-continued

| Ingredient | % by wt. |
| --- | --- |
| Water, Acetyl Tetrapeptide-2, Caprylyl Glycol | 0.2-5 |
| Caprylic/Capric Triglyceride | 0.4-10 |
| Caprylyl Methicone | 0.1-2.5 |
| Water/Aqua/Eau | 40-90 |
| Phenoxyethanol, Ethylhexylglycerin | 0.17-4.25 |
| Polyacrylate-13, Polyisobutene, Polysorbate 20 | 0.5-12.5 |
| Caprylyl Glycol, Caprylhydroxamic Acid, Glycerin | 0.1-2.5 |
| Disodium EDTA | 0.02-0.5 |
| Propanediol | 0.04-1 |

Example 2: Macrophage Phagocytosis of Red Blood Cells

Macrophage phagocytosis of red blood cells was measured to determine the effects of peptides and various reagents in hemosiderin clearance.

Figure 1B:
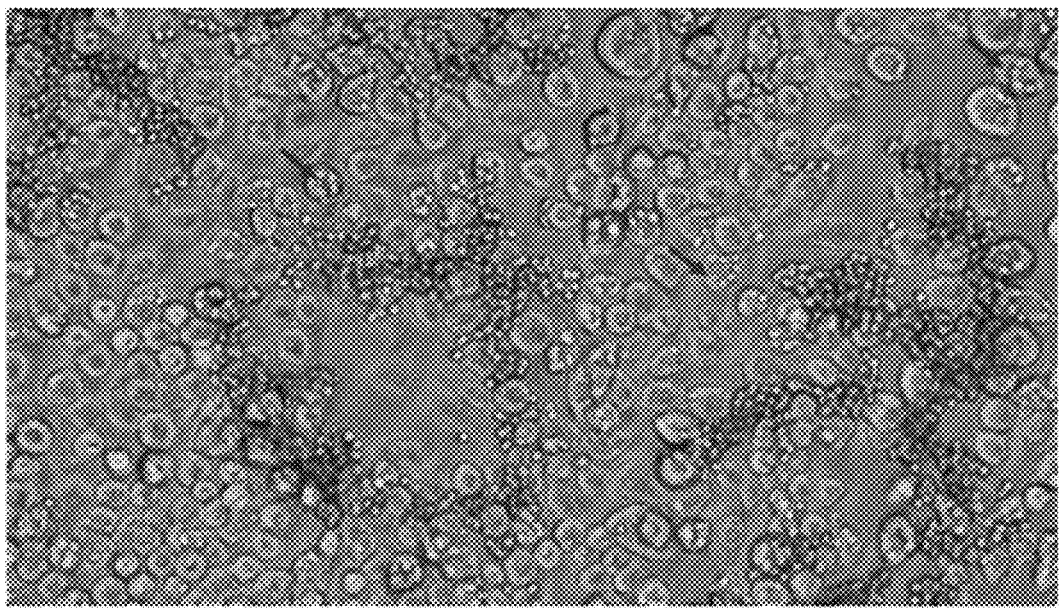
FIG. 1B illustrates macrophage phagocytosis prior to red blood cell washout.
Figure 1C:
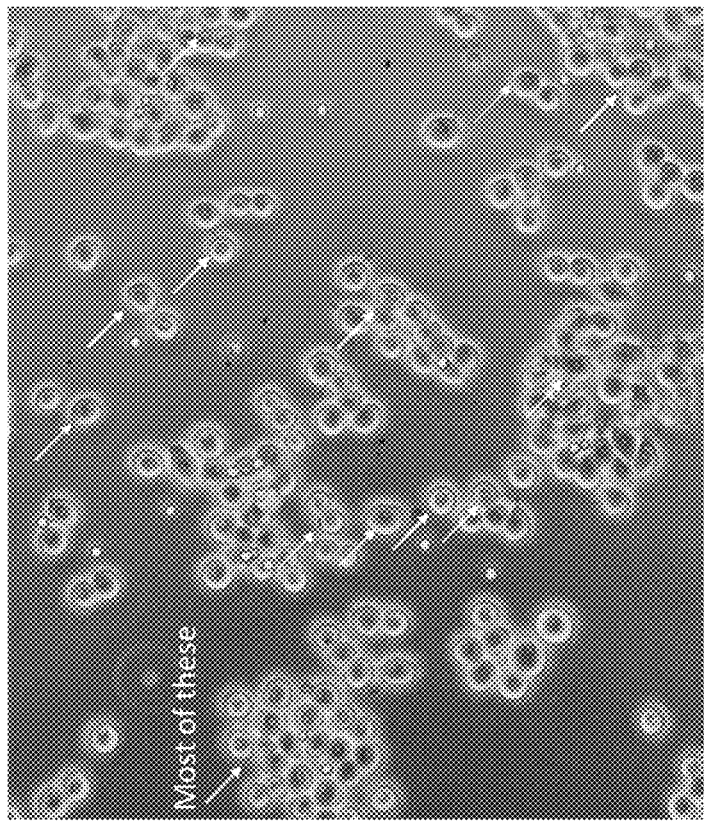
FIG. 1C illustrates macrophage phagocytosis following red blood cell washout.
Figure 1C:
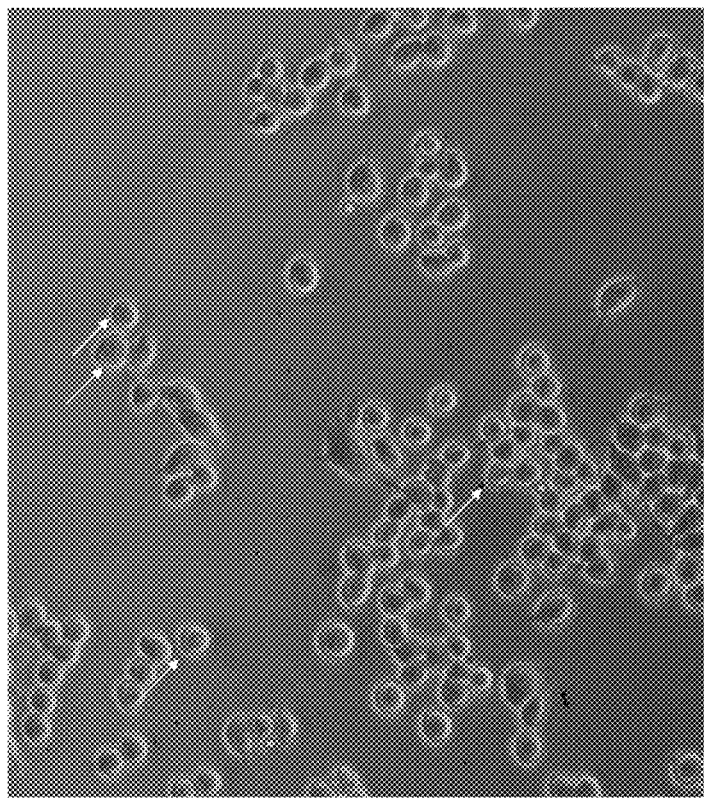

FIG. 1A shows a schematic of the macrophage phagocytosis assay. The assay was performed according to manufacturer's instructions (Cell BioLabs, Inc.). Macrophages used were RAW-Difluo mLC3 autophagy reporter cells. Human red blood cells (RBCs) were obtained from ZenBio (catalog number SER-10MLRBC). Briefly, 24 hours before the assay, macrophages were plated on 96-well plates. One plate was plated with 12,500 macrophages and a second plate with 25,000 macrophages. The day of the assay, human red blood cells (RBCs) were opsonized with human RBC antibody. As a negative control, sheep RBCs were opsonized with human RBC antibody. The media was then replaced with either peptide or no peptide. Blood was added to the plates at a 200:1 RBC to macrophage ratio. Phagocytosis was measured beginning at 2 hours after blood was added. The media and blood were removed from the wells of the plate. The plate was washed once with RBC lysis buffer to remove non-phagocytosed RBCs followed by two washes with PBS. Macrophage lysis buffer was then added to the plate and the lysed solution was transferred to a 96-well plate. The substrate solution to detect heme was added to the 96-well plate and absorbance was recorded at 1 minute, 5 minutes, 10, minutes, and 20 minutes. FIGS. 1B-1C show images of macrophage phagocytosis prior to red blood cell (RBC) washout (FIG. 1B) and after RBC washout (FIG. 1C). Arrows indicate macrophages with RBCs (hollow circles). Macrophages without RBCs are seen as dark central nuclei.

Figure 2:
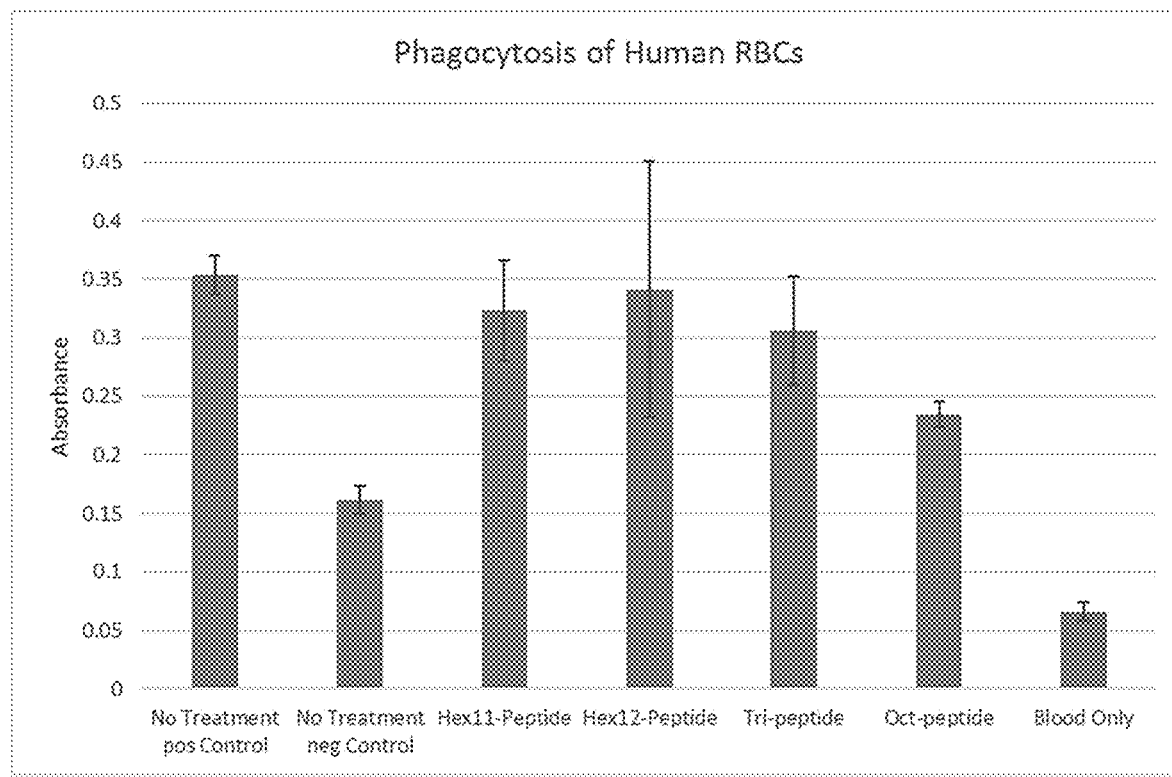
FIG. 2 illustrates a graph of phagocytosis of human red blood cells (RBCs) with the following groups: no treatment positive control, no treatment negative control, hexapeptide- 11 (Hex11-Peptide), hexapeptide-12 (Hex12-peptide), tripeptide-1 (Tri-peptide), Oct-peptide, and blood only.

The assay was validated and data is seen in FIG. 2. FIG. 2 shows the following groups: no treatment positive control, no treatment negative control, hexapeptide-11 (Hex11-Peptide), hexapeptide-12 (Hex12-peptide), tripeptide-1 (Tripeptide), Oct-peptide, and blood only. The no treatment positive control comprised macrophages and human blood (human antibody). The no treatment negative control comprised macrophages and human blood (sheep antibody). The peptide treatments (hexapeptide-11, hexapeptide-12, tripeptide-1, and Oct-peptide) were done with macrophages and human blood (human antibody). Blood only treatment was performed with no macrophages and to assess the efficiency of washing out RBCs. Absorbance was recorded 2 hours after RBC addition. As seen in FIG. 2, the no treatment negative control was half of the no treatment positive control. Further as seen in FIG. 2, the RBC wash steps removed almost all non-phagocytosed blood.

Figure 3A:
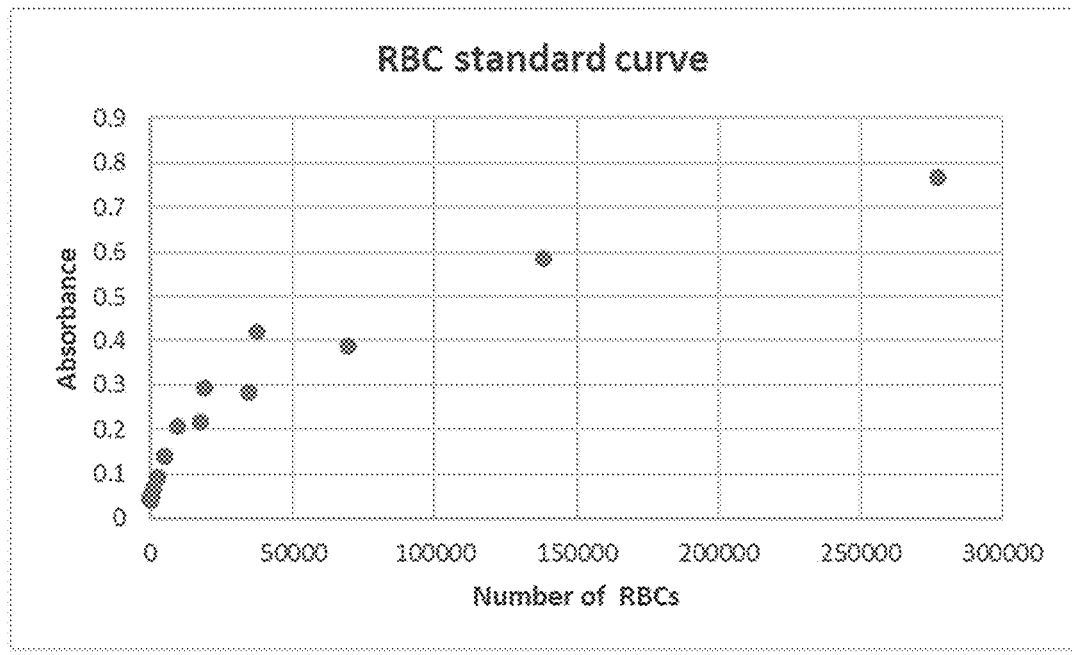
FIG. 3A illustrates a graph of a red blood cell (RBC) standard curve with absorbance on the y-axis and number of RBCs on the x-axis.
Figure 3B:
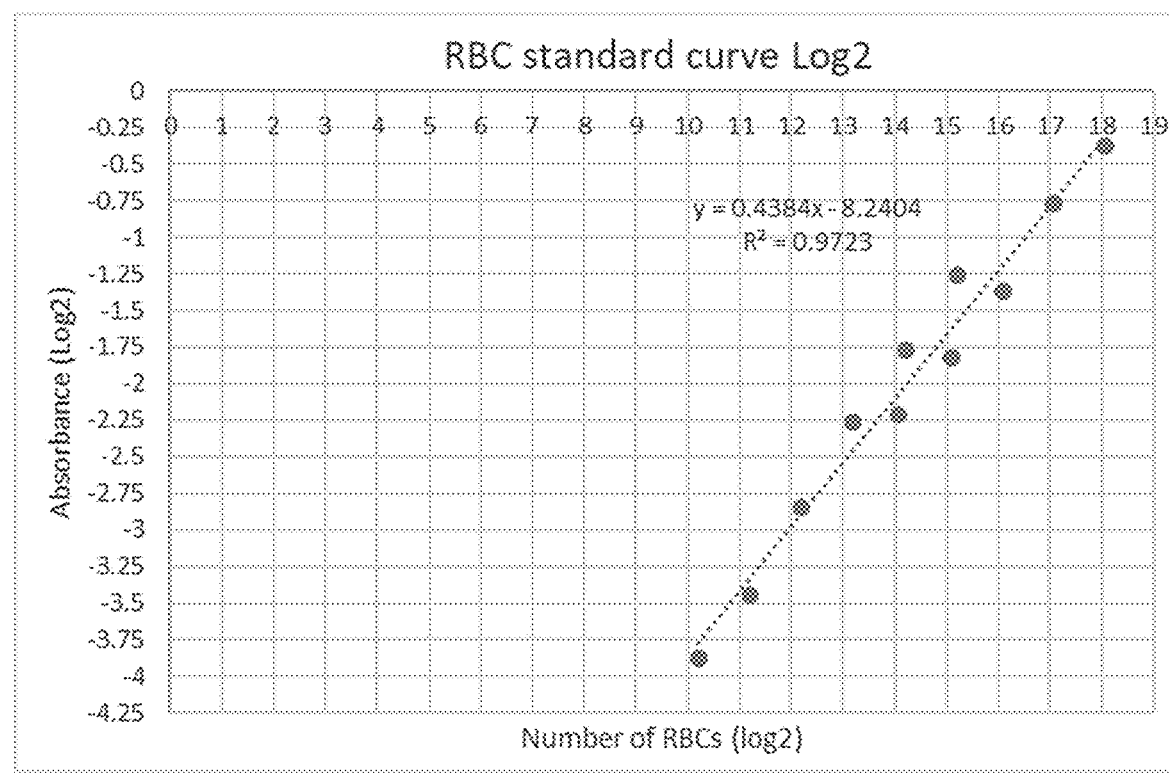
FIG. 3B illustrates a graph of red blood cell (RBC) standard curve (log 2) with absorbance (log 2) on the y-axis and number of RBCs (log 2) on the x-axis.

A red blood cell (RBC) curve was performed to quantitate the number of RBCs that are phagocytosed in an assay, which was used to extrapolate number of RBCs from an absorbance value (FIGS. 3A-3B). FIG. 3A shows a graph of a RBC standard curve with absorbance on the y-axis and number of RBCs on the x-axis. FIG. 3B shows a graph of RBC standard curve (log 2) with absorbance (log 2) on the y-axis and number of RBCs (log 2) on the x-axis.

Figure 4:
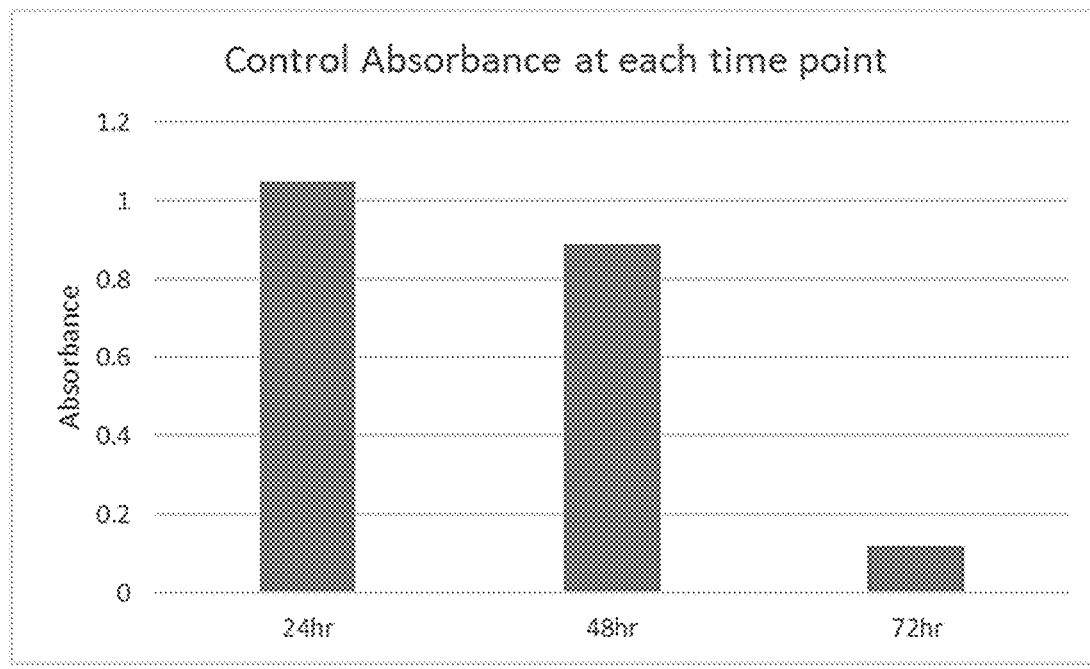
FIG. 4 illustrates a graph of absorbance for no treatment control samples with absorbance on the y-axis and time (24 hours, 48 hours, and 72 hours) on the x-axis.

A time course was performed to determine at which time to study phagocytosis. FIG. 4 shows a graph of absorbance for no treatment control samples with absorbance on the y-axis and time (24 hours, 48 hours, and 72 hours) on the x-axis. At 24 hours, most red blood cells (RBCs) were phagocytosed. At 48 hours, almost all RBCs were phagocytosed and were starting to be degraded. At 72 hours, all RBCs were phagocytosed and degraded. Therefore, 24 hours was chosen for subsequent experiments.

Phagocytosis Following Various Treatments

Phagocytosis of red blood cells (RBCs) was performed after various treatments. Briefly, 24 hours before the phagocytosis assay, 25,000 macrophages were plated onto a 96-well plate. On the day of the assay, the media was replaced with the various peptide or compound treatments. RBCs were then added to macrophages at a 100:1 RBC to macrophage ratio. The cells were then incubated at 37° C. and 5% $CO_2$. After 24 hours the non-phagocytosed RBCs were washed away, macrophages lysed, and heme assay substrate added to detect absorbed RBCs/heme 15 minutes later. Concentrations of the peptides included the following: 2.9 ug/mL of tripeptide-1, 100 ug/mL of hexapeptide-11, and 2.9 ug/mL of hexapeptide-12. Comparisons of lactoferrin and phosphatidylserine were relative to no treatment (NT) PBS control. Each 0.1 increment on the y-axis demonstrates a 10% increase in efficacy of macrophage function representing significant increase in RBC phagocytosis.

Figure 5:
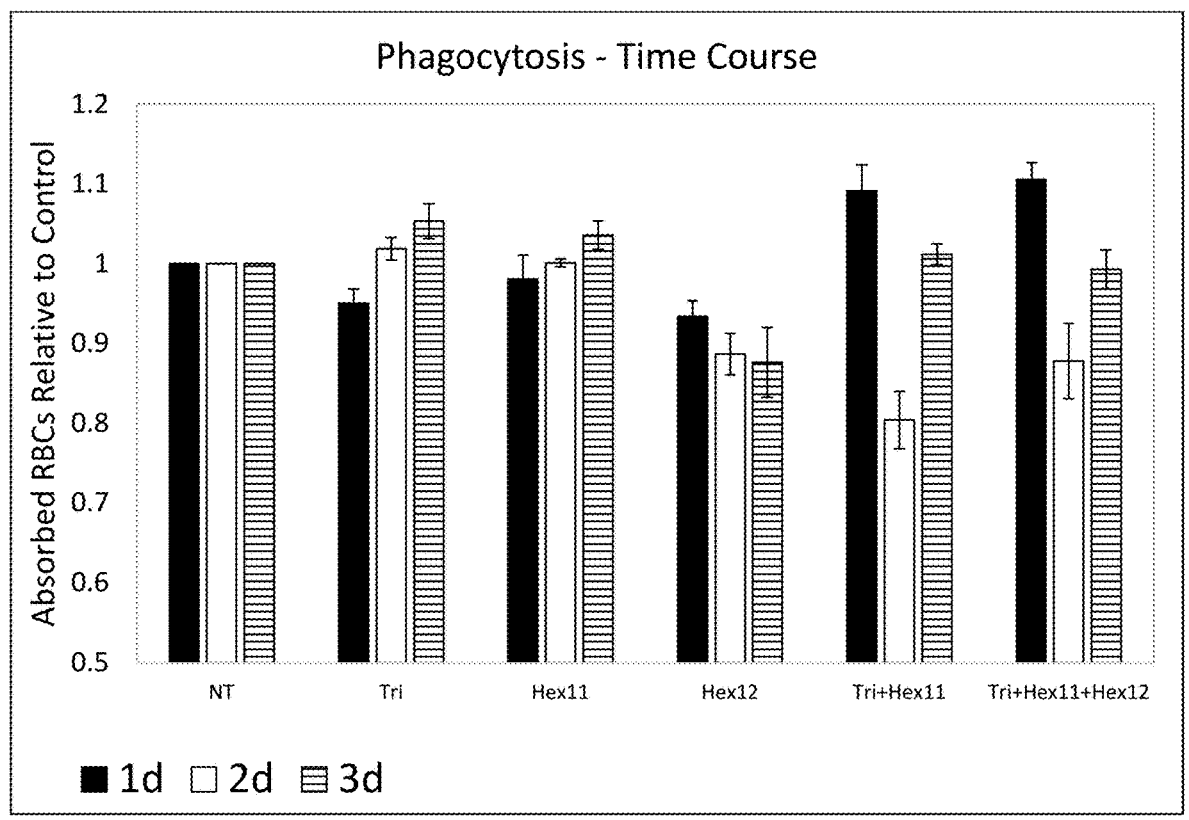
FIG. 5 illustrates a graph of a time course of phagocytosis following various treatments. The treatments included the following: no treatment (NT), tripeptide-1 (Tri), hexapeptide-11 (Hex11), hexapeptide-12 (Hex12), tripeptide-1 and hexapeptide-11 (Tri+Hex11), and tripeptide-1, hexapeptide-11, and hexapeptide-12 (Tri+Hex11+Hex12).

FIG. 5 shows a time course of phagocytosis following various treatments. The treatments included the following: no treatment (NT), tripeptide-1 (Tri), hexapeptide-11 (Hex11), hexapeptide-12 (Hex12), tripeptide-1 and hexapeptide-11 (Tri+Hex11), and tripeptide-1, hexapeptide-11, and hexapeptide-12 (Tri+Hex11+Hex12) A time course was performed over 24 hours (1 d, black bars), 48 hours (2d, white bars), and 72 hours (3d, horizontal bars). At 24 hours, the peptide-combination treatments showed the highest increase in phagocytosis. The 24 hour time point was used for the experiments described below.

Figure 6:
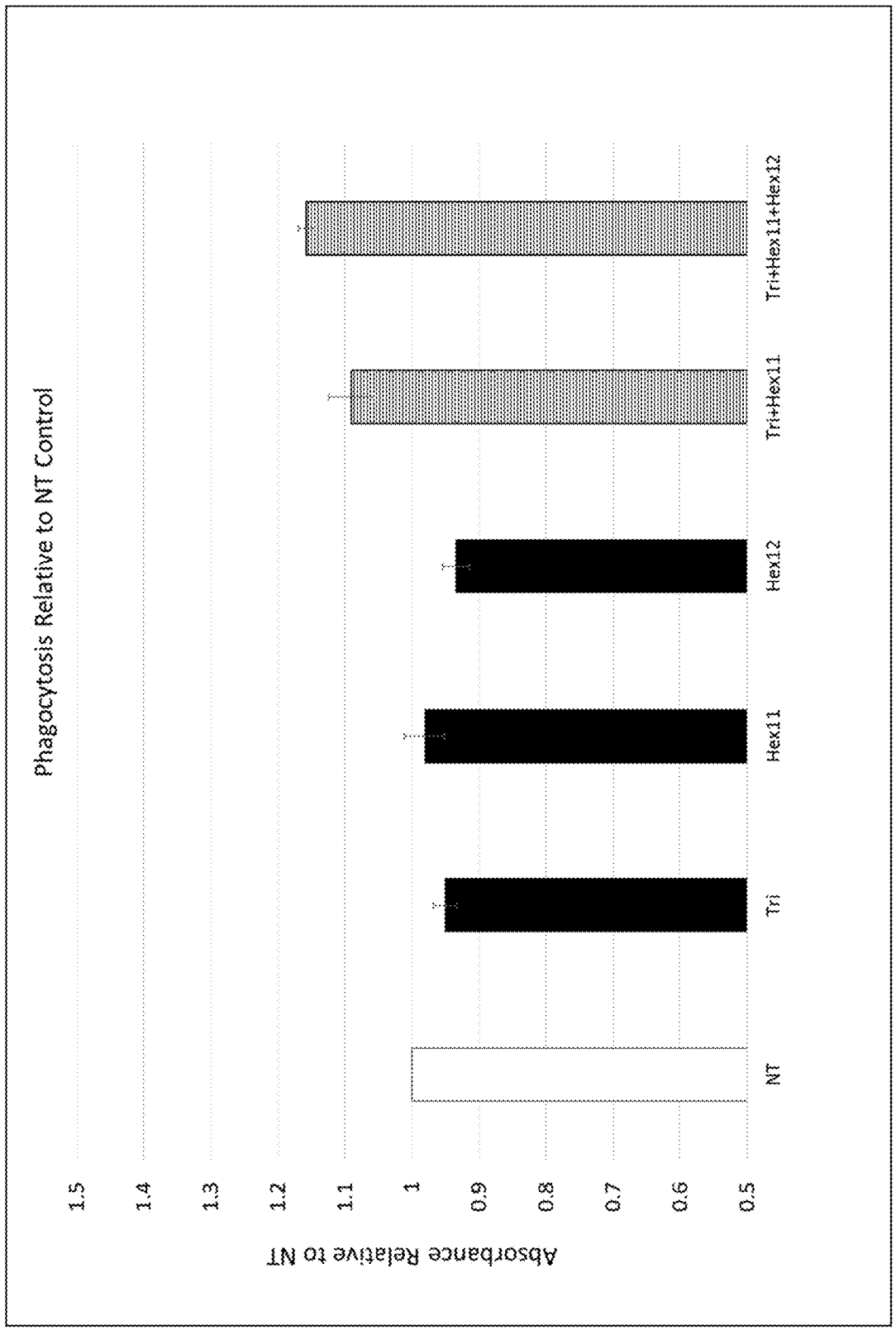
FIG. 6 illustrates a graph of phagocytosis following various treatments including: No treatment (NT), tripeptide-1 (Tri), hexapeptide-11 (Hex11), hexapeptide-12 (Hex12), tripeptide-1 and hexapeptide-11 (Tri+Hex11), and tripeptide-1, hexapeptide-11, and hexapeptide-12 (Tri+Hex11+Hex12).

Effects of various peptide treatments on phagocytosis were then determined. FIG. 6 shows the various peptide treatments on phagocytosis including: No treatment (NT, white bars), tripeptide-1 (Tri, black bar), hexapeptide-11 (Hex11, black bar), hexapeptide-12 (Hex12, black bar), tripeptide-1 and hexapeptide-11 (Tri+Hex11, horizontal bar), and tripeptide-1, hexapeptide-11, and hexapeptide-12 (Tri+Hex11+Hex12, horizontal bar). As seen in FIG. 6, peptide treatment alone (tripeptide-1, hexapeptide-11, and hexapeptide-12) showed a decrease or no change in phagocytosis relative to NT control. Tripeptide-1 and hexapeptide-11 treatment as well as tripeptide-1, hexapeptide-11, and hexapeptide-12 treatment resulted in an increase in efficacy around 15% (3×-4× change) as compared to peptide treatment alone, demonstrating synergy of combining peptides in macrophage phagocytosis of red blood cells and dissolution of bruising.

Figure 7:
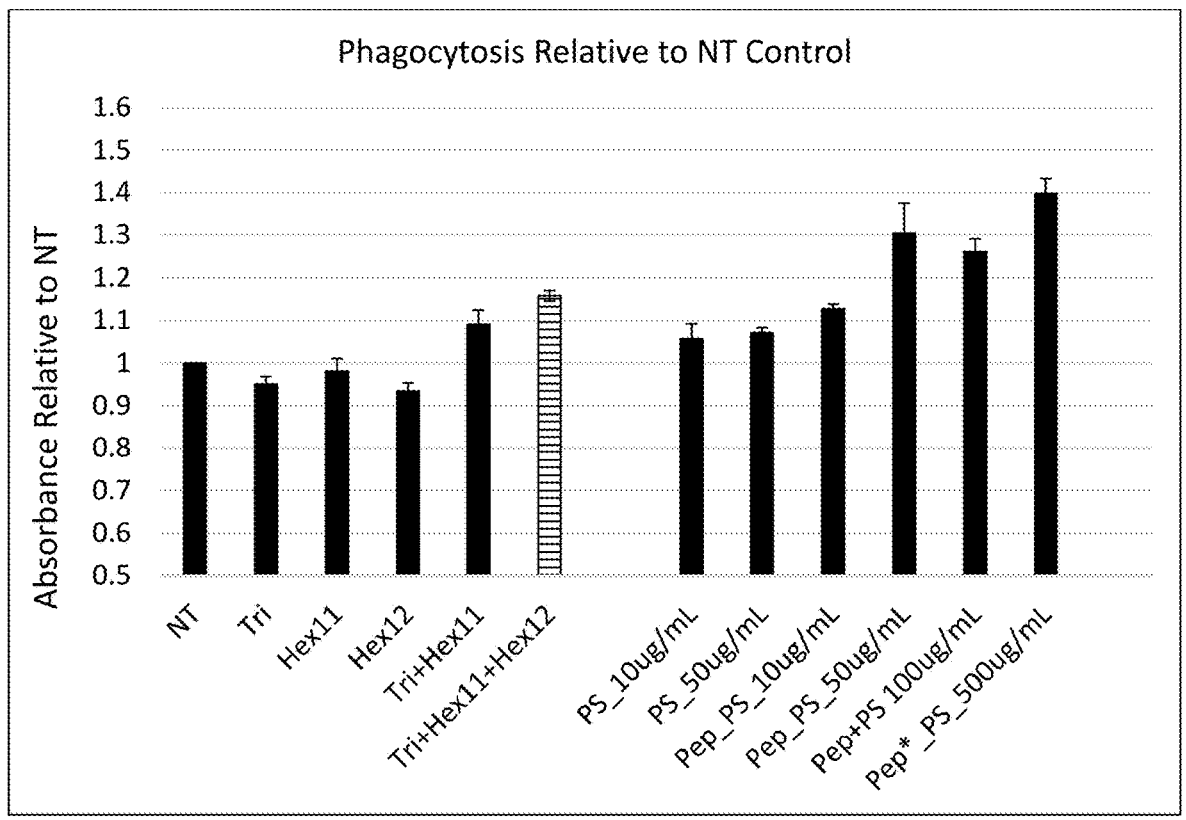
FIG. 7 illustrates a graph of phagocytosis following various treatments including: No treatment (NT), tripeptide-1 (Tri), hexapeptide-11 (Hex11), hexapeptide-12 (Hex12), tripeptide-1 and hexapeptide-11 (Tri+Hex11), tripeptide-1, hexapeptide-11, and hexapeptide-12 (Tri+Hex11+Hex12), phosphatidylserine at 10 ug/mL (PS_10 ug/mL), phosphatidylserine at 50 ug/mL (PS_50 ug/mL), tripeptide-1, hexapeptide-11, hexapeptide-12, and phosphatidylserine at 10 ug/mL (Pep_PS_10 ug/mL), tripeptide-1, hexapeptide-11, hexapeptide-12, and phosphatidylserine at 50 ug/mL (Pep_PS_50 ug/mL), tripeptide-1, hexapeptide-11, hexapeptide-12, and phosphatidylserine at 100 ug/mL (Pep_PS_100 ug/mL), and tripeptide-1, hexapeptide-11, hexapeptide-12, and phosphatidylserine at 500 ug/mL (Pep_PS_500 ug/mL).

The effect of phosphatidylserine was also determined. FIG. 7 shows effects of No treatment (NT), tripeptide-1 (Tri), hexapeptide-11 (Hex11), hexapeptide-12 (Hex12), tripeptide-1 and hexapeptide-11 (Tri+Hex11), tripeptide-1, hexapeptide-11, and hexapeptide-12 (Tri+Hex11+Hex12), phosphatidylserine at 10 ug/mL (PS_10 ug/mL), phosphatidylserine at 50 ug/mL (PS_50 ug/mL), tripeptide-1, hexapeptide-11, hexapeptide-12, and phosphatidylserine at 10 ug/mL (Pep_PS_10 ug/mL), tripeptide-1, hexapeptide-11, hexapeptide-12, and phosphatidylserine at 50 ug/mL (Pep_PS_50 ug/mL), tripeptide-1, hexapeptide-11, hexapeptide-12, and phosphatidylserine at 100 ug/mL (Pep_PS_100 ug/mL), and tripeptide-1, hexapeptide-11, hexapeptide-12, and phosphatidylserine at 500 ug/mL (Pep_PS_500 ug/mL). As seen in FIG. 7, tripeptide-1, hexapeptide-11, hexapeptide-12, and phosphatidylserine at 50 ug/mL treatment and tripeptide-1, hexapeptide-11, hexapeptide-12, and phosphatidylserine at 500 ug/mL treatment showed a significant increase over peptide treatment alone. The increase of tripeptide-1, hexapeptide-11, and hexapeptide-12 treatment was 1.15. The increase of tripeptide-1, hexapeptide-11, hexapeptide-12, and phosphatidylserine at 50 ug/mL treatment was 1.30. The increase of tripeptide-1, hexapeptide-11, hexapeptide-12, and phosphatidylserine at 500 ug/mL treatment was 1.40. Tripeptide-1, hexapeptide-12, and phosphatidylserine at 50 ug/mL treatment as well as tripeptide-1, hexapeptide-11, hexapeptide-12, and phosphatidylserine at 500 ug/mL treatment resulted in a 2×-3× efficacy over peptide treatment alone and a 4× efficacy over NT control.

Figure 8:
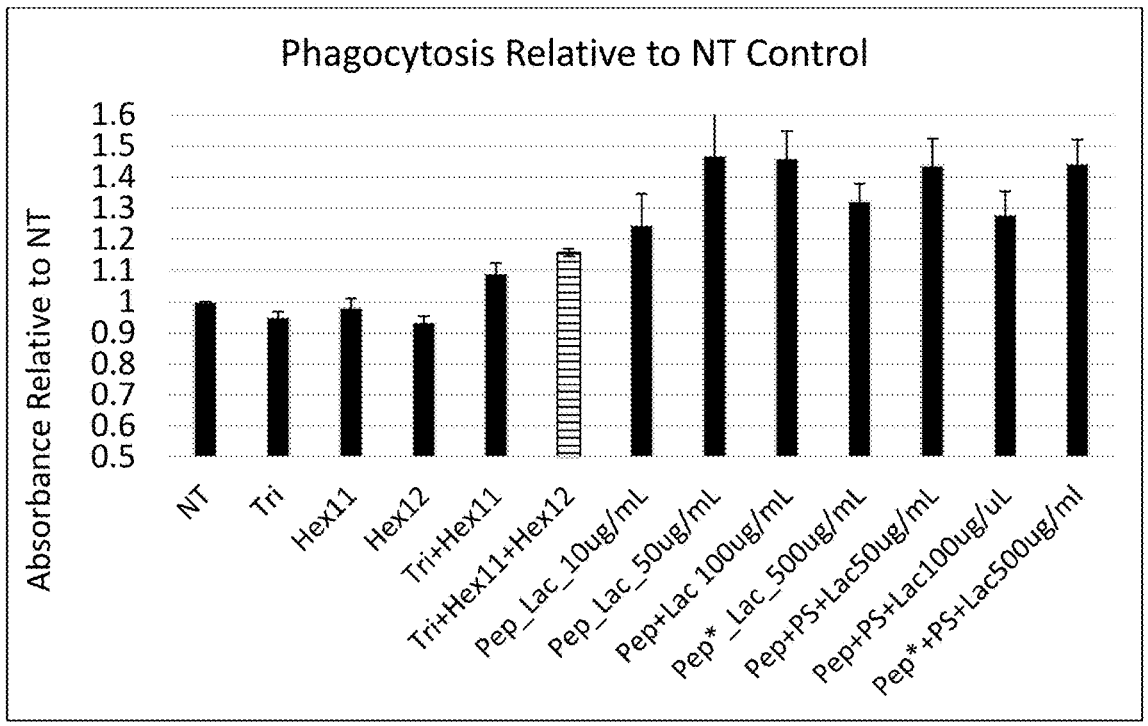
FIG. 8 illustrates a graph of phagocytosis following various treatments including: No treatment (NT), tripeptide-1 (Tri), hexapeptide-11 (Hex11), hexapeptide-12 (Hex12), tripeptide-1 and hexapeptide-11 (Tri+Hex11), tripeptide-1, hexapeptide-11, and hexapeptide-12 (Tri+Hex11+Hex12), tripeptide-1, hexapeptide-11, hexapeptide-12, and lactoferrin at 10 ug/mL (Pep_Lac_l0 ug/mL), tripeptide-1, hexapeptide-11, hexapeptide-12, and lactoferrin at 50 ug/mL (Pep_Lac_50 ug/mL), tripeptide-1, hexapeptide-11, hexapeptide-12, and lactoferrin at 100 ug/mL (Pep+Lac100 ug/mL), tripeptide-1, hexapeptide-11, hexapeptide-12, and lactoferrin at 500 ug/mL (Pep_Lac_500 ug/mL), tripeptide-1, hexapeptide-11, hexapeptide-12, phosphatidylserine and lactoferrin at 50 ug/mL (Pep+PS+Lac50 ug/mL), tripeptide-1, hexapeptide-11, hexapeptide-12, phosphatidylserine and lactoferrin at 100 ug/mL (Pep+PS+Lac100 ug/mL), and tripeptide-1, hexapeptide-11, hexapeptide-12, phosphatidylserine and lactoferrin at 500 ug/mL (Pep+PS+Lac500 ug/mL).

The effects of lactoferrin were determined. FIG. 8 shows effects of No treatment (NT), tripeptide-1 (Tri), hexapeptide-11 (Hex11), hexapeptide-12 (Hex12), tripeptide-1 and hexapeptide-11 (Tri+Hex11), tripeptide-1, hexapeptide-11, and hexapeptide-12 (Tri+Hex11+Hex12), tripeptide-1, hexapeptide-11, hexapeptide-12, and lactoferrin at 10 ug/mL (Pep_Lac_l0 ug/mL), tripeptide-1, hexapeptide-11, hexapeptide-12, and lactoferrin at 50 ug/mL (Pep_Lac_50 ug/mL), tripeptide-1, hexapeptide-11, hexapeptide-12, and lactoferrin at 100 ug/mL (Pep+Lac100 ug/mL), tripeptide-1, hexapeptide-11, hexapeptide-12, and lactoferrin at 500 ug/mL (Pep_Lac_500 ug/mL), tripeptide-1, hexapeptide-11, hexapeptide-12, phosphatidylserine at 500 ug/mL and lactoferrin at 50 ug/mL (Pep+PS+Lac50 ug/mL), tripeptide-1, hexapeptide-11, hexapeptide-12, phosphatidylserine at 500 ug/mL and lactoferrin at 100 ug/mL (Pep+PS+Lac100 ug/mL), and tripeptide-1, hexapeptide-11, hexapeptide-12, phosphatidylserine at 500 ug/mL and lactoferrin at 500 ug/mL (Pep+PS+Lac500 ug/mL). As seen in FIG. 8, tripeptide-1, hexapeptide-11, hexapeptide-12, and lactoferrin at 50 ug/mL resulted in about 30% increase in phagocytosis relative to tripeptide-1, hexapeptide-11, and hexapeptide-12 treatment and 45-50% (4.5-5× efficacy) increase over NT control. Treatment with tripeptide-1, hexapeptide-11, hexapeptide-12, and lactoferrin at 500 ug/mL resulted in about 20% increase in efficacy as compared to NT control. Treatment with tripeptide-1, hexapeptide-11, hexapeptide-12, phosphatidylserine at 500 ug/mL, and lactoferrin at 500 ug/mL also resulted in about 45% increase in efficacy as compared to NT control.

Figure 9:
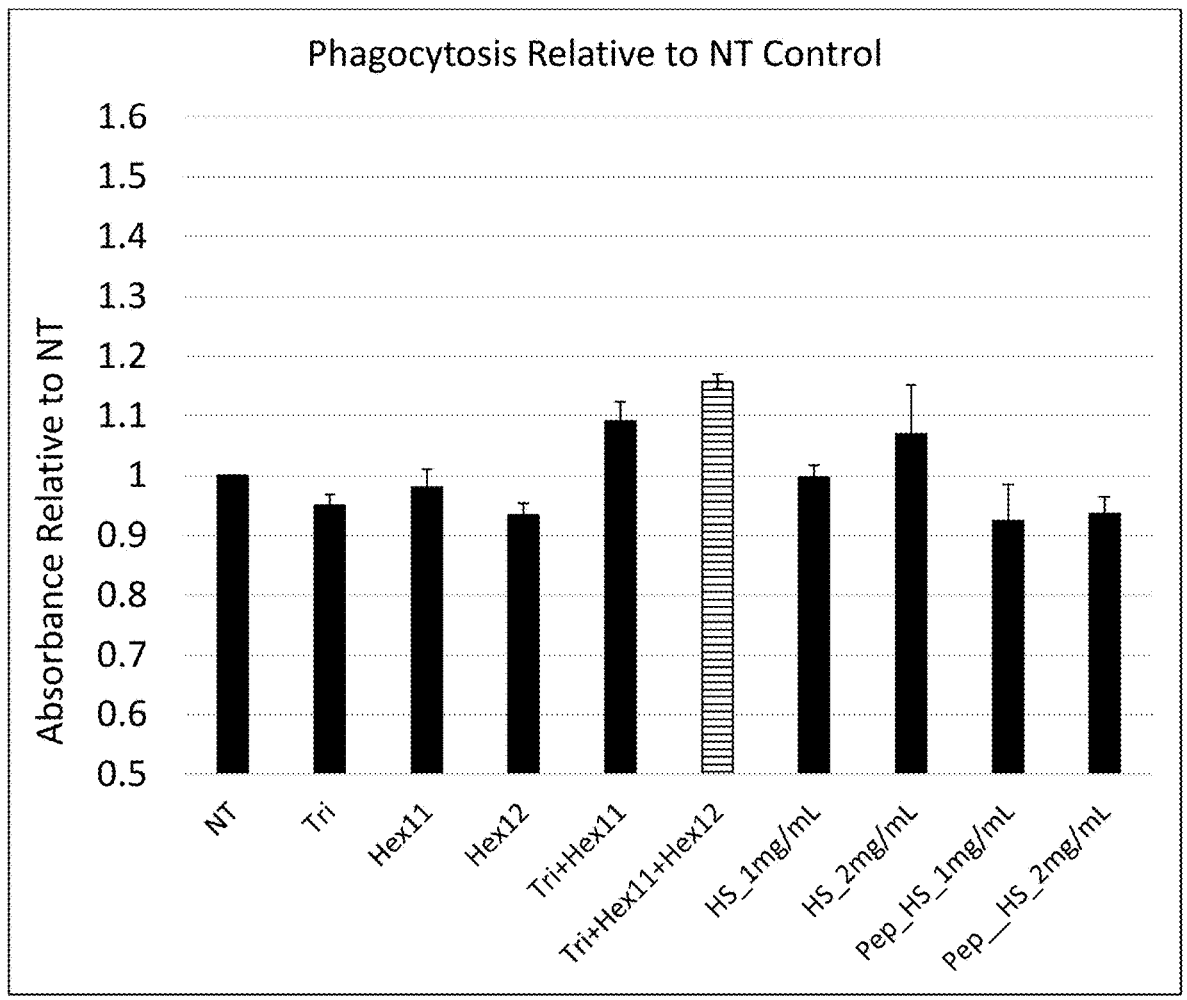
FIG. 9 illustrates a graph of phagocytosis following various treatments including: No treatment (NT), tripeptide-1 (Tri), hexapeptide-11 (Hex11), hexapeptide-12 (Hex12), tripeptide-1 and hexapeptide-11 (Tri+Hex11), tripeptide-1, hexapeptide-11, and hexapeptide-12 (Tri+Hex11+Hex12), hydroxysuccinimide at 1 mg/mL (HS_1 mg/mL), hydroxysuccinimide at 2 mg/mL (HS_2 mg/mL), tripeptide-1, hexapeptide-11, hexapeptide-12, and hydroxysuccinimide at 1 mg/mL (Pep_HS_1 mg/mL), and tripeptide-1, hexapeptide-11, hexapeptide-12, and hydroxysuccinimide at 2 mg/mL (Pep_HS_2 mg/mL).

The effects of hydroxysuccinimide were determined. FIG. 9 shows the effects of No treatment (NT), tripeptide-1 (Tri), hexapeptide-11 (Hex11), hexapeptide-12 (Hex12), tripeptide-1 and hexapeptide-11 (Tri+Hex11), tripeptide-1, hexapeptide-11, and hexapeptide-12 (Tri+Hex11+Hex12), hydroxysuccinimide at 1 mg/mL (HS_1 mg/mL), hydroxysuccinimide at 2 mg/mL (HS_2 mg/mL), tripeptide-1, hexapeptide-11, hexapeptide-12, and hydroxysuccinimide at 1 mg/mL (Pep_HS_1 mg/mL), and tripeptide-1, hexapeptide-11, hexapeptide-12, and hydroxysuccinimide at 2 mg/mL (Pep_HS_2 mg/mL). As seen in FIG. 9, hydroxysuccinimide treatments show little to no change in phagocytosis.

Figure 10:
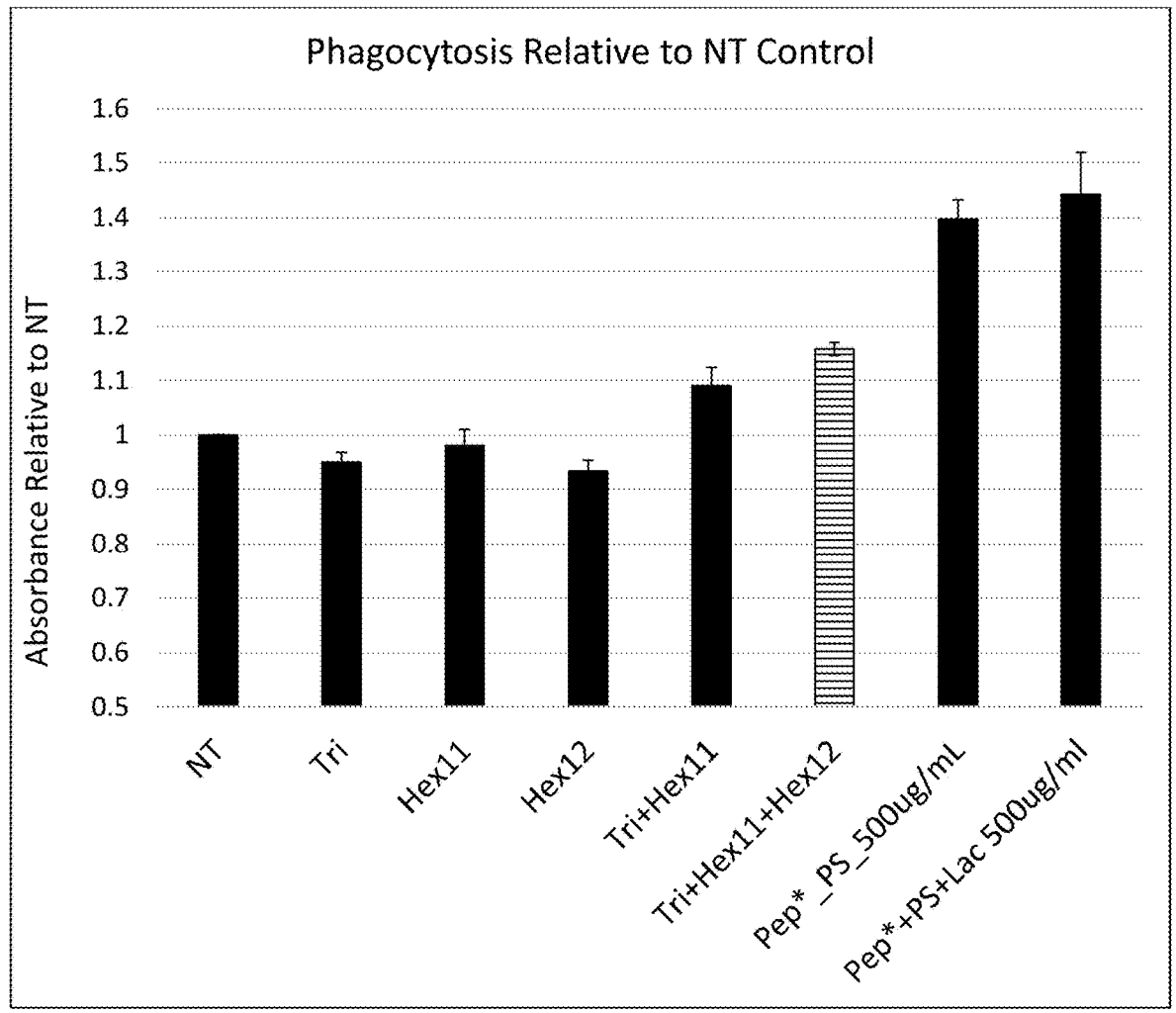
FIG. 10 illustrates a graph of phagocytosis following various treatments including: No treatment (NT), tripeptide-1 (Tri), hexapeptide-11 (Hex11), hexapeptide-12 (Hex12), tripeptide-1 and hexapeptide-11 (Tri+Hex11), tripeptide-1, hexapeptide-11, and hexapeptide-12 (Tri+Hex11+Hex12), tripeptide-1, hexapeptide-11, hexapeptide-12 and phosphatidylserine at 500 ug/mL (Pep_PS_500 ug/mL), and tripeptide-1, hexapeptide-11, hexapeptide-12, phosphatidylserine at 500 ug/mL, and lactoferrin at 500 ug/mL (Pep+PS+Lac500 ug/mL).

The effects of tripeptide-1, hexapeptide-11, hexapeptide-12, phosphatidylserine, and lactoferrin on phagocytosis were determined. FIG. 10 shows the effects of No treatment (NT), tripeptide-1 (Tri), hexapeptide-11 (Hex11), hexapeptide-12 (Hex12), tripeptide-1 and hexapeptide-11 (Tri+Hex11), tripeptide-1, hexapeptide-11, and hexapeptide-12 (Tri+Hex11+Hex12), tripeptide-1, hexapeptide-11, hexapeptide-12 and phosphatidylserine at 500 ug/mL (Pep_PS_500 ug/mL), and tripeptide-1, hexapeptide-11, hexapeptide-12, phosphatidylserine at 500 ug/mL, and lactoferrin at 500 ug/mL (Pep+PS+Lac500 ug/mL). As seen in FIG. 10, the peptide combination (Tri+Hex11+Hex12) resulted in an increase in efficacy (15% increase over control). The phosphatidylserine addition (Pep_PS_500 ug/mL) demonstrated a 30% increase over control. The tripeptide-1, hexapeptide-11, hexapeptide-12, phosphatidylserine at 500 ug/mL, and lactoferrin at 500 ug/mL treatment resulted in about 47% increase in efficacy in macrophage phagocytosis and approximately 300% increased efficiency over peptide combination alone.

Example 3: Clinical Trial Evaluating Improvements in Bruising

The effects of the composition of Table 1 are evaluated in subjects following injection of a dermal filler. Twenty subjects are chosen to participate in the trial. Exclusion and inclusion criteria are listed in Table 2.

TABLE 2

| | |
|---|---|
| Inclusion Criteria | Adult females or males, age 25 to 65 years
Subjects are seeking treatment with BOTOX ® injection
Subjects have one or more moderate to severe hyperfunctional facial lines of the upper face (i.e., glabellar lines, lateral canthal lines (crow's feet) or horizontal forehead lines) or moderate to severe nasolabial folds based on the physician observer assessment (0-3 scale)
Women are either of non-childbearing potential (i.e., surgically sterilized or post-menopausal) or if of childbearing potential, are not pregnant (as documentedby a negative urine pregnancy test at the baseline examination) or lactating and are practicing a medically acceptable method of birth control
Subjects are willing and able to provide written informed consent
Subjects are willing and able to follow the procedures outlined in this protocol |
| Exclusion Criteria | Female subjects who are pregnant (positive urine pregnancy test) or who have an infant they are breast-feeding or who are of childbearing potential and not practicing a reliable method of birth control
Previous botulinum toxin or semipermanent injectable filler therapy within the past year or any prior history of permanent filler therapy injection
Prior cosmetic procedures (i.e., liposuction, etc.) or visible scars that may affect evaluation of response and/or quality of photography
Known allergy or sensitivity to any of the study medication or their components
Known severe allergies manifested by a history of anaphylaxis or history or presence of multiple severe allergies
Diagnosis of myasthenia gravis, Eaton-Lambert syndrome, amyotrophic lateral sclerosis or any other disease that might interfere with neuromuscular function
Concurrent use of aminoglycoside antibiotics that interfere with neuromuscular function
Subjects with profound atrophy or excessive weakness of the muscles in the target area(s) of BOTOX ® injection
Subjects with an infection at an injection site or systemic infection (in this case, postpone study entry until one week following recovery)
Concurrent participation in an investigational drug or device study or participation within 30 days of study start
Subjects are not to undergo any additional cosmetic procedures during the study period
Subjects are not to change use of any facial products up to 6 months prior to enrollment and during study period
Subjects with a history of poor cooperation, non-compliance with medical treatment, or unreliability |

Each subject will receive two BOTOX® Cosmetic injections: one on a first side of an affected facial region and a second on a second side of the affected facial region. After two weeks, the subjects will apply the composition of Table 1 twice daily. Assessments are taken at 3, 4, 6, 8, and 12 weeks. Improvements in the subjects are determined using Physician Global Aesthetic Improvement Scale (PGAIS).

Example 4. A Multi-Center, Double-Blinded Study to Evaluate the Efficacy and Safety of a Topical Product for the Treatment of Bruises The objective of this study is to evaluate the efficacy and safety of a topical product comprising a formula as described Table 1 in dissipating a bruise compared to a bland moisturizer.

The duration of the study is 3 months. Approximately 10 subjects will be enrolled per site with up to 3 sites that are participating. Subjects include healthy male and female subjects 18 years of age or older. The inclusion criteria and exclusion criteria are listed in Table 3.

TABLE 3

| | |
|---|---|
| \multicolumn{2}{c}{Inclusion and Exclusion Criteria} | |
| Inclusion Criteria | Age 18-60 years old male and female subjects willing to receive a laser induced bruise on both sides of the inner arm
Subjects are in good health
Subjects are willing, have the ability to understand and provide informed consent, and are able to communicate with the investigator |
| Exclusion Criteria | Pregnant or lactating
Subjects who are unable to understand the protocol or give informed consent
Subjects currently under treatment with blood thinners or any medical treatments that in the opinion of the Investigator would deem them not suitable for this study
Subjects who have active skin disease or skin infection in the treatment area
Subjects who have a history of abnormal bleeding or bleeding and bruising disorders |

The study will consist of a screening visit, one laser induced procedure visit and follow-up visits on post bruise Days 2, 4, 6, 8, 10 and 14. Subjects that have opted for the biopsies will return at a designated time-point after the initial biopsies for a second set of biopsies. Subjects may consent for the study up to 30 days before Visit 1.

Visit 1 procedures will consist of the following: Completion of ICF, demographics, medical/dermatological history and study criteria confirmation. If the subject is eligible for the study, the subject will undergo a laser procedure on the right and left inner arm in order to induce a bruise. Standard photography will be taken pre and post bruise formation on each arm. Subjects will be randomized to receive either topical bruise product or bland moisturizer on the right or left arm. Subjects will use the topical product twice daily on the designated arm. Subjects receiving a forearm biopsy will put the randomized designated product on the forearm twice daily.

On follow-up Days 2, 4, 6, 8, 10 and 14, the subject will return to the clinic and be queried for any changes in health status since the previous visit. Subject and Investigator assessments will be completed. Standardized photography will be completed.

At week 2, two subjects that have opted for forearm biopsies will return to the office for the second biopsies and then return for stitch removal as per first biopsy.

Study measurements for efficacy include standardized photography, biopsies, and subject satisfaction questionnaire. Standardized photos will be taken at every visit and pre-post procedure. These photos will be used for comparable assessment of the bruises. Biopsies will be taken of two arbitrarily patients that consent to a biopsy of the forearms at Visit 1 and at two weeks post use of the topical products. The specimens will be reviewed by a blinded dermatopathologist. Subject will rate satisfaction with the product and delivery using the subject satisfaction questionnaire. Further safety will be determined by recording the number of adverse events (AE) per schedule of events.

Measurements for efficacy include co-primary efficacy endpoints, which comprise Global Improvement in the bruises between arms. Secondary efficacy endpoints will also be measured. The secondary efficacy endpoints include changes from Baseline in dermatopathology, dermal changes from skin biopsy, and Subject Satisfaction Questionnaire at end of study. Safety endpoints will also be measured including incidence (severity and causality) of any local and systemic adverse events (AEs).

Example 5. Clinical Evaluation of the Efficacy of a Topical Product for the Treatment of Bruises Post Cosmetic Injections The objective of this study is to evaluate the efficacy of a topical product comprising a formula as described in Table 1 in dissipating a bruise post cosmetic injections.

The duration of the study is 3 months. Approximately 50 subjects will be enrolled. Subjects include healthy male and female subjects 18 years of age or older. The inclusion criteria and exclusion criteria are listed in Table 4

TABLE 4

Inclusion and Exclusion Criteria

| | |
|---|---|
| Inclusion Criteria | Age 18-60 years old male and female subjects electing to receive cosmetic injectables |
| | Subjects are in good health |
| | Subjects are willing to understand and provide informed consent |
| Exclusion Criteria | Pregnant or lactating |
| | Subjects who in the Investigators opinion are not suitable for cosmetic injectables |

The study will consist of a Day 1 treatment visit and follow-up visits on Days 2, 4, 6, 8, 10 and 14. Subjects may consent for the study up to 30 days before Day 1.

The Day 1 procedures will consist of the following: Completion of ICF, demographics, medical/dermatological history. The subject will undergo the elected cosmetic inject- ables as decided by the Investigator and subject. Standard photography will be taken post bruise formation. Subjects will be randomized to apply the topical bruise product on either the left or right side of the face. Subjects will use the topical product twice daily on the designated bruises.

Follow-up Days 2, 4, 6, 8, 10 and 14: The subject will return to the clinic and be queried for any changes in health status since the previous visit. Standardized photography will be completed of the bruises.

Study measurements include efficacy and safety measurements. Efficacy will be determined using standardized photography and the Subject Satisfaction Questionnaire. Standardized photos will be taken at every visit and post procedure. These photos will be used for comparable assessment of the bruises. Using the Subject Satisfaction Questionnaire, the subject will rate satisfaction with the product and delivery. Safety measurements include recording adverse events (AE) per the schedule of events.

Study efficacy is determined using primary efficacy endpoints and secondary efficacy endpoints. Primary efficacy endpoints include Global Improvement in the treated bruises compared to the non-treated. Secondary efficacy endpoints include Subject Satisfaction Questionnaire at end of study. Safety endpoints are also measured as incidence (severity and causality) of any local and systemic adverse events (AEs).

Example 6. Preparation of Liposomal Compositions

Figure 11A:
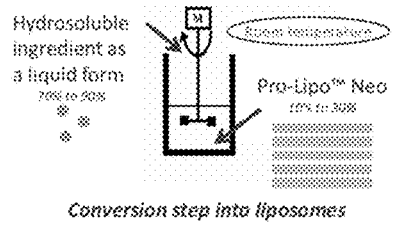
Figure 11A:
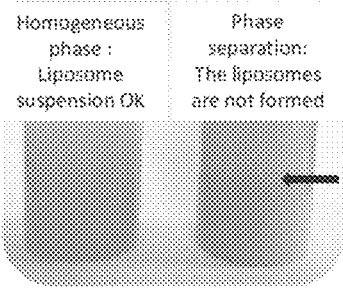
Figure 11A:
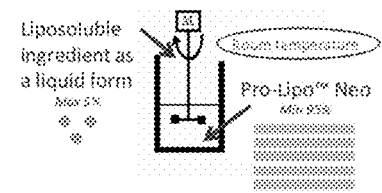
Figure 11A:
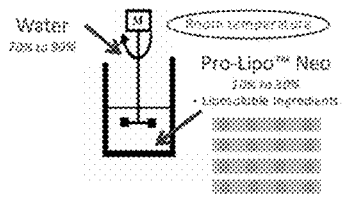
Figure 11A:
Figure 11A:
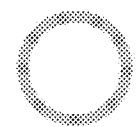
Figure 11A:
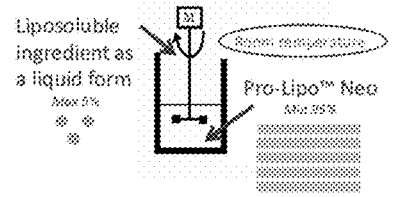
Figure 11A:
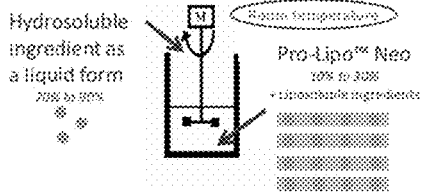
Figure 11A:
Figure 11A:
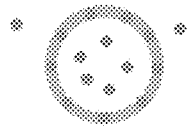
Figure 11B:
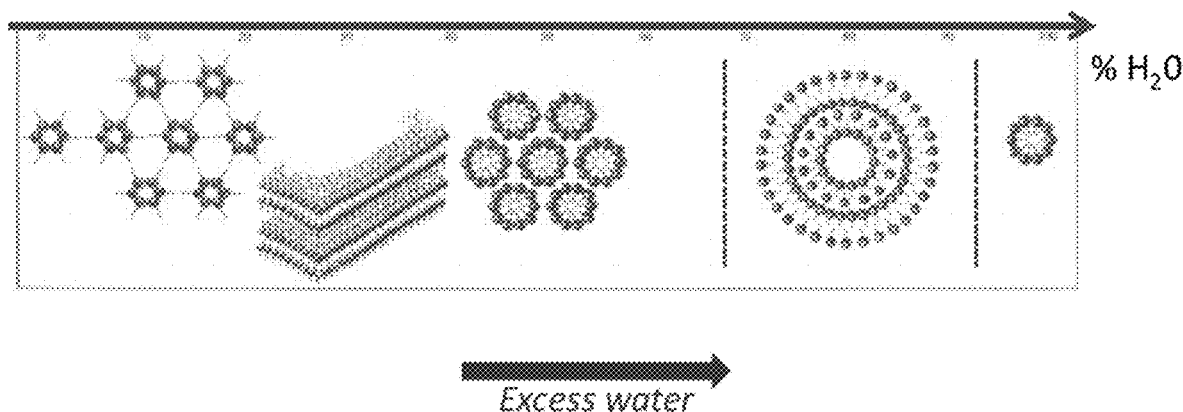
Figure 12:
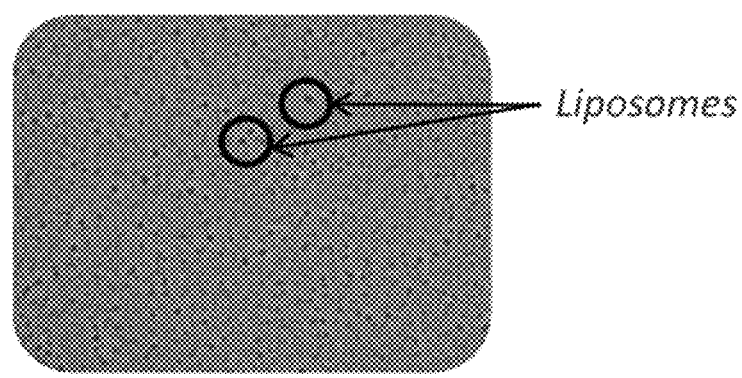
FIG. 12 shows an image of a liposome.

A liposomal preparation was prepared according to the schematic as seen in FIG. 11A. FIG. 11A shows the various methods for creating liposomes including hydrosoluble ingredient entrapment, liposoluble ingredient entrapment, and a liposoluble and hydrosoluble ingredient entrapment. FIG. 11B shows a schematic of liposomal formation. Liposomes were observed following the liposome suspension process manufacturing as seen in FIG. 12.

Example 7. Efficacy of Liposomal Compositions

Efficacy of liposomal compositions was tested for bioavailability and skin penetration.

A water suspension of liposomes was prepared with 1.5% of hydrophilic molecule A or 300 ppm (0.03%) hydrophilic molecule B, and 27% Pro-Lipo™ Neo. Molecule A was caffeine and had a molecular weight of 194.2 g/mol and a penetration ability of log Kow of −0.07. Molecule B was a hexapeptide (hexapeptide-38) with a molecular weight of (870 g/mol) and a penetration ability log Kow of −1.13. A water solution with 1.5% A or 300 ppm B was used as a control (non-entrapped molecule).

A dose of 10 mg/cm$^2$ was applied on skin explants using the Franz cell method. The kinetic of the molecules passed through skin explants was measured during 24 hours. After 24 hours, the molecule content was measured in each skin compartment including the stratum corneum, epidermis, dermis, and receptor fluid.

Figure 13A:
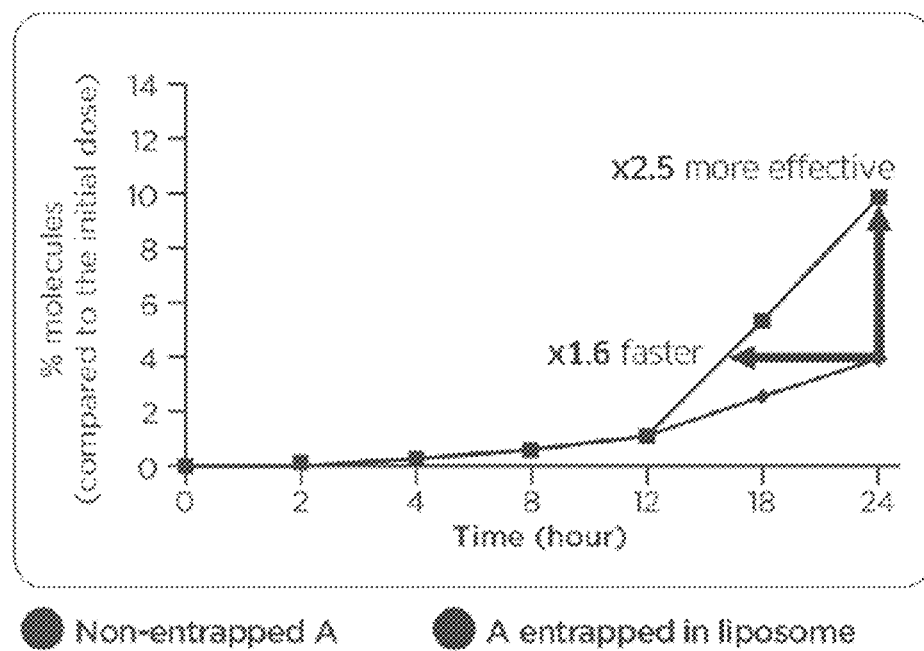
FIG. 13A shows a graph of diffusion of Molecule A through human skin.
Figure 13B:
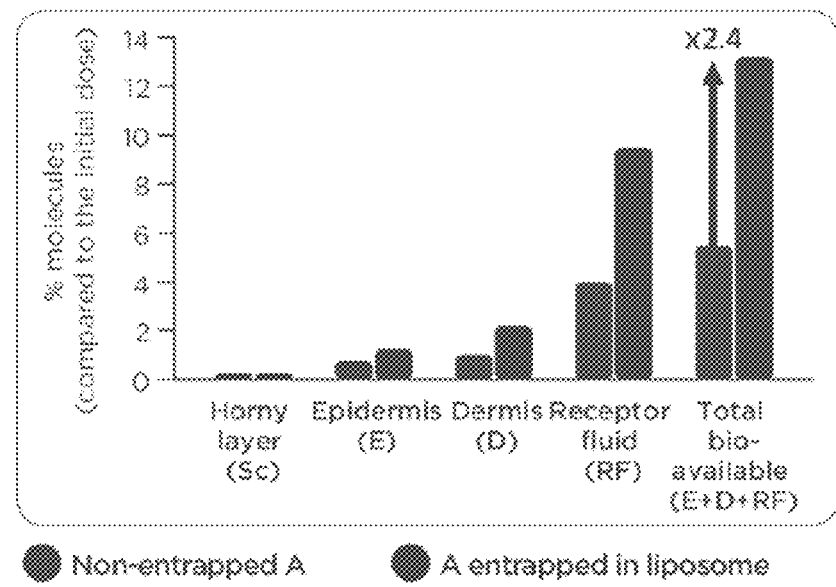
FIG. 13B shows a graph of skin distribution of Molecule A.
Figure 13C:
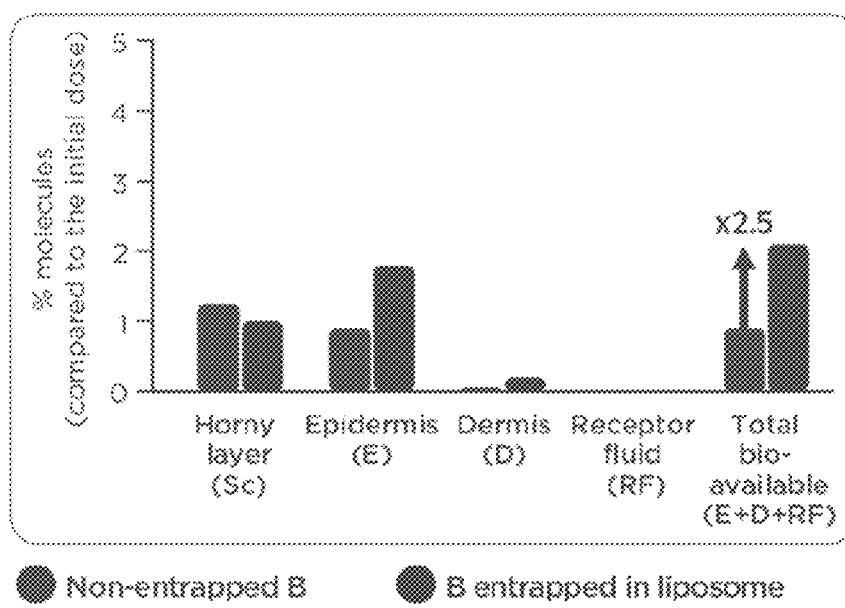
FIG. 13C shows a graph of skin distribution of Molecule B after 24 hours.
Figure 14A:
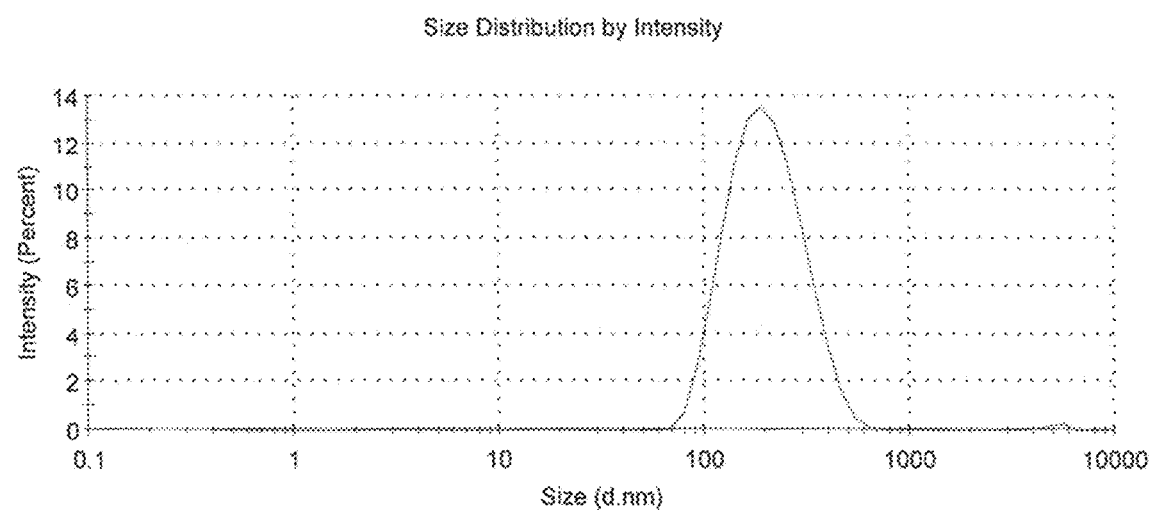
FIGS. 14A-14B show graphs of size distribution of acetyl hexapeptide-38 in a first experiment.
Figure 14B:
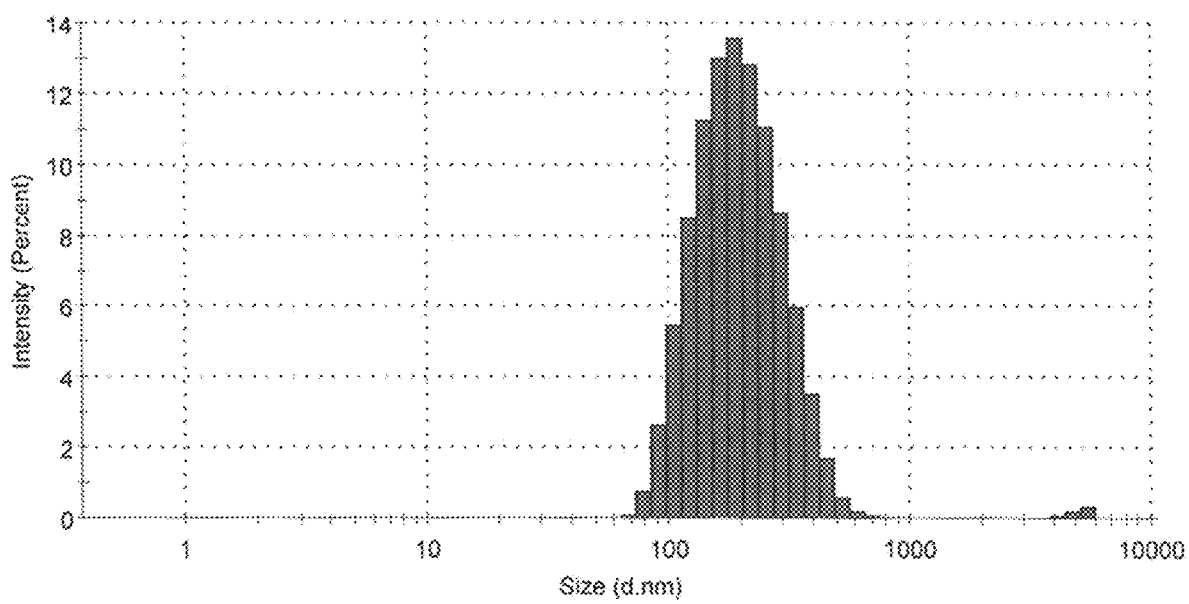
Figure 14C:
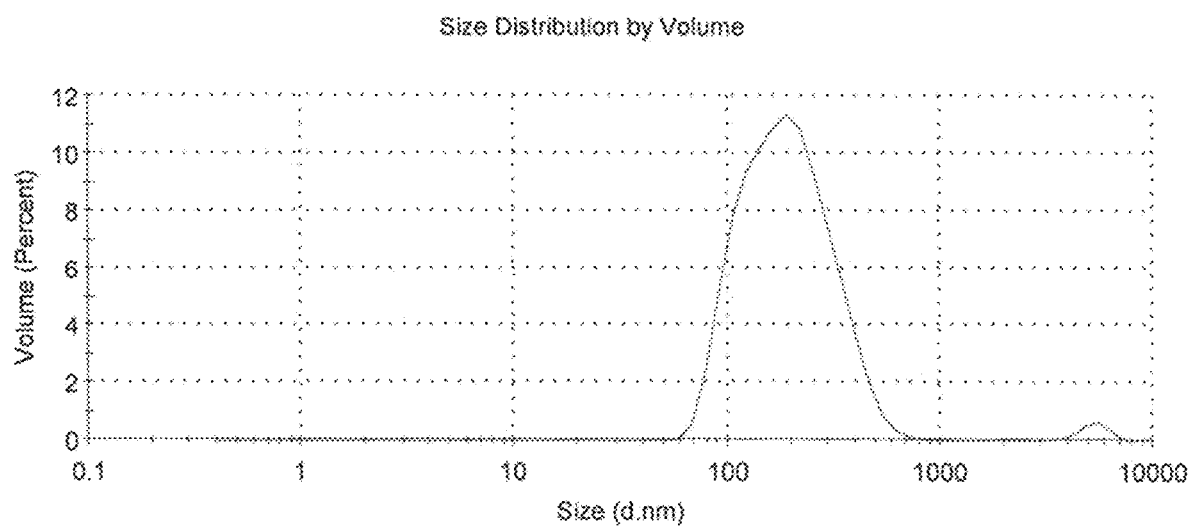
FIGS. 14C-14D show graphs of size distribution of acetyl hexapeptide-38 in a second experiment.
Figure 14D:
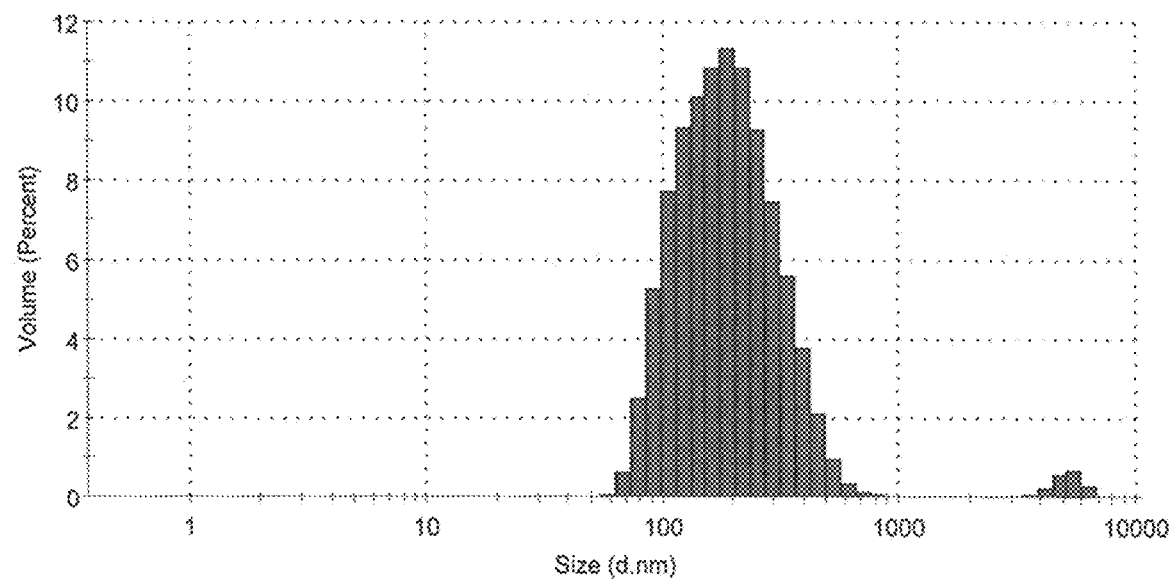

FIGS. 13A-13B show graphs of diffusion of Molecule A through the human skin (FIG. 13A) and skin distribution of Molecule A (FIG. 13B). As seen in FIG. 13A, Molecule A formulated in liposomes was 2.5× more effective and 1.6× faster than non-entrapped molecule. As seen in FIG. 13B, Molecule A formulated in liposomes was 2.4× more efficacious at total bioavailability after 24 hours. Molecule B formulated in liposomes also exhibited increased bioavailability as seen as a 2.5× increase in skin distribution of Molecule B after 24 hours (FIG. 13C).

Example 8. Particle Size of Liposomal Acetyl Hexapeptide 38

The particle size of liposomal acetyl hexapeptide 38 was determined.

100 uL of liposomal acetyl hexapeptide 38 was dissolved in 15 mL of water. Assay information can be seen in Table 5 for two experiments.

TABLE 5

|  | Experiment 1 | Experiment 2 |
|---|---|---|
| Material RI | 1.59 | 1.59 |
| Material Absorption | 0.010 | 0.010 |
| Dispersant Name | Water | Water |
| Dispersant RI | 1.330 | 1.330 |
| Viscosity (cP) | 0.8872 | 0.8872 |
| Temperature (° C.) | 25 | 25 |
| Count Rate (kcps) | 149.1 | 149.1 |
| Cell Description | Disposable sizing cuvette | Disposable sizing cuvette |
| Duration Used (s) | 80 | 80 |
| Measurement position (mm) | 4.65 | 4.65 |
| Attenuator | 7 | 7 |

Results from the experiments can be seen in Tables 6-8 and FIGS. 14A-14D.

TABLE 6

| PdI refers to polydispersity index and the intercept refers to amplitude. | | |
|---|---|---|
|  | Experiment 1 | Experiment 2 |
| Z-Average (d. · nm) | 184.7 | 184.7 |
| PdI | 0.168 | 0.168 |
| Intercept | 0.961 | 0.961 |

TABLE 7

| | Experiment 1 | | | Experiment 2 | | |
|---|---|---|---|---|---|---|
| | Diam. (nm) | % Intensity | Width (nm) | Diam. (nm) | % Intensity | Width (nm) |
| Peak 1 | 211.4 | 99.4 | 88.24 | 205.5 | 98.3 | 100.4 |
| Peak 2 | 5026 | 0.6 | 594.1 | 5228 | 1.7 | 752.1 |
| Peak 3 | 0.000 | 0.0 | 0.000 | 0.000 | 0.0 | 0.000 |

TABLE 8

| | | INTENSITY-WEIGHTED | |
|---|---|---|---|
| | | NNLS RESULTS | |
| | CUMULANT RESULTS | PEAK OF | PEAK |
| | Z-AVERAGE (nm) | PDI | INTEREST (nm) | WIDTH (nm) |
| Liposomal Acetyl Hexapeptide 38 | 184.7 | 0.17 | 211.4 | 88.24 |

As seen in Tables 6-8 and FIGS. 14A-14D, a liposomal acetyl hexapeptide-38 composition was generated with a particle size of 184.7 nanometers (nm).

Example 9. Exemplary Formulations

Exemplary liposomal formulation is seen in Table 9.

TABLE 9

| Ingredient | % by wt. |
|---|---|
| Water/Aqua/Eau, | 50-95 |
| Glycerin | 0.5-9 |
| Caprylic/Capric Triglyceride | 1-9 |
| Propanediol | 0.01-5 |
| Polyacrylate-13 | 0.5-6 |
| Lactoferrin | 0.01-1 |
| Phosphatidylserine | 0.01-1 |
| Ledum Palustre (Labrador Tea) Extract | 0.1-2.5 |
| Arnica Montana Flower Extract | 0.0001-1 |
| Palmitoyl Hexapeptide-12 | 0.0001-1 |
| Palmitoyl Tripeptide-1 | 0.0001-1 |
| Hexapeptide-11 | 0.00500 |
| Acetyl Hexapeptide-38 | 0.0001-1 |
| Acetyl Tetrapeptide-2 | 0.0001-1 |
| Sodium Hyaluronate Crosspolymer | 0.0001-2.5 |
| Tremella Fuciformis Sporocarp (Silver Ear Mushroom) Extract | 0.001-2.5 |
| Peucedanum Graveolens (Dill) Extract | 0.01-2.5 |
| Hydroxymethoxyphenyl Decanone | 0.001-0.1 |
| Dunaliella Salina Extract | 0.001-0.5 |
| Betaine | 0.01-0.5 |
| Phospholipids | 0.01-1 |
| Xylitylglucoside | 0.1-2 |
| Squalane | 0.1-0.8 |
| Caprylyl Glycol | 0.1-0.5 |
| Anhydroxylitol | 0.1-1.5 |
| Polysorbate 20 | 0.01-0.5 |
| Xylitol | 0.1-0.5 |
| Butylene Glycol | 0.1-2 |
| Sorbitan Isostearate | 0.1-1 |
| Ethylhexylglycerin | 0.01-1 |
| Caprylhydroxamic Acid | 0.05-0.5 |
| Ascorbyl Palmitate | 0.001-0.1 |
| Xanthan Gum | 0.01-0.8 |
| Pentylene Glycol | 0.01-0.8 |
| Glucose | 0.01-0.8 |
| Helianthus Annuus (Sunflower) Seed Oil | 0.001-0.5 |
| Tocopherol | 0.001-0.8 |
| Leuconostoc/Radish Root Ferment Filtrate | 0.01-0.8 |

TABLE 9-continued

| Ingredient | % by wt. |
|---|---|
| Potassium Sorbate | 0.001-0.5 |
| Caprylyl Methicone | 0.1-0.8 |
| Polyisobutene | 0.1-.8 |
| Lecithin | 0.1-1 |
| Disodium EDTA | 0.1-1 |
| Phenoxyethanol | 0.1-2 |

Example 10. In Vivo Testing of Bruising Resolution

Study Design

A 2-center, randomized, double-blind study was undertaken to assess the efficacy and safety of a topical product formulated to increase the elimination of blood products that manifest as a bruise. This study investigated the ability of the topical product comprising a formula as described in Table 9 to improve the appearance of a bruise compared to a bland moisturizer. 18 subjects were recruited the study and 16 subjects (32 bruises) completed the study.

Eligible subjects received an induced bruise on both arms via mechanical disruption, venipuncture, of a vessel as in a blood draw (1 group) or via removal of blood and re-injection of 0.1 mL subdermally in the proximal inner forearm just distal to the antecubital fossa.

Subjects were randomized to receive the topical product and bland moisturizer to use on the designated arm at a minimum of four times daily. One arm received the topical product on the bruise four times a day, and the other arm received the bland moisturizer (Cetaphil lotion) four times a day. Subjects were screened and underwent procedural (Day 0) visit and follow-up visits at days 1, 2, 3, 6, and 7. Two subjects consented to have a biopsy on the forearm at Day 0, pre-treatment, and at day 12/20 post procedure. Skin colorimetry (Skin ColorCatch) was performed in triplicate at each visit and clinical change of bruises documented through photography.

Assessed endpoints included global Improvement in the appearance of bruises between arms with comparison in Skin Color Catch measurements.

Figure 15A:
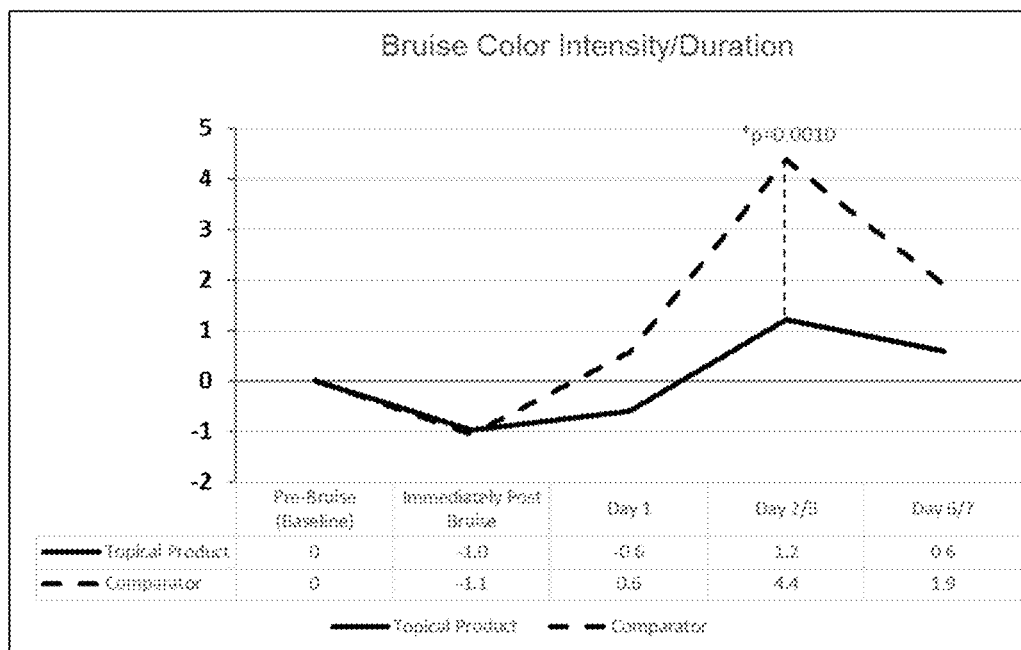
FIG. 15A shows a graph of bruise color intensity over time following administration of the topical product and the bland moisturizer.
Figure 15B:
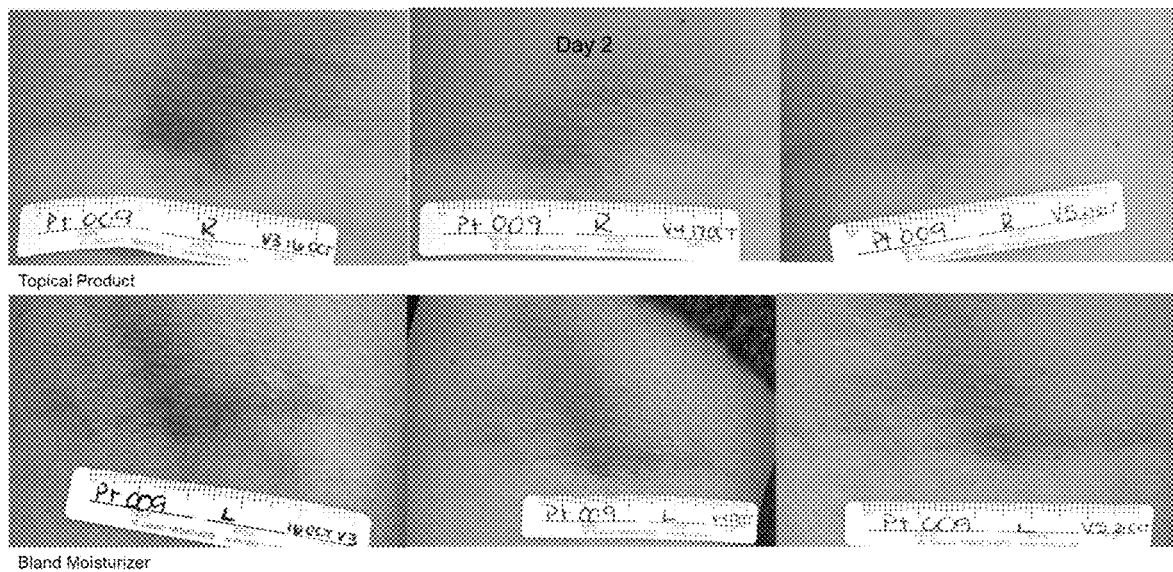
FIG. 15B shows images of bruising resolution of a first subject administered the topical product on the right arm and the bland moisturizer on the left arm.
Figure 15C:
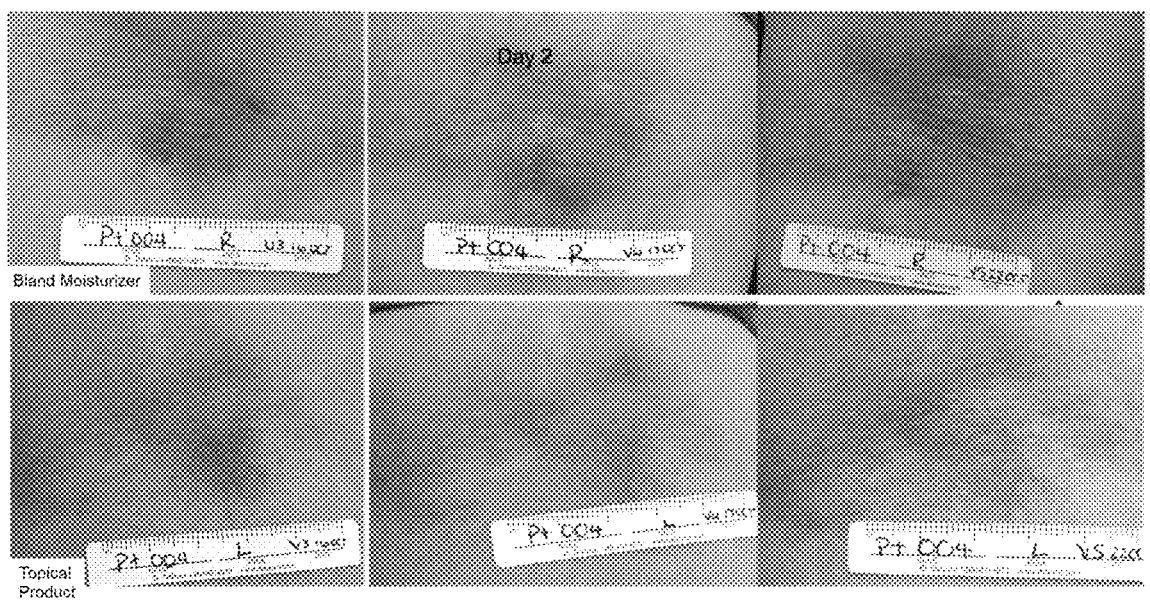
FIG. 15C shows images of bruising resolution of a second subject administered the topical product on the left arm and the bland moisturizer on the right arm.
Figure 15D:
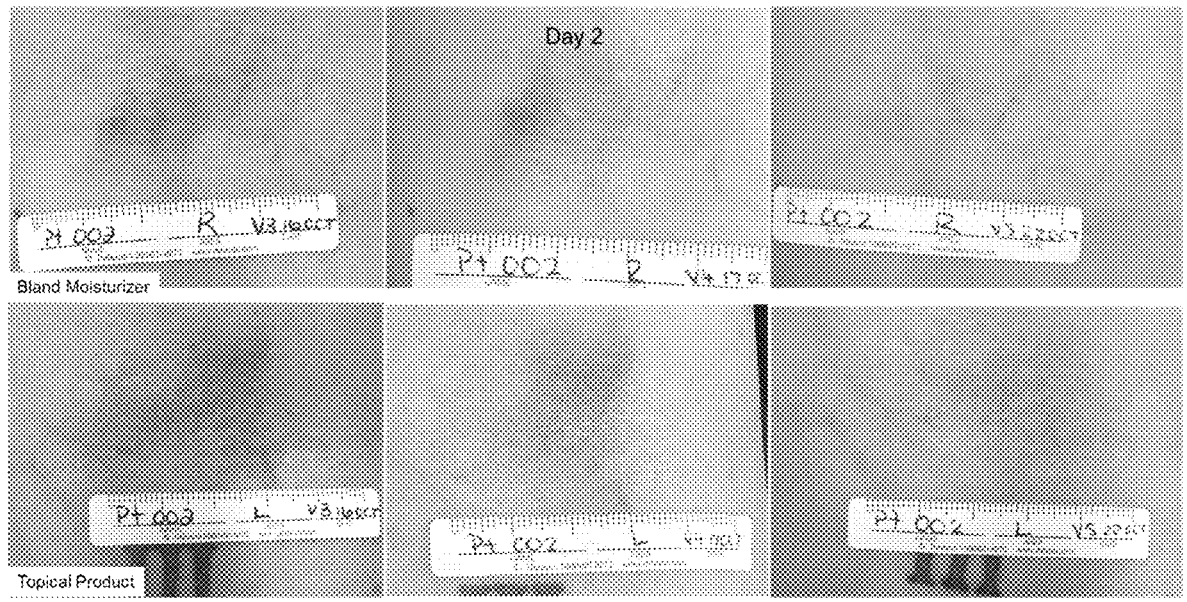
FIG. 15D shows images of bruising resolution of a third subject administered the topical product on the left arm and the bland moisturizer on the right arm.
Figure 15E:
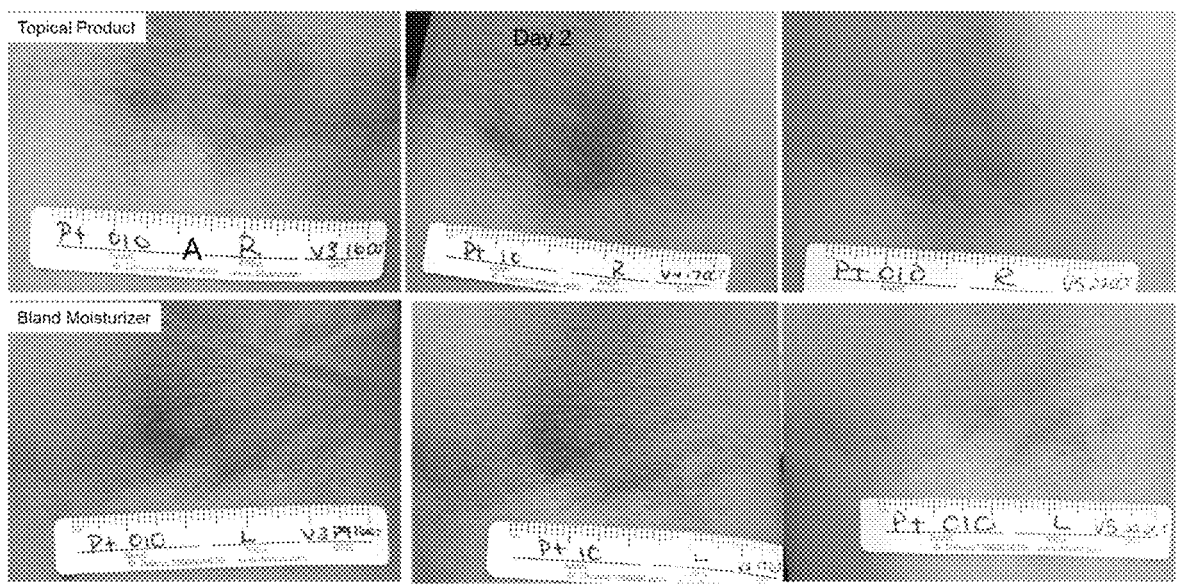
FIG. 15E shows images of bruising resolution of a fourth subject administered the topical product on the right arm and the bland moisturizer on the left arm.
Figure 15F:
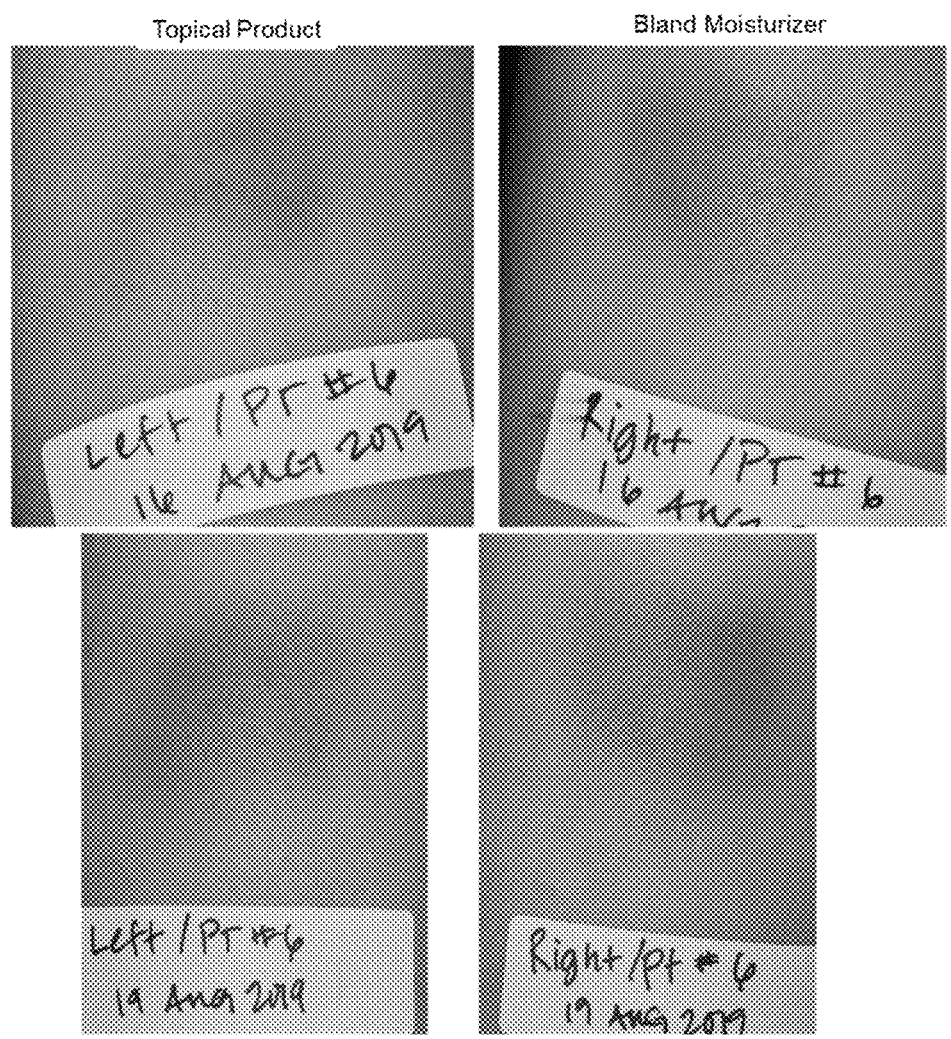
FIG. 15F shows images of bruising resolution of a fifth subject administered the topical product on the left arm and the bland moisturizer on the right arm.

Results 18 subjects were recruited the study, and 16 subjects (32 bruises) completed the study as two subjects were withdrawn from analysis as they did not complete the study with sufficient data points. Objective assessment using colorimetry (SkinColorCatch, Delfin technologies, Kuopio, Finland) was performed. Measurement of the intensity of the blue/yellow channel was undertaken at all time points. This score was then compared with the baseline score prior to bruise creation and the delta between blue intensity and original clear skin was compared among the two groups and provided information of bruise resolution. In order to ensure equivalence of both groups, the scores immediately post bruising were determined to be comparable as demonstrated in FIG. 15A.

The 2 models showed slight variation. Subdermal injection manifested bruising slightly later; thus day 3 and 7 in this group was equivalent to day 2 and 6 in the blood draw group. The data demonstrated that the 'tipping point' occurred at day 2/3, where the color intensity of the experimental study product was significantly improved over the comparator. 81% of subjects applying the topical product had less bruising at Day 2/3 compared to the bland moisturizer, and there was a 72% improvement in purple intensity score, demonstrating that the topical product hastened resolution of bruising as seen in FIGS. 15A-15G.

Figure 15G:
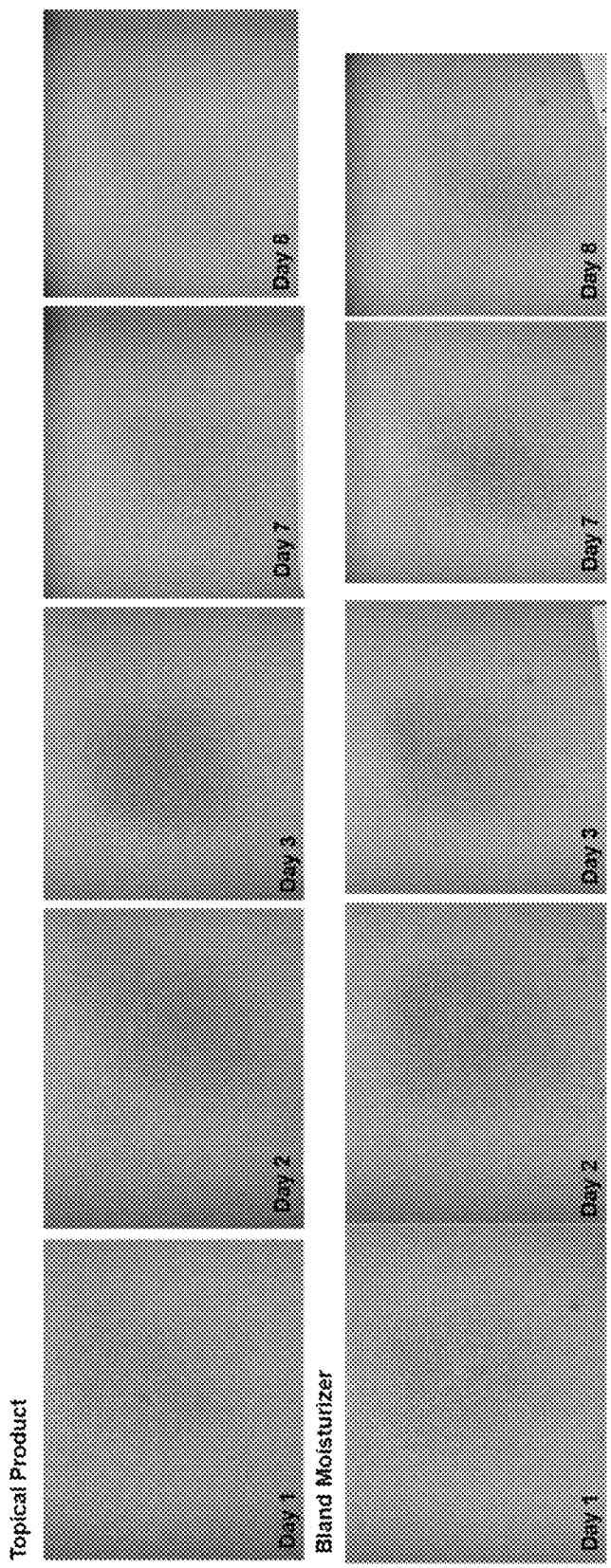
FIG. 15G shows images of bruising resolution following administration of the topical product or the bland moisturizer.

As seen in FIGS. 15A-15G, in many cases a transition from blue to red was observed in the experimental group receiving the topical product prior to resolution (e.g., day 3 of FIG. 15G of the topical product group). The topical product encourages macrophage efficiency (as validated in vitro) which then absorbs pigment, leaving residual red pigment which resolves very quickly.

Figure 16A:
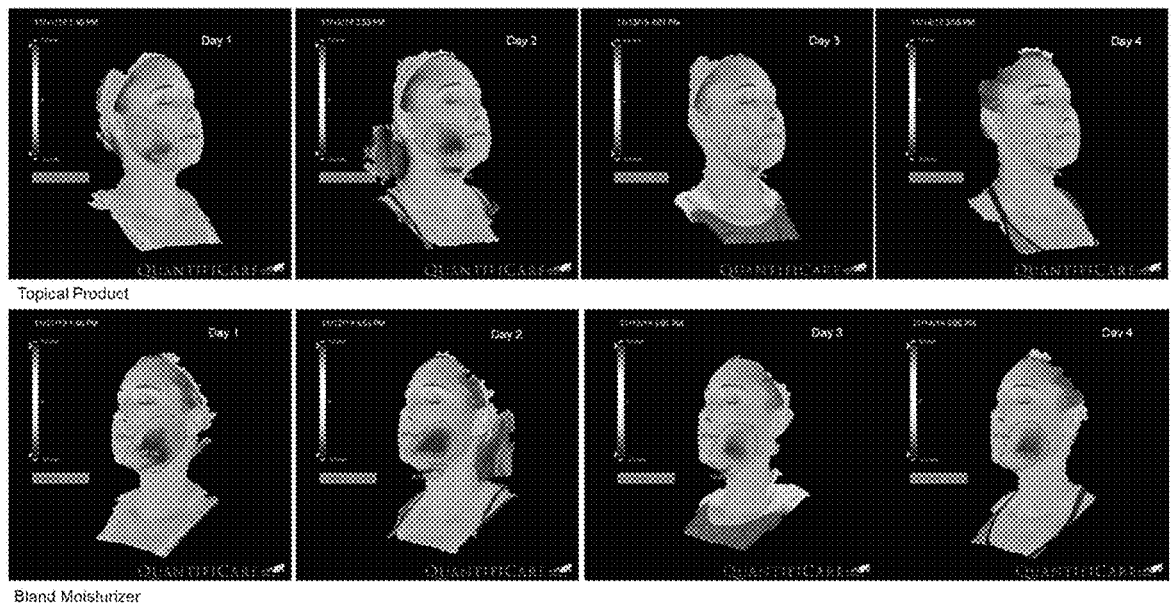
FIG. 16A shows images of swelling in a first subject administered the topical product as compared to the bland moisturizer at Day 1, Day 2, Day 3, and Day 4.
Figure 16B:
FIG. 16B shows images of swelling in a second subject administered the topical product as compared to the bland moisturizer at Day 1, Day 2, Day 3, and Day 4.

Swelling was also measured. Subjects underwent Profound Radiofrequency (RF) Microneedling procedure and were administered the topical product comprising a formula as described in Table 9 or a bland moisturizer. Split face case studies were used to compare the topical product and the bland moisturizer. A Quantificare 3-D volumetric camera was used for measurements. Red color indicates greater volume/swelling compared to baseline. Data is seen in FIGS. 16A-16B.

Figure 16C:
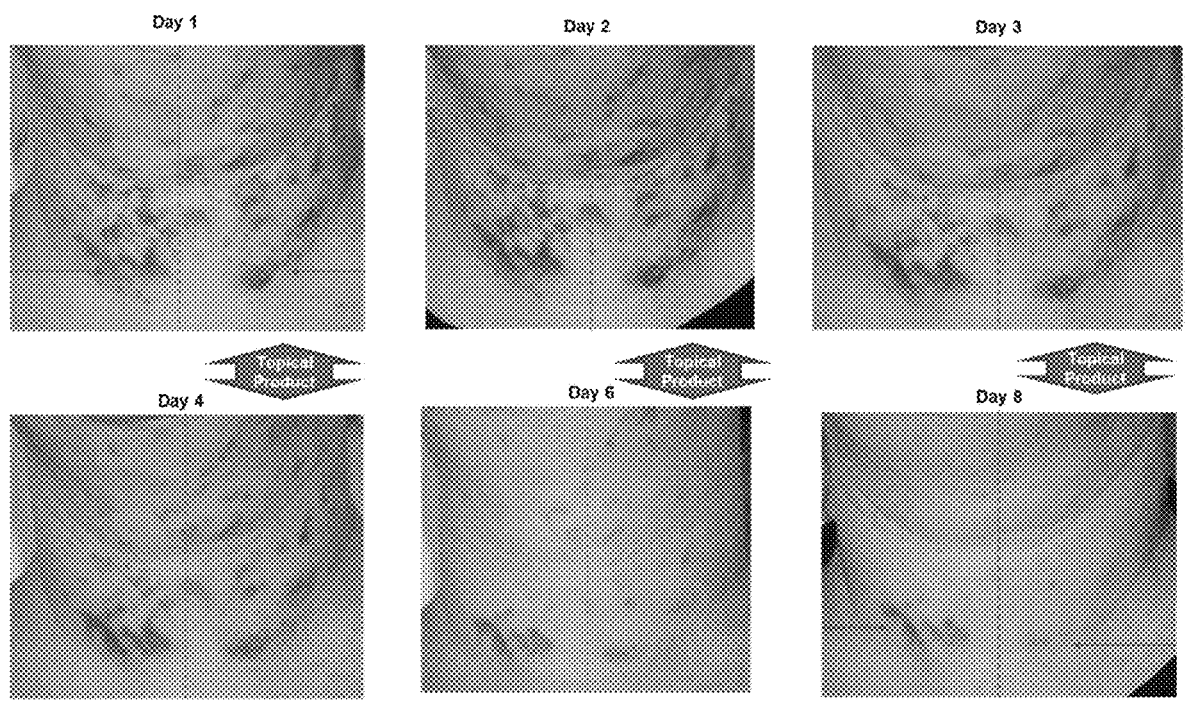
FIG. 16C shows images of bruising resolution in a subject treated with radiofrequency (RF) needling and administered the topical product.
Figure 16D:
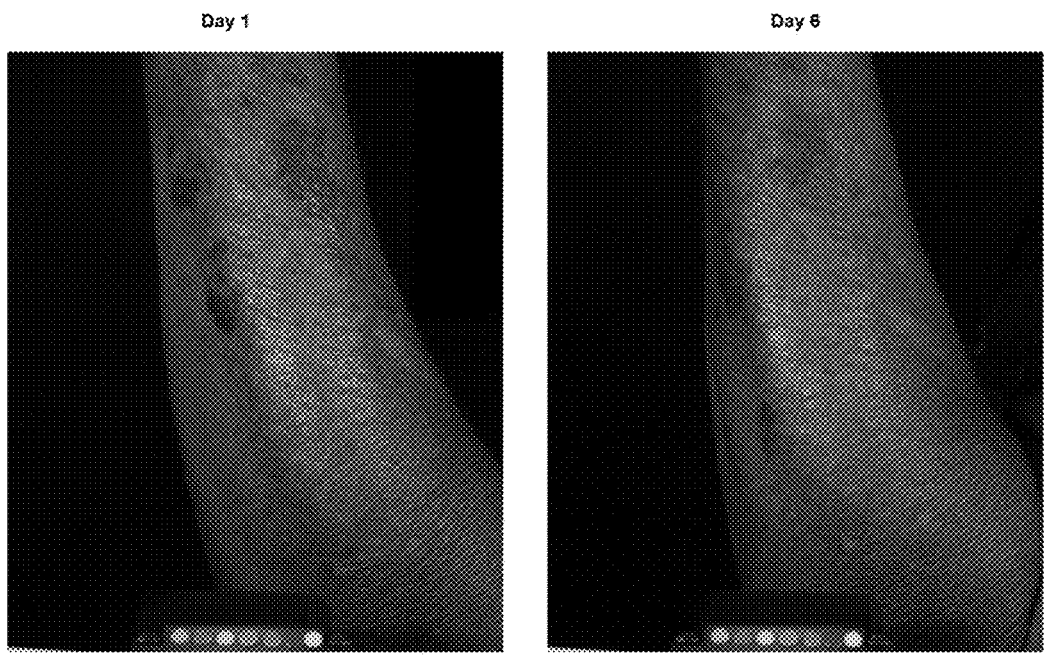
FIG. 16D shows images of bruising resolution following administration of the topical product.

As seen in FIG. 16C, application of the topical product (right side of each image) over a period of 8 days reduced bruising and swelling in a subject treated with radiofrequency (RF) microneedling. Application of the topical product also reduced senile purpura as seen in FIG. 16D.

Figure 16E:
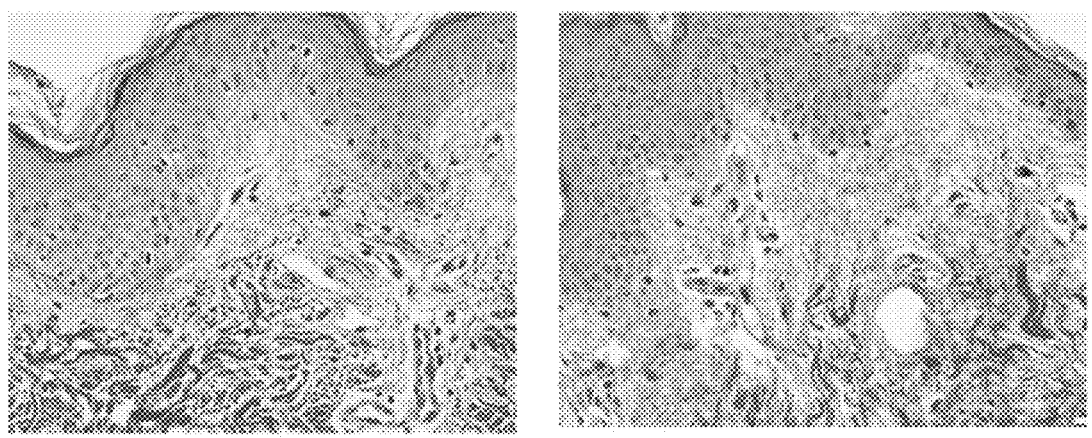
FIG. 16E shows images of a Herovici stain (40× magnification) demonstrating new mucopolysaccharide formation (denoted by blue areas in papillary dermis). The left panel is pretreatment and the right panel is 2 weeks after use of the topical product.

Molecular changes were also observed. As seen in FIG. 16E, the Herovici stain (40× magnification) demonstrates new mucopolysaccharide formation (denoted by blue areas in papillary dermis). The left panel is pretreatment and the right panel is 2 weeks after use of the topical product. As seen in FIG. 16F, the fibrillin stain (10× magnification) in brown shows regeneration of elastin fibers. The left panel is pretreatment and the right panel is 2 weeks after use of the topical product.

Conclusion

The data demonstrate improvements in bruising resolution using the topical product.

Example 11. In Vitro Antimicrobial Effectiveness of the Topical Product

An Antimicrobial Effectiveness Test was performed using a topical product having a formula of Table 9. As seen in the data in FIG. 17, there was a complete eradication of bacteria, yeast, and mold using the topical product. The topical product was determined to meet the USP criteria of acceptance for the Antimicrobial Effectiveness Test for Category 2.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What we claim is:

1. A method for improving healing of a bruise or improving appearance of a bruise on human skin, the method comprising:
   administering a topical composition to human skin that has been subjected to a medical procedure, wherein the topical composition comprises:
   a tripeptide-1; and
   a hexapeptide-11.

2. The method of claim 1, wherein the medical procedure is an injection or an invasive surgery.

3. The method of claim 2, wherein the injection comprises a filler or a neurotoxin.

4. The method of claim 1, wherein the tripeptide-1 is present at a concentration of 1-10 ppm.

5. The method of claim 1, wherein the hexapeptide-11 is present at a concentration of 50-150 ppm.

6. The method of claim 1, wherein the composition further comprises at least one of a hexapeptide-12, a hexapeptide-38, or a tetrapeptide-2.

7. The method of claim 6, wherein at least one of the hexapeptide-11, the hexapeptide-38, the hexapeptide-12, or the tetrapeptide-2 is encapsulated in a liposome.

8. The method of claim 7, wherein the liposome comprises at least one of lactoferrin or phosphatidylserine.

9. The method of claim 1, wherein the composition further comprises at least one of: *Ledun palustre* extract, dill extract, *Tremella fuciformis* extract, butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl methicone, phenoxy ethanol, ethylhexylglycerin, polyacrylate-13, polyisobutene, polysorhate 20, caprylhydroxamic acid, disodium EDTA, *Arnica Montana* extract, sorbitan isostearate, pentylene glycol, glucose, sunflower seed oil, radish root ferment filtrate, potassium sorbate, sodium hyaluronate crosspolyrner, xylilylglucoside, anhydroxyliml, xylitol, hydroxymethoxyphenyl decanone, or combinations thereof.

10. A method for improving healing of a bruise or improving appearance of a bruise on human skin, the method comprising:
administering a topical composition to human skin that has been subjected to a cosmetic procedure, wherein the topical composition comprises:
a tripeptide-1; and
a hexapeptide-11.

11. The method of claim 10, wherein the cosmetic procedure is an injection of a filler, micro-needling, an injection of a neurotoxin, or an invasive surgery.

12. The method of claim 10, wherein the tripeptide-1 is present at a concentration of 1-10 ppm.

13. The method of claim 10, wherein the hexapeptide-11 is present at a concentration of 50-150 ppm.

14. The method of claim 10, wherein the composition further comprises at least one of a hexapeptide-12, a hexapeptide-38, or a tetrapeptide-2.

15. The method of claim 14, wherein at least one of the hexapeptide-11, the hexapeptide-38, the hexapeptide-12, or the tetrapeptide-2 is present in a liposome.

16. The method of claim 15, wherein the liposome comprises at least one of lactoferrin or phosphatidylserine.

17. The method of claim 10, wherein the composition further comprises at least one of: *Ledum palustre* extract, dill extract, *Tremella fuciformis* extract, butylene glycol, glycerin, squalane, *Dunaliella salina* extract, phospholipids, tocopherol, ascorbyl palmitate, xanthan gum, betaine, propanediol, lecithin, caprylic/capric triglyceride, caprylyl glycol, caprylyl nlethicone, phenoxy ethanol, ethylhexylglycerin, polyacrylate-13, polyisobutene, polysorbate 20, caprylhydroxamic acid, disodium EDTA, *Arnica Montana* extract, sorbitan isostearate, pentylene glycol, glucose, sunflower seed oil, radish root ferment filtrate, potassium sorbate, sodium hyaluronate crosspolymer, xylitylglucoside, anhydroxylitol, xylitol, hydroxymethoxyphenyl decanone, or combinations thereof.

18. A method for improving healing of a bruise or improving appearance of a bruise on human skin, the method comprising:
instructing the administration of a topical composition to human skin that has been subjected to a medical or cosmetic procedure, wherein the topical composition comprises:
a tripeptide-1; and
a hexapeptide-11.

* * * * *